United States Patent [19]
Janjic et al.

[11] Patent Number: 6,051,698
[45] Date of Patent: *Apr. 18, 2000

[54] VASCULAR ENDOTHELIAL GROWTH FACTOR (VEGF) NUCLEIC ACID LIGAND COMPLEXES

[76] Inventors: Nebojsa Janjic, 6973 Carter Trail, Boulder, Colo. 80301; Larry Gold, 1033 Fifth St., Boulder, Colo. 80302; Paul Schmidt, P.O. Box 1125, Niwot, Colo. 80544; Chandra Vargeese, 5295 E. 17th Ave., Thornton, Colo. 80233

[*] Notice: This patent is subject to a terminal disclaimer.

[21] Appl. No.: 08/897,351

[22] Filed: Jul. 21, 1997

Related U.S. Application Data

[63] Continuation-in-part of application No. 08/870,930, Jun. 6, 1997.

[51] Int. Cl.[7] .......................... C07H 21/02; C07H 21/04; C12Q 1/68; A61K 31/70
[52] U.S. Cl. .............................. 536/24.31; 435/6; 514/44; 935/77; 935/78
[58] Field of Search .............................. 536/24.31; 435/6; 514/44; 935/77, 78

[56] References Cited

U.S. PATENT DOCUMENTS

| | | | |
|---|---|---|---|
| 4,904,582 | 2/1990 | Tullis | 435/6 |
| 4,914,210 | 4/1990 | Levenson et al. | 548/413 |
| 4,962,029 | 10/1990 | Levenson et al. | 435/7 |
| 4,997,652 | 3/1991 | Wong | 435/6 |
| 5,149,794 | 9/1992 | Yatvin et al. | 435/6 |
| 5,245,022 | 9/1993 | Weis et al. | 435/6 |
| 5,270,163 | 12/1993 | Gold et al. | 435/6 |
| 5,459,015 | 10/1995 | Janjic et al. | 435/6 |
| 5,475,096 | 12/1995 | Gold et al. | 435/6 |
| 5,595,877 | 1/1997 | Gold et al. | 435/6 |
| 5,659,013 | 8/1997 | Senger et al. | 530/350 |
| 5,710,136 | 1/1998 | Robinson et al. | 514/44 |

FOREIGN PATENT DOCUMENTS

| | | |
|---|---|---|
| 292 128 A1 | 11/1988 | European Pat. Off. . |
| 0462145 | 4/1994 | European Pat. Off. . |
| 9010448 | 9/1990 | WIPO . |
| 9114696 | 10/1991 | WIPO . |
| 9214843 | 9/1992 | WIPO . |
| WO93/08210 | 4/1993 | WIPO . |
| 9401448 | 1/1994 | WIPO . |
| WO94/10202 | 5/1994 | WIPO . |
| 9415619 | 7/1994 | WIPO . |
| 9427615 | 12/1994 | WIPO . |
| 9429479 | 12/1994 | WIPO . |
| 9500529 | 1/1995 | WIPO . |
| 9506474 | 3/1995 | WIPO . |
| 9506659 | 3/1995 | WIPO . |
| 9621469 | 7/1996 | WIPO . |
| WO96/30046 | 10/1996 | WIPO . |
| WO97/09427 | 3/1997 | WIPO . |

OTHER PUBLICATIONS

Jakeman et al. (1992) J. Clin. Invest. 89:244.
Jaschke et al., "Synthesis and properties of oligodeoxyribonucleotide–polyethylene glycol conjugates," Nuc. Acids Res. 22(22):4810–4817, 1994.
MacKellar et al., "Synthesis and physical properties of anti–HIV antisense oligonucleotides bearing terminal lipophilic groups," Nuc. Acids Res. 20(13):3411–3417, 1992.
Shea et al., "Synthesis, hybridization properties and antiviral activity of lipid–oligodeoxynucleotide conjugates," Nuc. Acids Res. 18(13):3777–3483, 1990.

*Primary Examiner*—Stephanie Zitomer

[57] ABSTRACT

This invention discloses a method for preparing a complex comprised of a VEGF Nucleic Acid Ligand and a Non-Immunogenic, High Molecular Weight Compound or Lipophilic Compound by identifying a VEGF Nucleic Acid Ligand by SELEX methodology and associating the VEGF Nucleic Acid Ligand with a Non-Immunogenic, High Molecular Weight Compound or Lipophilic Compound. The invention further discloses Complexes comprising one or more VEGF Nucleic Acid Ligands in association with a Non-Immunogenic, High Molecular Weight Compound or Lipophilic Compound. The invention further includes a Lipid construct comprising a VEGF Nucleic Acid Ligand or Complex and methods for making the same.

21 Claims, 13 Drawing Sheets

NX31838 - PL

Ligand Component =
fCmGmGrArAfUfCmAmGfUmGmAmAfUmGfCfUfUmAfUmAfCmAfUfCfCmG-3'3'-dT
(VEGF ligand)

SEQ ID NO:5

NX31838 Lipid-amide 1

Ligand Component =
fCmGmGrArAfUfCmAmGfUmGmAmAfUmGfCfUfUmAfUmAfCmAfUfCfCmG-3'3'-dT
(VEGF ligand)

SEQ ID NO:6

NX31838 Lipid-amide 2

Ligand Component =
fCmGmGrArAfUfCmAmGfUmGmAmAfUmGfCfUfUmAfUmAfCmAfUfCfCmG-3'3'-dT
(VEGF ligand)

SEQ ID NO:7

FIGURE 1C

NX31838  40K mPEG

Ligand Component =
fCmGmGrArAfUfCmAmGfUmGmAmAfUmGfCfUfUmAfUmAfCmAfUfCfCmG-3'3'-dT
(VEGF ligand)

SEQ ID NO:8

FIGURE 1D

NX31838  20Km PEG

Ligand Component =
fCmGmGrArAfUfCmAmGfUmGmAmAfUmGfCfUfUmAfUmAfCmAfUfCfCmG-3'3'-dT
(VEGF ligand)

SEQ ID NO:9

FIGURE 1E

SEQUENCE LISTING (1) GENERAL INFORMATION:

(iii) NUMBER OF SEQUENCES: 88

(2) INFORMATION FOR SEQ ID NO: 1:

(i) SEQUENCE CHARACTERISTICS:
       (A) LENGTH:  78
       (B) TYPE:  nucleic acid
       (C) STRANDEDNESS:  single
       (D) TOPOLOGY:  linear (ii) MOLECULE TYPE:  RNA (ix) FEATURE:
       (D) OTHER INFORMATION:

(xi) SEQUENCE DESCRIPTION:  SEQ ID NO: 1:

TAATACGACT CACTATAGGG AGGACGATGC GGNNNNNNNN NNNNNNNNNN          50

NNNNNNNNNN NNCAGACGAC TCGCCCGA                                 78

(2) INFORMATION FOR SEQ ID NO: 2:

(i) SEQUENCE CHARACTERISTICS:
       (A) LENGTH:  88
       (B) TYPE:  nucleic acid
       (C) STRANDEDNESS:  single
       (D) TOPOLOGY:  linear (ii) MOLECULE TYPE:  RNA (ix) FEATURE:
       (D) OTHER INFORMATION:

(xi) SEQUENCE DESCRIPTION:  SEQ ID NO: 2:

TAATACGACT CACTATAGGG AGGACGATGC GGNNNNNNNN NNNNNNNNNN          50

NNNNNNNNNN NNNNNNNNNN NNCAGACGAC TCGCCCGA                      88

(2) INFORMATION FOR SEQ ID NO: 3:

(i) SEQUENCE CHARACTERISTICS:
       (A) LENGTH:  16
       (B) TYPE:  nucleic acid
       (C) STRANDEDNESS:  single
       (D) TOPOLOGY:  linear (ii) MOLECULE TYPE:  RNA (ix) FEATURE:
       (D) OTHER INFORMATION:

(xi) SEQUENCE DESCRIPTION:  SEQ ID NO: 3:

TCGGGCGAGT CGTCTG                                              16

(2) INFORMATION FOR SEQ ID NO: 4:

(i) SEQUENCE CHARACTERISTICS:
       (A) LENGTH:  32
       (B) TYPE:  nucleic acid
       (C) STRANDEDNESS:  single
       (D) TOPOLOGY:  linear (ii) MOLECULE TYPE:  RNA (ix) FEATURE:

```
        (D) OTHER INFORMATION:

(xi) SEQUENCE DESCRIPTION: SEQ ID NO: 4:

TAATACGACT CACTATAGGG AGGACGATGC GG                                        32

(2) INFORMATION FOR SEQ ID NO: 5:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1, 6-7,
            10, 14, 16-18, 20, 22, and 24-26 are 2'-fluoro (2'-F)
            modified (ix) FEATURE:
        (D) OTHER INFORMATION: Nucleotides at positions 2-3,
            8-9, 11-13, 15, 19, 21, 23, and 27 are 2'-OMethyl
            (2'-OMe) modified (ix) FEATURE:
        (D) OTHER INFORMATION: T in position 28 is a 3'-3'-linked
            deoxythymidine (xi) SEQUENCE DESCRIPTION: SEQ ID NO: 5:

CGGAAUCAGU GAAUGCUUAU ACAUCCGT                                             28

(2) INFORMATION FOR SEQ ID NO: 6:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1,
            6-7, 10, 14, 16-18, 20, 22, and 24-26 are 2'-fluoro
            (2'-F) modified (ix) FEATURE:
        (D) OTHER INFORMATION: Nucleotides at positions 2-3,
            8-9, 11-13, 15, 19, 21, 23, and 27 are 2'-OMethyl
            (2'-OMe) modified (ix) FEATURE:
        (D) OTHER INFORMATION: T in position 28 is a 3'-3'-linked
            deoxythymidine (xi) SEQUENCE DESCRIPTION: SEQ ID NO: 6:

CGGAAUCAGU GAAUGCUUAU ACAUCCGT                                             28

(2) INFORMATION FOR SEQ ID NO: 7:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
```

(D) OTHER INFORMATION: Nucleotides at positions 1,
     6-7, 10, 14, 16-18, 20, 22, and 24-26 are 2'-fluoro
     (2'-F) modified (ix) FEATURE:
     (D) OTHER INFORMATION: Nucleotides at positions 2-3,
          8-9, 11-13, 15, 19, 21, 23, and 27 are 2'-OMethyl
          (2'-OMe) modified (ix) FEATURE:
     (D) OTHER INFORMATION: T in position 28 is a 3'-3'-linked
          deoxythymidine (xi) SEQUENCE DESCRIPTION: SEQ ID NO: 7:

CGGAAUCAGU GAAUGCUUAU ACAUCCGT                                28

(2) INFORMATION FOR SEQ ID NO: 8:

(i) SEQUENCE CHARACTERISTICS:
          (A) LENGTH: 28
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: Nucleotides at positions 1,
               6-7, 10, 14, 16-18, 20, 22, and 24-26 are 2'-fluo
               (2'-F) modified (ix) FEATURE:
          (D) OTHER INFORMATION: Nucleotides at positions
               2-3, 8-9, 11-13, 15, 19, 21, 23, and 27 are 2'-OMethyl
               (2'-OMe) modified (ix) FEATURE:
          (D) OTHER INFORMATION: T in position 28 is a 3'-3'-linked
               deoxythymidine (xi) SEQUENCE DESCRIPTION: SEQ ID NO: 8:

CGGAAUCAGU GAAUGCUUAU ACAUCCGT                                28

(2) INFORMATION FOR SEQ ID NO: 9:

(i) SEQUENCE CHARACTERISTICS:
          (A) LENGTH: 28
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: Nucleotides at positions 1,
               6-7, 10, 14, 16-18, 20, 22, and 24-26 are 2'-fluoro
               (2'-F) modified (ix) FEATURE:
          (D) OTHER INFORMATION: Nucleotides at positions 2-3,
               8-9, 11-13, 15, 19, 21, 23, and 27 are 2'-OMethyl
               (2'-OMe) modified (ix) FEATURE:
          (D) OTHER INFORMATION: T in position 28 is a 3'-3'-linked
               deoxythymidine (xi) SEQUENCE DESCRIPTION: SEQ ID NO: 9:

CGGAAUCAGU GAAUGCUUAU ACAUCCGT                                28

(2) INFORMATION FOR SEQ ID NO: 10:

```
    (i) SEQUENCE CHARACTERISTICS:
        (A) LENGTH:  61
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro (2'-F) modified (xi) SEQUENCE DESCRIPTION:  SEQ ID NO: 10:

GGGAGGACGA UGCGGNNNNN NNNNNNNNNN NNNNNNNNNN NNNNNCAGAC         50

GACUCGCCCG A                                                  61

(2) INFORMATION FOR SEQ ID NO: 11:

(i) SEQUENCE CHARACTERISTICS:
        (A) LENGTH:  71
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified (xi) SEQUENCE DESCRIPTION:  SEQ ID NO: 11:

GGGAGGACGA UGCGGNNNNN NNNNNNNNNN NNNNNNNNNN NNNNNNNNNN         50

NNNNNCAGAC GACUCGCCCG A                                       71

(2) INFORMATION FOR SEQ ID NO: 12:

(i) SEQUENCE CHARACTERISTICS:
        (A) LENGTH:  61
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified (xi) SEQUENCE DESCRIPTION:  SEQ ID NO: 12:

GGGAGGACGA UGCGGAAGAA UUGGUCAUCG UCGUCUCCGC CUCCCCAGAC         50

GACUCGCCCG A                                                  61

(2) INFORMATION FOR SEQ ID NO: 13:

(i) SEQUENCE CHARACTERISTICS:
        (A) LENGTH:  61
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified
```

-continued

```
    (xi) SEQUENCE DESCRIPTION: SEQ ID NO: 13:

GGGAGGACGA UGCGGAAUAC GGAAGAAUUG GAUACAUAUG CUCGUCAGAC        50

GACUCGCCCG A                                                 61

(2) INFORMATION FOR SEQ ID NO: 14:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 14:

GGGAGGACGA UGCGGGAUAA CAGAAGAAUU GGUGAACAAC GUGGUCAGAC        50

GACUCGCCCG A                                                 61

(2) INFORMATION FOR SEQ ID NO: 15:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 15:

GGGAGGACGA UGCGGAUGAU CGCGUAGGAA GUAUUGGAAG GCCCUCAGAC        50

GACUCGCCCG A                                                 61

(2) INFORMATION FOR SEQ ID NO: 16:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 16:

GGGAGGACGA UGCGGCACUU UAGAAGAAUU GAAUUUCCCG CUGGUCAGAC        50

GACUCGCCCG A                                                 61

(2) INFORMATION FOR SEQ ID NO: 17:

(i) SEQUENCE CHARACTERISTICS:
        (A) LENGTH: 61
        (B) TYPE: nucleic acid
        (C) STRANDEDNESS: single
        (D) TOPOLOGY: linear
```

(ii) MOLECULE TYPE: RNA (ix) FEATURE:
            (D) OTHER INFORMATION: All pyrimidines are 2'-fluoro
                (2'-F) modified (xi) SEQUENCE DESCRIPTION: SEQ ID NO: 17:

GGGAGGACGA UGCGGUAGGA AGAAUUGGAA GCGCAUUUUC CUCGYCAGAC         50

GACUCGCCCG A                                                  61

(2) INFORMATION FOR SEQ ID NO: 18:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-fluoro
                (2'-F) modified (xi) SEQUENCE DESCRIPTION: SEQ ID NO: 18:

GGGAGGACGA UGCGGCGGGA UUUUGGAAGA AUUGGAUAUU GGCCUCAGAC         50

GACUCGCCCG A                                                  61

(2) INFORMATION FOR SEQ ID NO: 19:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-fluoro
                (2'-F) modified (xi) SEQUENCE DESCRIPTION: SEQ ID NO: 19:

GGGAGGACGA UGCGGCGGYA CUUUGGAAGA AUUGAAUUUC CCGCUCAGAC         50

GACUCGCCCG A                                                  61

(2) INFORMATION FOR SEQ ID NO: 20:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-fluoro
                (2'-F) modified (xi) SEQUENCE DESCRIPTION: SEQ ID NO: 20:

GGGAGGACGA UGCGGAAGAA UUGGAUAUAU CGUUCACCCC CACCUCAGAC         50

GACUCGCCCG A                                                  61

-continued (2) INFORMATION FOR SEQ ID NO: 21:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 21:

GGGAGGACGA UGCGGAAACG GAAGAAUUGG AUACGCAAGC ACGUUCAGAC          50

GACUCGCCCG A          61

(2) INFORMATION FOR SEQ ID NO: 22:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 22:

GGGAGGACGA UGCGGUAGGA AGUAUUGUAA GCGCCUCGUU UUCGCCAGAC          50

GACUCGCCCG A          61

(2) INFORMATION FOR SEQ ID NO: 23:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 23:

GGGAGGACGA UGCGGAGUUU UGGAAGAAUU GGAUGUUCCG AUCGUCAGAC          50

GACUCGCCCG A          61

(2) INFORMATION FOR SEQ ID NO: 24:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified -continued

```
    (xi) SEQUENCE DESCRIPTION: SEQ ID NO: 24:

GGGAGGACGA UGCGGAAGAA ACGGAAGAAU UGGAGACACG CUCGUCAGAC        50

GACUCGCCCG A                                                  61

(2) INFORMATION FOR SEQ ID NO: 25:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 25:

GGGAGGACGA UGCGGGAAGA AUUGAUGUUG UAUUGUCCUU CCGAUUUCCU        50

GCCGUCAGAC GACUCGCCCG A                                       71

(2) INFORMATION FOR SEQ ID NO: 26:

(i) SEQUENCE CHARACTERISTICS:
        (A) LENGTH: 70
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 26:

GGGAGGACGA UGCGGACAGA AGAAUUGGGC UUCGCAUUAU CCUCUGUCAG        50

CCGCCAGACG ACUCGCCCGA                                         70

(2) INFORMATION FOR SEQ ID NO: 27:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 27:

GGGAGGACGA UGCGGUGAGA GAAACGGAAG AAUUGGAUAC GAUACUCAUC        50

GCGCUCAGAC GACUCGCCCG A                                       71

(2) INFORMATION FOR SEQ ID NO: 28:

(i) SEQUENCE CHARACTERISTICS:
        (A) LENGTH: 61
        (B) TYPE: nucleic acid
        (C) STRANDEDNESS: single
        (D) TOPOLOGY: linear
```

(ii) MOLECULE TYPE: RNA (ix) FEATURE:
             (D) OTHER INFORMATION: All pyrimidines are 2'-fluoro
                 (2'-F) modified (xi) SEQUENCE DESCRIPTION: SEQ ID NO: 28:

GGGAGGACGA UGCGGCUUAA GUUUUGGAAG AAUUGAAUAC UGGGUCAGAC         50

GACUCGCCCG A                                                  61

(2) INFORMATION FOR SEQ ID NO: 29:

(i) SEQUENCE CHARACTERISTICS:
             (A) LENGTH: 60
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-fluoro
                 (2'-F) modified (xi) SEQUENCE DESCRIPTION: SEQ ID NO: 29:

GGGAGGACGA UGCGGUAACC AGUGGAAGAA UUGGCUGCUA UCCUCAGACG         50

ACUCGCCCGA                                                    60

(2) INFORMATION FOR SEQ ID NO: 30:

(i) SEQUENCE CHARACTERISTICS:
             (A) LENGTH: 60
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-fluoro
                 (2'-F) modified (xi) SEQUENCE DESCRIPTION: SEQ ID NO: 30:

GGGAGGACGA UGCGGAACGG AAGAAUUGGA UACGUAGCAU GCGUCAGACG         50

ACUCGCCCGA                                                    60

(2) INFORMATION FOR SEQ ID NO: 31:

(i) SEQUENCE CHARACTERISTICS:
             (A) LENGTH: 61
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-fluoro
                 (2'-F) modified (xi) SEQUENCE DESCRIPTION: SEQ ID NO: 31:

GGGAGGACGA UGCGGCAGGA UUUUGGAAGA AUUGGAUAUU GGCCGCAGAC         50

GACUCGCCCG A                                                  61

-continued (2) INFORMATION FOR SEQ ID NO: 32:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 32:

GGGAGGACGA UGCGGAAACG GAAGAAUUGG AUACCGCUAC GUGUUCAGAC          50

GACUCGCCCG A          61

(2) INFORMATION FOR SEQ ID NO:33:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 33:

GGGAGGACGA UGCGGAAGAA UUGAGCAUUC CUUCUCCUUG UGCCUCAGAC          50

GACUCGCCCG A          61

(2) INFORMATION FOR SEQ ID NO: 34:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 34:

GGGAGGACGA UGCGGAGCUA ACGGAAGAAU UGGAAACAAC CGCGUCAGAC          50

GACUCGCCCG A          61

(2) INFORMATION FOR SEQ ID NO: 35:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified -continued (xi) SEQUENCE DESCRIPTION: SEQ ID NO: 35:

GGGAGGACGA UGCGGYGAAC CGAUGGAAUU UUUGGACGCU CGCCUCAGAC         50

GACUCGCCCG A                                                  61

(2) INFORMATION FOR SEQ ID NO: 36:

(i) SEQUENCE CHARACTERISTICS:
              (A) LENGTH: 61
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-fluoro
                   (2'-F) modified (xi) SEQUENCE DESCRIPTION: SEQ ID NO: 36:

GGGAGGACGA UGCGGAYCAA CCGAUUGACG UUAUGGGACG CUGGUCAGAC         50

GACUCGCCCG A                                                  61

(2) INFORMATION FOR SEQ ID NO: 37:

(i) SEQUENCE CHARACTERISTICS:
              (A) LENGTH: 61
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-fluoro
                   (2'-F) modified (xi) SEQUENCE DESCRIPTION: SEQ ID NO: 37:

GGGAGGACGA UGCGGUAACC GAUUGAACUU CUUGGACGCU ACCGUCAGAC         50

GACUCGCCCG A                                                  61

(2) INFORMATION FOR SEQ ID NO: 38:

(i) SEQUENCE CHARACTERISTICS:
              (A) LENGTH: 61
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-fluoro
                   (2'-F) modified (xi) SEQUENCE DESCRIPTION: SEQ ID NO: 38:

GGGAGGACGA UGCGGUAACC GAAUUGAAGU UAUUGGACGC UACCUCAGAC         50

GACUCGCCCG A                                                  61

(2) INFORMATION FOR SEQ ID NO: 39:

(i) SEQUENCE CHARACTERISTICS:
              (A) LENGTH: 71
              (B) TYPE: nucleic acid
              (C) STRANDEDNESS: single
              (D) TOPOLOGY: linear

```
    (ii) MOLECULE TYPE:  RNA (ix) FEATURE:
         (D) OTHER INFORMATION:  All pyrimidines are 2'-fluoro
             (2'-F) modified (xi) SEQUENCE DESCRIPTION:  SEQ ID NO: 39:

GGGAGGACGA UGCGGGAGCA GAACCGAUAG AAGAAUUGGA CGCUCAGCUC          50

CGGGUCAGAC GACUCGCCCG A                                         71

(2) INFORMATION FOR SEQ ID NO: 40:

(i) SEQUENCE CHARACTERISTICS:
        (A) LENGTH:  71
        (B) TYPE:  nucleic acid
        (C) STRANDEDNESS:  single
        (D) TOPOLOGY:  linear (ii) MOLECULE TYPE:  RNA (ix) FEATURE:
         (D) OTHER INFORMATION:  All pyrimidines are 2'-fluoro
             (2'-F) modified (xi) SEQUENCE DESCRIPTION:  SEQ ID NO: 40:

GGGAGGACGA UGCGGGUACC AGAAUGAGCA ACCGAAUGAA GAACUGGACG          50

CUGCUCAGAC GACUCGCCCG A                                         71

(2) INFORMATION FOR SEQ ID NO: 41:

(i) SEQUENCE CHARACTERISTICS:
        (A) LENGTH:  71
        (B) TYPE:  nucleic acid
        (C) STRANDEDNESS:  single
        (D) TOPOLOGY:  linear (ii) MOLECULE TYPE:  RNA (ix) FEATURE:
         (D) OTHER INFORMATION:  All pyrimidines are 2'-fluoro
             (2'-F) modified (xi) SEQUENCE DESCRIPTION:  SEQ ID NO: 41:

GGGAGGACGA UGCGGUGAAC CGAUGGAAUC GCUUGGACGC UCAUCGCACG          50

UUGCUCAGAC GACUCGCCCG A                                         71

(2) INFORMATION FOR SEQ ID NO: 42:

(i) SEQUENCE CHARACTERISTICS:
        (A) LENGTH:  61
        (B) TYPE:  nucleic acid
        (C) STRANDEDNESS:  single
        (D) TOPOLOGY:  linear (ii) MOLECULE TYPE:  RNA (ix) FEATURE:
         (D) OTHER INFORMATION:  All pyrimidines are 2'-fluoro
             (2'-F) modified (xi) SEQUENCE DESCRIPTION:  SEQ ID NO: 42:

GGGAGGACGA UGCGGUCAAC CGGUUGAAUA UUUGGUCGCU GACCUCAGAC          50

GACUCGCCCG A                                                    61
```

-continued (2) INFORMATION FOR SEQ ID NO: 43:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
           (2'-F) modified (xi) SEQUENCE DESCRIPTION: SEQ ID NO: 43:

```
GGGAGGACGA UGCGGAACUA GUGAAUGCUU AUACGACCGU GUUGUCAGAC          50

GACUCGCCCG A                                                    61
```

(2) INFORMATION FOR SEQ ID NO: 44:

(i) SEQUENCE CHARACTERISTICS:
        (A) LENGTH: 60
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
           (2'-F) modified (xi) SEQUENCE DESCRIPTION: SEQ ID NO: 44:

```
GGGAGGACGA UGCGGAUCAG UGAAUGCUUA UAGACCGCCU CCGUCAGACG          50

ACUCGCCCGA                                                      60
```

(2) INFORMATION FOR SEQ ID NO: 45:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
           (2'-F) modified (xi) SEQUENCE DESCRIPTION: SEQ ID NO: 45:

```
GGGAGGACGA UGCGGAGAAU CAGUGAAUGC UUAUAAAUCU CGYGUCAGAC          50

GACUCGCCCG A                                                    61
```

(2) INFORMATION FOR SEQ ID NO: 46:

(i) SEQUENCE CHARACTERISTICS:
        (A) LENGTH: 62
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
           (2'-F) modified -continued

```
      (xi) SEQUENCE DESCRIPTION: SEQ ID NO: 46:

GGGAGGACGA UGCGGAAUCA GUGAAUGCUU AUAGCUCCCG CGUCCUCAGA         50

CGACUCGCCC GA                                                  62

(2) INFORMATION FOR SEQ ID NO: 47:

(i) SEQUENCE CHARACTERISTICS:
          (A) LENGTH: 60
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are 2'-fluoro
              (2'-F) modified (xi) SEQUENCE DESCRIPTION: SEQ ID NO: 47:

GGGAGGACGA UGCGGAACCA GUGAAUGCUU AUAAGACUGC UCGUCAGACG         50

ACUCGCCCGA                                                     60

(2) INFORMATION FOR SEQ ID NO: 48:

(i) SEQUENCE CHARACTERISTICS:
          (A) LENGTH: 61
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines
              are 2'-fluoro (2'-F) modified (xi) SEQUENCE DESCRIPTION: SEQ ID NO: 48:

GGGAGGACGA UGCGGAUCAG UGAAUGCUUA UAGACCGUAU UGCGUCAGAC         50

GACUCGCCCG A                                                   61

(2) INFORMATION FOR SEQ ID NO: 49:

(i) SEQUENCE CHARACTERISTICS:
          (A) LENGTH: 61
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All pyrimidines are
              2'-fluoro (2'-F) modified (xi) SEQUENCE DESCRIPTION: SEQ ID NO: 49:

GGGAGGACGA UGCGGAGAAU CAGUGAAUGC UUAUAAACCU CGUGUCAGAC         50

GACUCGCCCG A                                                   61

(2) INFORMATION FOR SEQ ID NO: 50:

(i) SEQUENCE CHARACTERISTICS:
          (A) LENGTH: 61
          (B) TYPE: nucleic acid
          (C) STRANDEDNESS: single
          (D) TOPOLOGY: linear
```

(ii) MOLECULE TYPE:  RNA (ix) FEATURE:
             (D) OTHER INFORMATION:  All pyrimidines are 2'-fluoro
                 (2'-F) modified (xi) SEQUENCE DESCRIPTION: SEQ ID NO: 50:

GGGAGGACGA UGCGGAAUCA GUGAAUGCUU AUAGCUCCGC GUGGUCAGAC        50

GACUCGCCCG A                                                  61

(2) INFORMATION FOR SEQ ID NO: 51:

(i) SEQUENCE CHARACTERISTICS:
             (A) LENGTH:  61
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-fluoro
                 (2'-F) modified (xi) SEQUENCE DESCRIPTION: SEQ ID NO: 51:

GGGAGGACGA UGCGGACCAG UGAAUGCUUA UAAGCCCAUC GACCUCAGAC        50

GACUCGCCCG A                                                  61

(2) INFORMATION FOR SEQ ID NO: 52:

(i) SEQUENCE CHARACTERISTICS:
             (A) LENGTH:  60
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-fluoro
                 (2'-F) modified (xi) SEQUENCE DESCRIPTION: SEQ ID NO: 52:

GGGAGGACGA UGCGGCAGGG UGAAUGCCAA UGUACUUUUC GCGUCAGACG        50

ACUCGCCCGA                                                    60

(2) INFORMATION FOR SEQ ID NO: 53:

(i) SEQUENCE CHARACTERISTICS:
             (A) LENGTH:  61
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-fluoro
                 (2'-F) modified (xi) SEQUENCE DESCRIPTION: SEQ ID NO: 53:

GGGAGGACGA UGCGGAAUCA GUGAAUGCUU AUACAUCCGC UCGGUCAGAC        50

GACUCGCCCG A                                                  61

(2) INFORMATION FOR SEQ ID NO: 54:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 54:

GGGAGGACGA UGCGGGACUA GGUGAAUGCC AAUAUUCUUC UCCGUCAGAC      50

GACUCGCCCG A      61

(2) INFORMATION FOR SEQ ID NO: 55:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (ix) FEATURE:
        (D) OTHER INFORMATION: N at position 30 is a 3'-3'-linked
            deoxythymidine (xi) SEQUENCE DESCRIPTION: SEQ ID NO: 55:

GACGAUGCGG UAGGAAGAAU UGGAAGCGCN      30

(2) INFORMATION FOR SEQ ID NO: 56:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (xi) SEQUENCE DESCRIPTION: SEQ ID NO: 56:

GACGAUGCGG UAGGAAGAAU UGGAAGCG      28

(2) INFORMATION FOR SEQ ID NO: 57:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified -continued (ix) FEATURE:
        (D) OTHER INFORMATION:  C in position 28 is 2'-OH C (xi) SEQUENCE DESCRIPTION:  SEQ ID NO: 57:

ACGAUGCGGU AGGAAGAAUU GGAAGCGC                                      28

(2) INFORMATION FOR SEQ ID NO: 58:

(i) SEQUENCE CHARACTERISTICS:
        (A) LENGTH:  23
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified (ix) FEATURE:
        (D) OTHER INFORMATION:  C in position 23 is 2'-OH C (xi) SEQUENCE DESCRIPTION:  SEQ ID NO: 58:

GCGGUAGGAA GAAUUGGAAG CGC                                           23

(2) INFORMATION FOR SEQ ID NO: 59:

(i) SEQUENCE CHARACTERISTICS:
        (A) LENGTH:  22
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified (ix) FEATURE:
        (D) OTHER INFORMATION:  C in position 22 is 2'-OH C (xi) SEQUENCE DESCRIPTION:  SEQ ID NO: 59:

CGGUAGGAAG AAUUGGAAGC GC                                            22

(2) INFORMATION FOR SEQ ID NO: 60:

(i) SEQUENCE CHARACTERISTICS:
        (A) LENGTH:  22
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified (ix) FEATURE:
        (D) OTHER INFORMATION:  N at position 22 is a
            3'-3'-linked deoxythymidine (xi) SEQUENCE DESCRIPTION:  SEQ ID NO: 60:

GGUAGGAAGA AUUGGAAGCG CN                                            22

(2) INFORMATION FOR SEQ ID NO: 61:

-continued (i) SEQUENCE CHARACTERISTICS:
        (A) LENGTH:  21
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are
            2'-fluoro (2'-F) modified (ix) FEATURE:
        (D) OTHER INFORMATION:  N at position 21 is a
            3'-3'-linked deoxythymidine (xi) SEQUENCE DESCRIPTION:  SEQ ID NO: 61:

GUAGGAAGAA UUGGAAGCGCN                                           21

(2) INFORMATION FOR SEQ ID NO: 62:

(i) SEQUENCE CHARACTERISTICS:
        (A) LENGTH:  32
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
(2'-F) modified (ix) FEATURE:
        (D) OTHER INFORMATION:  N at position 32 is a
            3'-3'-linked deoxythymidine (xi) SEQUENCE DESCRIPTION:  SEQ ID NO: 62:

GGCGAACCGA UGGAAUUUUU GGACGCUCGC CN                              32

(2) INFORMATION FOR SEQ ID NO: 63:

(i) SEQUENCE CHARACTERISTICS:
        (A) LENGTH:  29
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified (ix) FEATURE:
        (D) OTHER INFORMATION:  C in position 29 is 2'-OH C (xi) SEQUENCE DESCRIPTION:  SEQ ID NO: 63:

GCGAACCGAU GGAAUUUUUG GACGCUCGC                                  29

(2) INFORMATION FOR SEQ ID NO: 64:

(i) SEQUENCE CHARACTERISTICS:
        (A) LENGTH:  27
        (B) TYPE:  nucleic acid
        (C) STRANDEDNESS:  single
        (D) TOPOLOGY:  linear (ii) MOLECULE TYPE:  RNA -continued

```
        (ix) FEATURE:
              (D) OTHER INFORMATION:  All pyrimidines are 2'-fluoro
                  (2'-F) modified (xi) SEQUENCE DESCRIPTION: SEQ ID NO: 64:

CGAACCGAUG GAAUUUUGG ACGCUCG                                         27

(2) INFORMATION FOR SEQ ID NO: 65:

(i) SEQUENCE CHARACTERISTICS:
              (A) LENGTH: 26
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION:  All pyrimidines are 2'-fluoro
                  (2'-F) modified (ix) FEATURE:
              (D) OTHER INFORMATION:  N at position 26 is a
                  3'-3'-linked deoxythymidine (xi) SEQUENCE DESCRIPTION: SEQ ID NO: 65:

GAACCGAUGG AAUUUUGGA CGCUCN                                          26

(2) INFORMATION FOR SEQ ID NO: 66:

(i) SEQUENCE CHARACTERISTICS:
              (A) LENGTH: 24
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION:  All pyrimidines are 2'-fluoro
                  (2'-F) modified (ix) FEATURE:
              (D) OTHER INFORMATION:  N at position 24 is a
                  3'-3'-linked deoxythymidine (xi) SEQUENCE DESCRIPTION: SEQ ID NO: 66:

AACCGAUGGA AUUUUGGAC GCUN                                            24

(2) INFORMATION FOR SEQ ID NO: 67:

(i) SEQUENCE CHARACTERISTICS:
              (A) LENGTH: 22
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION:  All pyrimidines are 2'-fluoro
                  (2'-F) modified (ix) FEATURE:
              (D) OTHER INFORMATION:  N at position 22 is a
                  3'-3'-linked deoxythymidine (xi) SEQUENCE DESCRIPTION: SEQ ID NO: 67:

ACCGAUGGAA UUUUGGACG CN                                              22
```

(2) INFORMATION FOR SEQ ID NO: 68:

(i) SEQUENCE CHARACTERISTICS:
        (A) LENGTH:  30
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified (ix) FEATURE:
        (D) OTHER INFORMATION:  N at position 30 is a
            3'-3'-linked deoxythymidine (xi) SEQUENCE DESCRIPTION:  SEQ ID NO: 68:

GCGGAAUCAG UGAAUGCUUA UACAUCCGCN          30

(2) INFORMATION FOR SEQ ID NO: 69:

(i) SEQUENCE CHARACTERISTICS:
        (A) LENGTH:  27
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-fluoro
            (2'-F) modified (xi) SEQUENCE DESCRIPTION:  SEQ ID NO: 69:

CGGAAUCAGU GAAUGCUUAU ACAUCCG          27

(2) INFORMATION FOR SEQ ID NO: 70:

(i) SEQUENCE CHARACTERISTICS:
        (A) LENGTH:  25
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are
            2'-fluoro (2'-F) modified (ix) FEATURE:
        (D) OTHER INFORMATION:  C in position 25 is 2'-OH C (xi) SEQUENCE DESCRIPTION:  SEQ ID NO: 70:

GGAAUCAGUG AAUGCUUAUA CAUCC          25

(2) INFORMATION FOR SEQ ID NO: 71:

(i) SEQUENCE CHARACTERISTICS:
        (A) LENGTH:  24
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are -continued 2'-fluoro (2'-F) modified (ix) FEATURE:
         (D) OTHER INFORMATION: N at position 24 is a
             3'-3'-linked deoxythymidine (xi) SEQUENCE DESCRIPTION: SEQ ID NO: 71:

GAAUCAGUGA AUGCUUAUAC AUCN                                           24

(2) INFORMATION FOR SEQ ID NO: 72:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All pyrimidines are
             2'-fluoro (2'-F) modified (ix) FEATURE:
         (D) OTHER INFORMATION: N at position 22 is a
             3'-3'-linked deoxythymidine (xi) SEQUENCE DESCRIPTION: SEQ ID NO: 72:

AAUCAGUGAA UGCUUAUACA UN                                             22

(2) INFORMATION FOR SEQ ID NO: 73:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All pyrimidines are 2'-fluoro
             (2'-F) modified (ix) FEATURE:
         (D) OTHER INFORMATION: N at position 20 is a
             3'-3'-linked deoxythymidine (xi) SEQUENCE DESCRIPTION: SEQ ID NO: 73:

AUCAGUGAAU GCUUAUACAN                                                20

(2) INFORMATION FOR SEQ ID NO: 74:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All pyrimidines are
             2'-fluoro (2'-F) modified (ix) FEATURE:
         (D) OTHER INFORMATION: Purines are 2'-OMethyl
             (2'-OMe) modified (ix) FEATURE:
         (D) OTHER INFORMATION: G in position 10, A in position 12, and G in position 22 are unmodified (i.e., 2'-OH)

(xi) SEQUENCE DESCRIPTION: SEQ ID NO: 74:

GACGAUGCGG UAGGAAGAAU UGGAAGCGC                        29

(2) INFORMATION FOR SEQ ID NO: 75:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (ix) FEATURE:
        (D) OTHER INFORMATION: Purines are 2'-OMethyl
            (2'-OMe) modified (ix) FEATURE:
        (D) OTHER INFORMATION: G in position 10 and A in
            position 12 are unmodified (i.e., 2'-OH)

(xi) SEQUENCE DESCRIPTION: SEQ ID NO: 75:

GACGAUGCGG UAGGAAGAAU UGGAAGCGC                        29

(2) INFORMATION FOR SEQ ID NO: 76:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are
            2'-fluoro (2'-F) modified (ix) FEATURE:
        (D) OTHER INFORMATION: Purines are 2'-OMethyl
            (2'-OMe) modified (ix) FEATURE:
        (D) OTHER INFORMATION: G in positions 10 and 22
            is unmodified (i.e., 2'-OH)

(xi) SEQUENCE DESCRIPTION: SEQ ID NO: 76:

GACGAUGCGG UAGGAAGAAU UGGAAGCGC                        29

(2) INFORMATION FOR SEQ ID NO:77:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro
            (2'-F) modified (ix) FEATURE:
        (D) OTHER INFORMATION: Purines are 2'-OMethyl -continued

```
            (2'-OMe) modified (ix) FEATURE:
        (D) OTHER INFORMATION: A in position 12 and G in
            position 22 are unmodified (i.e., 2'-OH)

(xi) SEQUENCE DESCRIPTION: SEQ ID NO: 77:

GACGAUGCGG UAGGAAGAAU UGGAAGCGC                                29

(2) INFORMATION FOR SEQ ID NO: 78:

(i) SEQUENCE CHARACTERISTICS:
       (A) LENGTH: 31
       (B) TYPE: nucleic acid
       (C) STRANDEDNESS: single
       (D) TOPOLOGY: linear (ii) MOLECULE TYPE: RNA (ix) FEATURE:
        (D) OTHER INFORMATION: All pyrimidines are 2'-fluoro
            (2'-F) modified (ix) FEATURE:
        (D) OTHER INFORMATION: Purines are 2'-OMethyl (2'-OMe)
            modified (ix) FEATURE:
        (D) OTHER INFORMATION: A in position 6 and G in
            position 21 are unmodified (i.e., 2'-OH)

(xi) SEQUENCE DESCRIPTION: SEQ ID NO: 78:

GGCGAACCGA UGGAAUUUUU GGACGCUCGC C                             31

(2) INFORMATION FOR SEQ ID NO: 79:

(i) SEQUENCE CHARACTERISTICS:
       (A) LENGTH: 31
       (B) TYPE: nucleic acid
       (C) STRANDEDNESS: single
       (D) TOPOLOGY: linear (ii) MOLECULE TYPE: RNA (ix) FEATURE:
        (D) OTHER INFORMATION: All pyrimidines are 2'-fluoro
            (2'-F) modified (ix) FEATURE:
        (D) OTHER INFORMATION: Purines are 2'-OMethyl (2'-OMe)
            modified (ix) FEATURE:
        (D) OTHER INFORMATION: A in position 6 is unmodified
            (i.e., 2'-OH)

(xi) SEQUENCE DESCRIPTION: SEQ ID NO: 79:

GGCGAACCGA UGGAAUUUUU GGACGCUCGC C                             31

(2) INFORMATION FOR SEQ ID NO: 80:

(i) SEQUENCE CHARACTERISTICS:
       (A) LENGTH: 31
       (B) TYPE: nucleic acid
       (C) STRANDEDNESS: single
       (D) TOPOLOGY: linear (ii) MOLECULE TYPE: RNA (ix) FEATURE:
        (D) OTHER INFORMATION: All pyrimidines are 2'-fluoro
```

-continued

```
            (2'-F) modified (ix) FEATURE:
         (D) OTHER INFORMATION: Purines are 2'-OMethyl (2'-OMe)
             modified (ix) FEATURE:
         (D) OTHER INFORMATION: G in position 21 is unmodified
             (i.e., 2'-OH)

(xi) SEQUENCE DESCRIPTION: SEQ ID NO: 80:

GGCGAACCGA UGGAAUUUUU GGACGCUCGC C                                      31

(2) INFORMATION FOR SEQ ID NO: 81:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All pyrimidines are
             2'-fluoro (2'-F) modified (ix) FEATURE:
         (D) OTHER INFORMATION: Purines are 2'-OMethyl
             (2'-OMe) modified (ix) FEATURE:
         (D) OTHER INFORMATION: A in positions 5 and 6
             is unmodified (i.e., 2'-OH)

(xi) SEQUENCE DESCRIPTION: SEQ ID NO: 81:

GCGGAAUCAG UGAAUGCUUA UACAUCCGC                                         29

(2) INFORMATION FOR SEQ ID NO:82:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All pyrimidines are
             2'-fluoro (2'-F) modified (ix) FEATURE:
         (D) OTHER INFORMATION: Purines are 2'-OMethyl
             (2'-OMe) modified (ix) FEATURE:
         (D) OTHER INFORMATION: A in position 5 is
             unmodified (i.e., 2'-OH)

(xi) SEQUENCE DESCRIPTION: SEQ ID NO: 82:

GCGGAAUCAG UGAAUGCUUA UACAUCCGC                                         29

(2) INFORMATION FOR SEQ ID NO: 83:

(i) SEQUENCE CHARACTERISTICS:
        (A) LENGTH: 29
        (B) TYPE: nucleic acid
        (C) STRANDEDNESS: single
        (D) TOPOLOGY: linear
```

```
        (ii) MOLECULE TYPE: RNA (ix) FEATURE:
              (D) OTHER INFORMATION: All pyrimidines are
                  2'-fluoro (2'-F) modified (ix) FEATURE:
              (D) OTHER INFORMATION: Purines are 2'-OMethyl
                  (2'-OMe) modified (ix) FEATURE:
              (D) OTHER INFORMATION: A in position 6 is
                  unmodified (i.e., 2'-OH)

(xi) SEQUENCE DESCRIPTION: SEQ ID NO: 83:

GCGGAAUCAG UGAAUGCUUA UACAUCCGC                                               29

(2) INFORMATION FOR SEQ ID NO: 84:

(i) SEQUENCE CHARACTERISTICS:
              (A) LENGTH: 23
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are
                  2'-fluoro (2'-F) modified (ix) FEATURE:
              (D) OTHER INFORMATION: Purines are 2'-OMethyl
                  (2'-OMe) modified (ix) FEATURE:
              (D) OTHER INFORMATION: G in position 4 and A
                  in position 6 are unmodified (i.e., 2'-OH)

(xi) SEQUENCE DESCRIPTION: SEQ ID NO: 84:

GCGGUAGGAA GAAUUGGAAG CGC                                                     23

(2) INFORMATION FOR SEQ ID NO: 85:

(i) SEQUENCE CHARACTERISTICS:
              (A) LENGTH: 29
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are
                  2'-fluoro (2'-F) modified (ix) FEATURE:
              (D) OTHER INFORMATION: Purines are 2'-OMethyl
                  (2'-OMe) modified (ix) FEATURE:
              (D) OTHER INFORMATION: A in position 5 and G
                  in position 20 are unmodified (i.e., 2'-OH)

(xi) SEQUENCE DESCRIPTION: SEQ ID NO: 85:

GCGAACCGAU GGAAUUUUUG GACGCUCGC                                               29

(2) INFORMATION FOR SEQ ID NO: 86:

(i) SEQUENCE CHARACTERISTICS:
              (A) LENGTH: 27
```

-continued

```
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are
                2'-fluoro (2'-F) modified (ix) FEATURE:
            (D) OTHER INFORMATION:  Purines are 2'-OMethyl
                (2'-OMe) modified (ix) FEATURE:
            (D) OTHER INFORMATION:  A in positions 4 and 5
                is unmodified (i.e., 2'-OH)

(xi) SEQUENCE DESCRIPTION:  SEQ ID NO: 86:

CGGAAUCAGU GAAUGCUUAU ACAUCCG                                         27

(2) INFORMATION FOR SEQ ID NO: 87:

(i) SEQUENCE CHARACTERISTICS:
            (A) LENGTH:  13
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:

(xi) SEQUENCE DESCRIPTION:  SEQ ID NO: 87:

GCCTTAGTCA CTT                                                        13

(2) INFORMATION FOR SEQ ID NO: 88:

(i) SEQUENCE CHARACTERISTICS:
            (A) LENGTH:  14
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:

(xi) SEQUENCE DESCRIPTION:  SEQ ID NO: 88:

CGGATGTATA AGCA                                                       14
```

VASCULAR ENDOTHELIAL GROWTH FACTOR (VEGF) NUCLEIC ACID LIGAND COMPLEXES

This application is a Continuation-in-Part of U.S. patent application Ser. No. 08/870,930, entitled Vascular Endothelial Growth Factor (VEGF) Nucleic Acid Ligand Complexes, filed Jun. 6, 1997.

FIELD OF THE INVENTION

Described herein are high affinity 2' Fluoro (2'-F) pyrimidine RNA ligands to vascular endothelial growth factor (VEGF). The method utilized herein for identifying such Nucleic Acid Ligands is called SELEX, an acronym for Systematic Evolution of Ligands by Exponential enrichment. Further included in this invention is a method for preparing a therapeutic or diagnostic Complex comprised of a VEGF Nucleic Acid Ligand and a Non-Immunogenic, High Molecular Weight Compound or a Lipophilic Compound by identifying a VEGF Nucleic Acid Ligand by SELEX methodology and covalently linking the VEGF Nucleic Acid Ligand with a Non-Immunogenic, High Molecular Weight Compound or a Lipophilic Compound. The invention further includes Complexes comprised of one or more VEGF Nucleic Acid Ligands and a Non-Immunogenic, High Molecular Weight Compound or a Lipophilic Compound. The invention further relates to improving the Pharmacokinetic Properties of a VEGF Nucleic Acid Ligand by covalently linking the VEGF Nucleic Acid Ligand with a Non-Immunogenic, High Molecular Weight Compound or Lipophilic Compound to form a Complex. The invention further relates to improving the Pharmacokinetic Properties of a VEGF Nucleic Acid Ligand by using a Lipid Construct comprising a VEGF Nucleic Acid Ligand or a Complex comprising a VEGF Nucleic Acid Ligand and a Non-Immunogenic, High Molecular Weight Compound or Lipophilic Compound. This invention further relates to a method for targeting a therapeutic or diagnostic agent to a biological target that is expressing VEGF by associating the agent with a Complex comprised of a VEGF Nucleic Acid Ligand and a Lipophilic Compound or Non-Immunogenic, High Molecular Weight Compound, wherein the Complex is further associated with a Lipid Construct and the VEGF Nucleic Acid Ligand is further associated with the exterior of the Lipid Construct.

BACKGROUND OF THE INVENTION

A. SELEX

The dogma for many years was that nucleic acids had primarily an informational role. Through a method known as Systematic Evolution of Ligands by EXponential enrichment, termed SELEX, it has become clear that nucleic acids have three dimensional structural diversity not unlike proteins. SELEX is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096, U.S. patent application Ser. No. 07/931,473, filed Aug. 17, 1992, entitled "Method for Identifying Nucleic Acid Ligands," now U.S. Pat. No. 5,270,163 (see also WO 91/19813), each of which is specifically incorporated by reference herein. Each of these applications, collectively referred to herein as the SELEX Patent Applications, describes a fundamentally novel method for making a Nucleic Acid Ligand to any desired target molecule. The SELEX process provides a class of products which are referred to as Nucleic Acid Ligands, each ligand having a unique sequence, and which has the property of binding specifically to a desired target compound or molecule. Each SELEX-identified Nucleic Acid Ligand is a specific ligand of a given target compound or molecule. SELEX is based on the unique insight that Nucleic Acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the target under conditions favorable for binding, partitioning unbound Nucleic Acids from those Nucleic Acids which have bound specifically to target molecules, dissociating the Nucleic Acid-target complexes, amplifying the Nucleic Acids dissociated from the Nucleic Acid-target complexes to yield a ligand-enriched mixture of Nucleic Acids, then reiterating the steps of binding, partitioning, dissociating and amplifying through as many cycles as desired to yield highly specific high affinity Nucleic Acid Ligands to the target molecule.

It has been recognized by the present inventors that the SELEX method demonstrates that Nucleic Acids as chemical compounds can form a wide array of shapes, sizes and configurations, and are capable of a far broader repertoire of binding and other functions than those displayed by Nucleic Acids in biological systems.

The present inventors have recognized that SELEX or SELEX-like processes could be used to identify Nucleic Acids which can facilitate any chosen reaction in a manner similar to that in which Nucleic Acid Ligands can be identified for any given target. In theory, within a Candidate Mixture of approximately $10^{13}$ to $10^{18}$ Nucleic Acids, the present inventors postulate that at least one Nucleic Acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," abandoned in favor of U.S. patent application Ser. No. 08/198,670, now U.S. Pat. No. 5,707,796, describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting Nucleic Acid Ligands containing photoreactive groups capable of binding and/or photo-crosslinking to and/or photoinactivatinga target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443, 957, now U.S. Pat. No. 5,580,737, describes a method for identifying highly specific Nucleic Acid Ligands able to discriminate between closely related molecules, which can be non-peptidic, termed Counter-SELEX. U.S. patent application Ser. No. 08/143,564, filed Oct. 25, 1993, entitled "Systematic Evolution of Ligands by EXponential Enrichment: Solution SELEX," now U.S. Pat. No. 5,567,588, describes a SELEX-based method which achieves highly efficient partitioning between oligonucleotide shaving high and low affinity for a target molecule.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of known and novel 2'-Modified nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,489 and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected Nucleic Acid Ligands with Lipophilic Compounds or Non-Immunogenic, High Molecular Weight Compounds in a diagnostic or therapeutic Complex as described in U.S. patent application Ser. No. 08/434,465, filed May 4, 1995, entitled "Nucleic Acid Complexes." VEGF Nucleic Acid Ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes.", now U.S. Pat. No. 5,859,228. Each of the above described patent applications which describe modifications of the basic SELEX procedure are specifically incorporated by reference herein in their entirety.

B. Lipid Constructs

Lipid Bilayer Vesicles are closed, fluid-filled microscopic spheres which are formed principally from individual molecules having polar (hydrophilic) and non-polar (lipophilic) portions. The hydrophilic portions may comprise phosphate, glycerylphosphato, carboxy, sulfato, amino, hydroxy, choline or other polar groups. Examples of lipophilic groups are saturated or unsaturated hydrocarbons such as alkyl, alkenyl or other lipid groups. Sterols (e.g., cholesterol) and other pharmaceutically acceptable adjuvants (including antioxidants like alpha-tocopherol) may also be included to improve vesicle stability or confer other desirable characteristics.

Liposomes are a subset of these bilayer vesicles and are comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space. These multilamellar vesicles (MLV) can be converted into small or Unilamellar Vesicles (UV), with the application of a shearing force.

The therapeutic use of liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies or specific receptor ligands to the surface of the liposomes. Antibodies are known to have a high specificity for their corresponding antigen and have been attached to the surface of liposomes, but the results have been less than successful in many instances. Some efforts, however, have been successful in targeting liposomes to tumors without the use of antibodies, see, for example, U.S. Pat. No. 5,019,369, U.S. Pat. Nos. 5,441,745, or 5,435,989.

An area of development aggressively pursued by researchers is the delivery of agents not only to a specific cell type but into the cell's cytoplasm and, further yet, into the nucleus. This is particularly important for the delivery of biological agents such as DNA, RNA, ribozymes and proteins. A promising therapeutic pursuit in this area involves the use of antisense DNA and RNA oligonucleotides for the treatment of disease. However, one major problem encountered in the effective application of antisense technology is that oligonucleotides in their phosphodiester form are quickly degraded in body fluids and by intracellular and extracellular enzymes, such as endonucleases and exonucleases, before the target cell is reached. Intravenous administration also results in rapid clearance from the bloodstream by the kidney, and uptake is insufficient to produce an effective intracellular drug concentration. Liposome encapsulation protects the oligonucleotides from the degradative enzymes, increases the circulation half-life and increases uptake efficiency as a result of phagocytosis of the Liposomes. In this way, oligonucleotides are able to reach their desired target and to be delivered to cells in vivo.

A few instances have been reported where researchers have attached antisense oligonucleotides to Lipophilic Compounds or Non-Immunogenic, High Molecular Weight Compounds. Antisense oligonucleotides, however, are only effective as intracellular agents. Antisense oligodeoxyribonucleotides targeted to the epidermal growth factor (EGF) receptor have been encapsulated into Liposomes linked to folate via a polyethylene glycol spacer (folate-PEG-Liposomes) and delivered into cultured KB cells via folate receptor-mediated endocytosis (Wang et al. (1995) Proc. Natl. Acad. Sci. USA 92:3318–3322). In addition, a Lipophilic Compound covalently attached to an antisense oligonucleotide has been demonstrated in the literature (EP 462 145 B 1).

C. VEGF

The growth of new blood vessels from existing endothelium (angiogenesis) is tightly controlled in healthy adults by opposing effects of positive and negative regulators. Under certain pathological conditions, including proliferative retinopathies, rheumatoid arthritis, psoriasis and cancer, positive regulators prevail and angiogenesis contributes to disease progression (reviewed in Folkman (1995) Nature Medicine 1:27–31). In cancer, the notion that angiogenesis represents the rate limiting step of tumor growth and metastasis (Folkman (1971) New Engl. J. Med. 285:1182–1186) is now supported by considerable experimental evidence (reviewed in Aznavoorian et al. (1993) Cancer 71:1368–1383; Fidler and Ellis (1994) Cell 79:185–188; Folkman (1990) J. Natl. Cancer Inst. 82:4–6).

The quantity of blood vessels in tumor tissue is a strong negative prognostic indicator in breast cancer (Weidner et al. (1992) J. Natl. Cancer Inst. 84:1875–1887), prostate cancer (Weidner et al. (1993) Am. J. Pathol. 143:401–409), brain tumors (Li et al.(1994) Lancet 344:82–86), and melanoma (Foss et al.(1996) Cancer Res. 56:2900–2903).

A number of angiogenic growth factors have been described to date among which vascular endothelial growth factor (VEGF) appears to play a key role as a positive regulator of physiological and pathological angiogenesis (reviewed in Brown et al.(1 996) Control of Angiogenesis (Goldberg and Rosen, eds.) Birkhauser, Basel, in press; Thomas (1996) J.

Biol. Chem. 271:603–606). VEGF is a secreted disulfide-linkedhomodimerthat selectively stimulates endothelial cells to proliferate, migrate, and produce matrix-degrading enzymes (Conn et al.(1 990) Proc. Natl. Acad. Sci. USA 87:1323–1327); Ferrara and Henzel (1989) Biochem. Biophys. Res. Commun. 161 :851–858);Gospodarowiczet al. (1989) Proc. Natl. Acad. Sci. USA 7311–7315); Pepper et al. (1991) Biochem. Biophys. Res. Commun. 181:902–906; Unemori et al.(1992) J. Cell. Physiol. 153:557–562), all of which are processes required for the formation of new vessels. In addition to being the only known endothelial cell specific mitogen, VEGF is unique among angiogenic growth factors in its ability to induce a transient increase in blood vessel permeability to macromolecules (hence its original and alternative name, vascular permeability factor, VPF) (Dvorak et al.(1979) J. Immunol. 122:166–174; Senger et al.( 1983) Science 219:983–985; Senger et al.(1986) Cancer Res. 46:5629–5632). Increased vascular permeability and the resulting deposition of plasma proteins in the extravascular space assists the new vessel formation by providing a provisional matrix for the migration of endothelial cells (Dvorak et al.(11995) Am. J. Pathol. 146:1029–1039). Hyperpermeability is indeed a characteristic feature of new vessels, including those associated with tumors (Dvorak et al.(1995) Am. J. Pathol. 146:1029–1039). Furthermore, compensatory angiogenesis induced by tissue hypoxia is now known to be mediated by VEGF (Levy et al.(1996) J. Biol. Chem. 2746–2753); Shweiki et al. (1992) Nature 359:843–845).

VEGF occurs in four forms (VEGF-121, VEGF-165, VEGF-189, VEGF-206) as a result of alternative splicing of the VEGF gene (Houck et al. (1991) Mol. Endocrin. 5:1806–1814; Tischeret al. (1991) J. Biol. Chem. 266:11947–11954). The two smaller forms are diffusable while the larger two forms remain predominantly localized to the cell membrane as a consequence of their high affinity for heparin. VEGF-165 also binds to heparin and is the most abundant form. VEGF-121, the only form that does not bind to heparin, appears to have a lower affinity for the receptors (Gitay-Goren et al. (1996) J. Biol. Chem. 271:5519–5523) as well as lower mitogenic potency (Keyt et al. (1996) J. Biol. Chem. 271:7788–7795). The biological effects of VEGF are mediated by two tyrosine kinase receptors (Flt-1 and Flk-1/KDR) whose expression is highly restricted to cells of endothelial origin (de Vries et al. (1992) Science 255:989–991; Millauer et al. (1993) Cell 72:835–846; Terman et al. (1991) Oncogene 6:519–524). While the expression of both functional receptors is required for high affinity binding, the chemotactic and mitogenic signaling in endothelial cells appears to occur primarily through the KDR receptor (Park et al. (1994) J. Biol. Chem. 269:25646–25654; Seetharam et al. (1995) Oncogene 10:135–147; Waltenbergeret al. (1994) J. Biol. Chem. 26988–26995). The importance of VEGF and VEGF receptors for the development of blood vessels has recently been demonstrated in mice lacking a single allele for the VEGF gene (Carmeliet et al. (1996) Nature 380:435–439; Ferrara et al. (1996) Nature 380:439–442) or both alleles of the Flt-1 (Fong et al. (1995) 376:66–70) or Flk-1 genes (Shalaby et al. (1995) Nature 376:62–66). In each case, distinct abnormalities in vessel formation were observed resulting in embryonic lethality.

VEGF is produced and secreted in varying amounts by virtually all tumor cells (Brown et al. (1997) Regulation of Angiogenesis (Goldberg and Rosen, Eds.) Birkhauser, Basel, pp. 233–269). Direct evidence that VEGF and its receptors contribute to tumor growth was recently obtained by a demonstration that the growth of human tumor xenografts in nude mice could be inhibited by neutralizing antibodies to VEGF (Kim et al. (1993) Nature 362:841–844), by the expression of dominant-negativeVEGF receptor flk-1 (Millauer et al. (1996) Cancer Res. 56:1615–1620; Millauer et al. (1994) Nature 367:576–579), by low molecular weight inhibitors of Flk-1 tyrosine kinase activity (Strawn et al. (1966) Cancer Res. 56:3540–3545), or by the expression of antisense sequence to VEGF mRNA (Salch et al. (1996) Cancer Res. 56:393–401). Importantly, the incidence of tumor metastases was also found to be dramatically reduced by VEGF antagonists (Claffey et al. (1996) Cancer Res. 56:172–181).

VEGF inhibitors may have broad clinical utility due to the role of VFGF in a wide variety of diseases including psoriasis, ocular disorders, collagen vasuclar diseases and neoplastic diseases. Although most tumor types are known to produce VEGF, until recently none has been shown to express functional VEGF receptors. It has been shown that Kaposi's sarcoma (KS) cells not only produce abundant amounts of VEGF but also express functional VEGF receptors and therefore use VEGF for autocrine growth. Kaposi's sarcoma is typically treated with conventional antimetabolic drugs. However, a major shortcoming of the use of chemotherapy in KS patients is the accompanying induction of immunosuppression which has serious consequences in patients whose immune system is already compromised. The need for alternative therapies is especially great in early stages of the disease where KS lesions begin to appear but the patients otherwise feel fairly healthy. In this regard, encapsulation of chemotherapeutic drugs such as daunorubicin into liposomes has recently proved to be a promising method of minimizing side effects of chemotherapy while maintaining anti-tumor efficacy. Drugs with low toxicity that selectively target activated cells of endothelial origin, such as the Nucleic Acid Ligand VEGF antagonists described here, would be an enormous asset in the treatment of KS.

Other areas of potential clinical utility for the VEGF nucleic acid ligands are ocular disorders characterized by excessive angiogenesis. An example of such a disease is macular degeneration. In macular degeneration, progressive choroidal angiogenesis beneath the macula (a part of the retina responsible for the highest visual acuity) interferes with vision. While the initial stimuli that initiate blood vessel growth in macular degeneration are not known at present, VEGF appears to be a key angiogenesis inducer (Lopez, P. F. et al. (1996) Invest. Ophthalmol. Visual Science 37, 855–868, Kliffen, M. et al. (1997) Br. J. Ophthalmol. 81, 154–162; Kvanta, A. et al. (1996) Invest. Ophthalmol. Visual Science 37, 1929–1934). Inhibitors of VEGF therefore may be useful in attenuating angiogenesis in macular degeneration.

SUMMARY OF THE INVENTION

Described herein are high affinity 2' Fluoro (2'-F)-modified pyrimidine RNA ligands to vascular endothelial growth factor (VEGF). The method utilized herein for identifying such nucleic acid ligands is called SELEX, an acronym for Systematic Evolution of Ligands by Exponential enrichment. The ligands described herein were selected from an initial pool of about $10^{14}$ RNA molecules randomized at 30 or 40 contiguous positions. Included herein are the evolved ligands that are shown in Tables 1–4.

Further included in this invention is a method for preparing a Complex comprised of a VEGF Nucleic Acid Ligand and a Non-Immunogenic, High Molecular Weight Compound or Lipophilic Compound by the method comprising identifying a Nucleic Acid Ligand from a Candidate Mixture of Nucleic Acids where the Nucleic Acid is a ligand of VEGF by the method of (a) contacting the Candidate Mixture of Nucleic Acids with VEGF, (b) partitioning between members of said Candidate Mixture on the basis of affinity to VEGF, and c) amplifying the selected molecules to yield a mixture of Nucleic Acids enriched for Nucleic Acid sequences with a relatively higher affinity for binding to VEGF, and covalently linking said identified VEGF Nucleic Acid Ligand with a Non-Immunogenic, High Molecular Weight Compound or a Lipophilic Compound. The invention further comprises a Complex comprised of a VEGF Nucleic Acid Ligand and a Non-Immunogenic, High Molecular Weight Compound or a Lipophilic Compound.

The invention further includes a Lipid Construct comprising a VEGF Nucleic Acid Ligand or a Complex. The present invention further relates to a method for preparing a Lipid Construct comprising a Complex wherein the Complex is comprised of a VEGF Nucleic Acid Ligand and a Lipophilic Compound.

In another embodiment, this invention provides a method for improving the pharmacokinetic properties of a VEGF Nucleic Acid Ligand by covalently linking the VEGF Nucleic Acid Ligand with a Non-Immunogenic, High Molecular Weight Compound or Lipophilic Compound to form a Complex and administering the Complex to a patient. The invention further relates to a method for improving the pharmacokinetic properties of a VEGF Nucleic Acid Ligand by further associating the Complex with a Lipid Construct.

It is an object of the present invention to provide Complexes comprising one or more VEGF Nucleic Acid Ligands in association with one or more Non-Immunogenic, High Molecular Weight Compounds or Lipophilic Compounds and methods for producing the same. It is a further object of the present invention to provide Lipid Constructs comprising a Complex. It is a further object of the invention to provide one or more VEGF Nucleic Acid Ligands in association with one or more Non-Immunogenic, High Molecular Weight Compounds or Lipophilic Compounds with improved Pharmacokinetic Properties.

In embodiments of the invention directed to Complexes comprised of a VEGF Nucleic Acid Ligand and a Non-Immunogenic, High Molecular Weight Compound, it is preferred that the Non-Immunogenic, High Molecular Weight Compound is Polyalkylene Glycol, more preferably, polyethylene glycol (PEG). More preferably, the PEG has a molecular weight of about 10–80K. Most preferably, the PEG has a molecular weight of about 20–45K. In embodiments of the invention directed to Complexes comprised of a VEGF Nucleic Acid Ligand and a Lipophilic Compound, it is preferred that the Lipophilic Compound is a glycerolipid, phospholipid, or glycerol amide lipid. In the preferred embodiments of the invention, the Lipid Construct is preferably a Lipid Bilayer Vesicle and most preferably a Liposome. In the preferred embodiment, the VEGF Nucleic Acid Ligand is identified according to the SELEX method.

In embodiments of the invention directed to Complexes comprising a Non-Immunogenic, High Molecular Weight Compound or Lipophilic Compound covalently linked to a VEGF Nucleic Acid Ligand or Ligands, the VEGF Nucleic Acid Ligand or Ligands can serve in a targeting capacity.

Additionally, the VEGF Nucleic Acid Ligand can be associated through Covalent or Non-Covalent Interactions with a Lipid Construct without being part of a Complex.

Furthermore, in embodiments of the invention directed to Lipid Constructs comprising a VEGF Nucleic Acid Ligand or a Non-Immunogenic, High Molecular Weight or Lipophilic Compound/VEGF Nucleic Acid Ligand Complex where the Lipid Construct is of a type that has a membrane defining an interior compartment such as a Lipid Bilayer Vesicle, the VEGF Nucleic Acid Ligand or Complex in association with the Lipid Construct may be associated with the membrane of the Lipid Construct or encapsulated within the compartment. In embodiments where the VEGF Nucleic Acid Ligand is in association with the membrane, the VEGF Nucleic Acid Ligand can associate with the interior-facing or exterior-facing part of the membrane, such that the VEGF Nucleic Acid Ligand is projecting into or out of the vesicle. In embodiments where the Nucleic Acid Ligand is projecting out of the Lipid Construct, the VEGF Nucleic Acid Ligand can serve in a targeting capacity.

In embodiments where the VEGF Nucleic Acid Ligand of the Lipid Construct serves in a targeting capacity, the Lipid Construct can have associated with it additional therapeutic or diagnostic agents. In one embodiment, the therapeutic or diagnostic agent is associated with the exterior of the Lipid Construct. In other embodiments, the therapeutic or diagnostic agent is encapsulated in the Lipid Construct or associated with the interior of the Lipid Construct. In yet a further embodiment, the therapeutic or diagnostic agent is associated with the Complex. In one embodiment, the therapeutic agent is a drug. In an alternative embodiment, the therapeutic or diagnostic agent is one or more additional Nucleic Acid Ligands.

It is a further object of the present invention to provide a method for inhibiting angiogenesis by the administration of a VEGF Nucleic Acid Ligand or a Complex comprising a VEGF Nucleic Acid Ligand and Non-Immunogenic, High Molecular Weight Compound or Lipophilic Compound or a Lipid Construct comprising the Complex of the present invention. It is yet a further object of the present invention to provide a method for inhibiting the growth of tumors by the administration of a VEGF Nucleic Acid Ligand or Complex comprising a VEGF Nucleic Acid Ligand and Non-Immunogenic, High Molecular Weight Compound or Lipophilic Compound or a Lipid Construct comprising a Complex of the present invention. It is yet a further object of the invention to provide a method for inhibiting Kaposi's Sarcoma by the administration of a VEGF Nucleic Acid Ligand or Complex comprising a VEGF Nucleic Acid Ligand and Non-Immunogenic, High Molecular Weight Compound or Lipophilic Compound or a Lipid Construct comprising a Complex of the present invention. It is yet a further object of the invention to provide a method for inhibiting macular degeneration by the administration of a VEGF Nucleic Acid Ligand or Complex comprising a VEGF Nucleic Acid Ligand and Non-Immunogenic, High Molecular Weight Compound or Lipophilic Compound or a Lipid Construct comprising a Complex of the present invention.

It is a further object of the invention to provide a method for targeting a therapeutic or diagnostic agent to a biological target that is expressing VEGF by associating the agent with a Complex comprised of a VEGF Nucleic Acid Ligand and a Lipophilic Compound or Non-Immunogenic, High Molecular Weight Compound, wherein the Complex is further associated with a Lipid Construct and the VEGF Nucleic Acid Ligand is further associated with the exterior of the Lipid Construct.

These and other objects, as well as the nature, scope and utilization of this invention, will become readily apparent to those skilled in the art from the following description and the appended claims.

BRIEF DESCRIPTION OF THE FIGURES

FIGS. 1A–1I show the molecular descriptions of NX31838-PL (FIG. 1A), NX31838 Lipid Amide 1 (FIG. 1B), NX31838 Lipid Amide 2 (FIG. 1C), NX31838-40K mPEG (FIG. 1D), NX31838-20K mPEG (FIG. 1E), C-5 Aminolinker (FIG. 1F), Glycerol Bisphosphate Linker (FIG. 1G), 18 Atom Spacer Linker (FIG. 1H), and 3'3' dT (FIG. 1I). The 5' phosphate group of the ligand is depicted in the figures. mPEG stands for methyl polyethylene glycol. A lower case letter preceding a nucleotide indicates the following: m=2'-O-Methyl, a=2'-amino, r=ribo, and f=2'-fluoro. No letter preceding a nucleotide indicates a deoxyribonucleotide (2'H). 3'3'-dT indicates a 3'3' inverted phosphodiester linkage at the 3' end.

DETAILED DESCRIPTION OF THE INVENTION

Figure 1A:
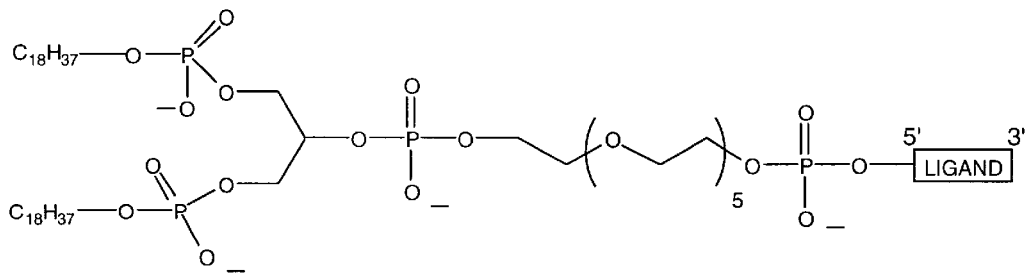
Figure 1B:
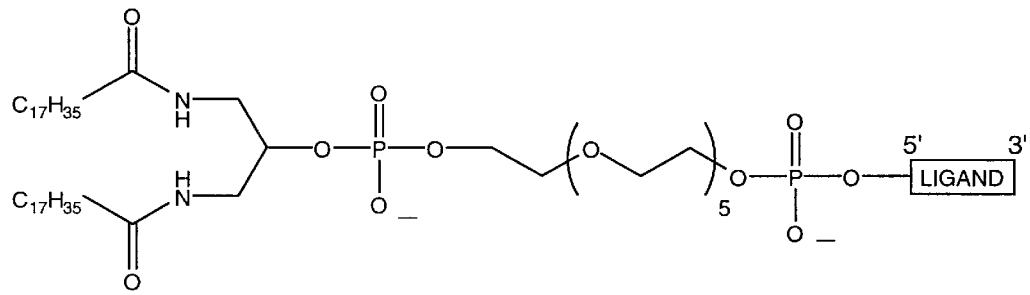

Definitions:

"Covalent Bond" is the chemical bond formed by the sharing of electrons.

"Non-Covalent Interactions" are means by which molecular entities are held together by interactions other than Covalent Bonds including ionic interactions and hydrogen bonds.

"Lipophilic Compounds" are compounds which have the propensity to associate with or partition into lipid and/or other materials or phases with low dielectric constants, including structures that are comprised substantially of lipophilic components. Lipophilic Compounds include lipids as well as non-lipid containing compounds that have the propensity to associate with lipid (and/or other materials or phases with low dielectric constants). Cholesterol, phospholipids, and glycerolipids, such as dialkylglycerol, and diacylglycerol, and glycerol amide lipids are further examples of Lipophilic Compounds. In one preferred embodiment of the invention, the lipophilic compound covalently linked to the VEGF Nucleic Acid Ligand is a glycerolipid having has the structure

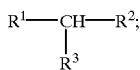

where $R^1$, $R^2$, and $R^3$ are independently selected from the group consisting of $CH_3(CH_2)_n$—$O(PO_3)$—$CH_2$—; and $CH_3(CH_2)_n$—$CONH_2$—$CH_2$—, and —OX—, wherein at least one must be —OX—, X is independently selected from the group consisting of $(PO_3)$ and O, and wherein n=0–30, preferably 10–20. When R is $CH_3(CH_2)_n$—$O(PO_3)$—$CH_2$—, the Lipophilic Compound is a phospholipid. When R is $CH_3(CH_2)_n$—$CONH_2$—$CH_2$—, the Lipophilic Compound is a glycerol amide lipid. In a preferred embodiment, $R^3$ is —OX—.

"Complex" as used herein describes the molecular entity formed by the covalent linking of a VEGF Nucleic Acid Ligand to a Non-Immunogenic, High Molecular Weight Compound or Lipophilic Compound. In certain embodiments of the present invention, the Complex is depicted as A-B-Y, wherein A is a Lipophilic Compound or Non-Immunogenic, High Molecular Weight Compound as described herein; B is optional, and may be one or more linkers Z; and Y is a VEGF Nucleic Acid Ligand. "Lipid Constructs," for purposes of this invention, are structures containing lipids, phospholipids, or derivatives thereof comprising a variety of different structural arrangements which lipids are known to adopt in aqueous suspension. These structures include, but are not limited to, Lipid Bilayer Vesicles, micelles, Liposomes, emulsions, lipid ribbons or sheets, and may be complexed with a variety of drugs and components which are known to be pharmaceutically acceptable. In the preferred embodiment, the Lipid Construct is a Liposome. The preferred Liposome is unilamellar and has a relative size less than 200 nm. Common additional components in Lipid Constructs include cholesterol and alpha-tocopherol, among others. The Lipid Constructs may be used alone or in any combination which one skilled in the art would appreciate to provide the characteristics desired for a particular application. In addition, the technical aspects of Lipid Constructs and Liposome formation are well known in the art and any of the methods commonly practiced in the field may be used for the present invention.

"Nucleic Acid Ligand" as used herein is a non-naturally occurring Nucleic Acid having a desirable action on a Target. The Target of the present invention is VEGF, hence the term VEGF Nucleic Acid Ligand. A desirable action includes, but is not limited to, binding of the Target, catalytically changing the Target, reacting with the Target in a way which modifies/alters the Target or the functional activity of the Target, covalently attaching to the Target as in a suicide inhibitor, facilitating the reaction between the Target and another molecule. In the preferred embodiment, the action is specific binding affinity for VEGF, wherein the Nucleic Acid Ligand is not a Nucleic Acid having the known physiological function of being bound by VEGF.

In preferred embodiments of the invention, the VEGF Nucleic Acid Ligand of the Complexes and Lipid Constructs of the invention are identified by the SELEX methodology. VEGF Nucleic Acid Ligands are identified from a Candidate Mixture of Nucleic Acids, said Nucleic Acid being a ligand of VEGF, by the method comprising a) contacting the Candidate Mixture with VEGF, wherein Nucleic Acids having an increased affinity to VEGF relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids (see U.S. patent application Ser. No. 08/233,012, filed Apr. 25, 1994, entitled "High Affinity Oligonucleotide Ligands to Vascular Endothelial Growth Factor (VEGF)," now U.S. Pat. No. 5,849,479. U.S. patent application Ser. No. 08/447,169, filed May 19, 1995, entitled "High Affinity Oligonucleotide Ligands to Vascular Endothelial Growth Factor (VEGF)," now U.S. Pat. No. 5,811,533 which are hereby incorporated by reference herein).

"Candidate Mixture" is a mixture of Nucleic Acids of differing sequence from which to select a desired ligand. The source of a Candidate Mixture can be from naturally-occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications such as internucleoside phosphorothioate linkages, methylations, unusual base-pairing combinations such as the isobases isocytidine and isoguanidine and the like. Modifications can also include 3' and 5' modifications such as capping.

"Non-Immunogenic, High Molecular Weight Compound" is a compound between approximately 1000 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. Examples of Non-Immunogenic, High Molecular Weight Compounds include Polyalkylene Glycol and polyethylene glycol. In one preferred embodiment of the invention, the Non-Immunogenic, High Molecular Weight Compound covalently linked to the VEGF Nucleic Acid Ligand is a polyalkylene glycol and has the structure $R(O(CH_2)_x)_nO$—, where R is independently selected from the group consisting of H and $CH_3$, x=2–5, and n≈MW of the Polyalkylene Glycol/16+14x. In the preferred embodiment of the present invention, the molecular weight is about between 10–80 kDa. In the most preferred embodiment, the molecular weight of the polyalkylene glycol is about between 20–45 kDa. In the most preferred embodiment, x=2 and n=9×10². There can be one or more Polyalkylene Glycols attached to the same VEGF Nucleic Acid Ligand, with the sum of the molecular weights preferably being between 10–80 kDa, more preferably 20–45 kDa.

In certain embodiments, the Non-Immunogenic, High Molecular Weight Compound can also be a Nucleic Acid Ligand.

"Lipid Bilayer Vesicles" are closed, fluid-filled microscopic spheres which are formed principally from individual molecules having polar (hydrophilic) and non-polar (lipophilic) portions. The hydrophilic portions may comprise phosphato, glycerylphosphato, carboxy, sulfato, amino, hydroxy, choline and other polar groups. Examples of non-polar groups are saturated or unsaturated hydrocarbons such as alkyl, alkenyl or other lipid groups. Sterols (e.g., cholesterol) and other pharmaceutically acceptable components (including anti-oxidants like alpha-tocopherol) may also be included to improve vesicle stability or confer other desirable characteristics.

"Liposomes" are a subset of Lipid Bilayer Vesicles and are comprised principally of phospholipid molecules which contain two hydrophobic tails consisting of long fatty acid chains. Upon exposure to water, these molecules spontaneously align to form a bilayer membrane with the lipophilic ends of the molecules in each layer associated in the center of the membrane and the opposing polar ends forming the respective inner and outer surface of the bilayer membrane. Thus, each side of the membrane presents a hydrophilic surface while the interior of the membrane comprises a lipophilic medium. These membranes when formed are generally arranged in a system of concentric closed membranes separated by interlamellar aqueous phases, in a manner not dissimilar to the layers of an onion, around an internal aqueous space. These multilamellar vesicles (MLV) can be converted into unilamellar vesicles (UV), with the application of a shearing force.

"Cationic Liposome" is a Liposome that contains lipid components that have an overall positive charge at physiological pH.

"SELEX" methodology involves the combination of selection of Nucleic Acid Ligands which interact with a Target in a desirable manner, for example binding to a protein, with amplification of those selected Nucleic Acids. Iterative cycling of the selection/amplification steps allows selection of one or a small number of Nucleic Acids which interact most strongly with the Target from a pool which contains a very large number of Nucleic Acids. Cycling of the selection/amplification procedure is continued until a selected goal is achieved.

The SELEX methodology is described in the SELEX Patent Applications.

"Target" means any compound or molecule of interest for which a ligand is desired. A Target can be a protein (such as VEGF, thrombin, and selectin), peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. The principal Target of the subject invention is VEGF.

"Improved PharmacokineticProperties" means that the VEGF Nucleic Acid Ligand covalently linked to a Non-Immunogenic, li gh Molecular Weight Compound or Lipophilic Compound or in association with a Lipid Construct shows a longer circulation half-life in vivo relative to the same VEGF Nucleic Acid Ligand not in association with a Non-Immunogenic, High Molecular Weight Compound or Lipophilic Compound or in association with a Lipid Construct.

"Linker" is a molecular entity that connects two or more molecular entities through Covalent Bond or Non-Covalent Interactions, and can allow spatial separation of the molecular entities in a manner that preserves the functional properties of one or more of the molecular entities. A linker can also be known as a spacer. Examples of Linkers, include but are not limited to, the structures shown in FIGS. 1F–1H.

"Therapeutic" as used herein, includes treatment and/or prophylaxis. When used, Therapeutic refers to humans and other animals.

This invention includes RNA ligands to VEGF that are comprised of 2'F-modified nucleotides. This invention further includes the specific RNA ligands to VEGF shown in Tables 1–4 (SEQ ID NOS: 10–86). More specifically, this invention includes nucleic acid sequences that are substantially homologous to and that have substantially the same ability to bind VEGF as the specific nucleic acid ligands shown in Tables 1–4. By substantially homologous it is meant a degree of primary sequence homology in excess of 70%, most preferably in excess of 80%, and even more preferably in excess of 90%, 95%, or 99%. The percentage of homology as described herein is calculated as the percentage of nucleotides found in the smaller of the two sequences which align with identical nucleotide residues in the sequence being compared when I gap in a length of 10 nucleotides may be introduced to assist in that alignment. Substantially the same ability to bind VEGF means that the affinity is within one or two orders of magnitude of the affinity of the ligands described herein. It is well within the skill of those of ordinary skill in the art to determine whether a given sequence—substantially homologous to those specifically described herein—has the same ability to bind VEGF.

A review of the sequence homologies of the nucleic acid ligands of VEGF shown in Tables 1–4 (SEQ ID NOS: 10–86) shows that sequences with little or no primary homology may have substantially the same ability to bind VEGF. For these reasons, this invention also includes Nucleic Acid Ligands that have substantially the same postulated structure or structural motifs and ability to bind VEGF as the nucleic acid ligands shown in Tables 1–4.

Substantially the same structure or structural motifs can be postulated by sequence alignment using the Zukerfold program (see Zuker (1989) Science 244:48–52). As would be known in the art, other computer programs can be used for predicting secondary structure and structural motifs. Substantially the same structure or structural motif of Nucleic Acid Ligands in solution or as a bound structure can also be postulated using NMR or other techniques as would be known in the art.

Further included in this invention is a method for preparing a Complex comprised of a VEGF Nucleic Acid Ligand and a Non-Immunogenic, High Molecular Weight Compound or Lipophilic Compound by the method comprising identifying a Nucleic Acid Ligand from a Candidate Mixture of Nucleic Acids where the Nucleic Acid is a ligand of VEGF by the method of (a) contacting the Candidate Mixture of Nucleic Acids with VEGF, (b) partitioning between members of said Candidate Mixture on the basis of affinity to VEGF, and c) amplifying the selected molecules to yield a mixture of Nucleic Acids enriched for Nucleic Acid sequences with a relatively higher affinity for binding to VEGF, and covalently linking said identified VEGF Nucleic Acid Ligand with a Non-Immunogenic, High Molecular Weight Compound or a Lipophilic Compound.

It is a further object of the present invention to provide Complexes comprising one or more VEGF Nucleic Acid Ligands covalently linked to a Non-Immunogenic, High Molecular Weight Compound or Lipophilic Compound. Such Complexes have one or more of the following advantages over a VEGF Nucleic Acid Ligand not in association with a Non-Immunogenic, High Molecular Weight Compound or Lipophilic Compound: 1) Improved Pharmacokinetic Properties, and 2) improved capacity for intracellular delivery, or 3) improved capacity for targeting. Complexes further associated with a Lipid Construct have the same advantages.

The Complexes or the Lipid Constructs comprising the VEGF Nucleic Acid Ligand or Complexes may benefit from one, two, or three of these advantages. For example, a Lipid Construct of the present invention may be comprised of a) a Liposome, b) a drug that is encapsulated within the interior of the Liposome, and c) a Complex comprised of a VEGF Nucleic Acid Ligand and Lipophilic Compound, wherein the VEGF Nucleic Acid Ligand component of the Complex is associated with and projecting from the exterior of the Lipid Construct. In such a case, the Lipid Construct comprising a Complex will 1) have Improved Pharmacokinetic Properties, 2) have enhanced capacity for intracellular delivery of the encapsulated drug, and 3) be specifically targeted to the preselected location in vivo that is expressing VEGF by the exteriorly associated VEGF Nucleic Acid Ligand.

In another embodiment, this invention provides a method for improving the pharmacokinetic properties of a VEGF Nucleic Acid Ligand by covalently linking the VEGF Nucleic Acid Ligand with a Non-Immunogenic, High Molecular Weight Compound or Lipophilic Compound to form a Complex and administering the Complex to a patient. The invention further relates to a method for improving the pharmacokinetic properties of a VEGF Nucleic Acid Ligand by further associating the Complex with a Lipid Construct.

In another embodiment, the Complex of the present invention is comprised of a VEGF Nucleic Acid Ligand covalently attached to a Lipophilic Compound, such as a glycerolipid, phospholipid or glycerol amide lipid, or a Non-Immunogenic, High Molecular Weight Compound, such as Polyalkylene Glycol or polyethylene glycol (PEG). In these cases, the pharmacokinetic properties of the Complex will be enhanced relative to the VEGF Nucleic Acid Ligand alone. In another embodiment, the pharmacokinetic properties of the VEGF Nucleic Acid Ligand is enhanced relative to the VEGF Nucleic Acid Ligand alone when the VEGF Nucleic Acid Ligand is covalently attached to a Non-Immunogenic, High Molecular Weight Compound or Lipophilic Compound and is further associated with a Lipid Construct or the VEGF Nucleic Acid Ligand is encapsulated within a Lipid Construct.

In embodiments where there are multiple VEGF Nucleic Acid Ligands, there is an increase in avidity due to multiple binding interactions with VEGF. Furthermore, in embodiments where the Complex is comprised of multiple VEGF Nucleic Acid Ligands, the pharmacokinetic properties of the Complex will be improved relative to one VEGF Nucleic Acid Ligand alone. In embodiments where a Lipid Construct comprises multiple Nucleic Acid Ligands or Complexes, the Pharmacokinetic Properties of the VEGF Nucleic Acid Ligand may be improved relative to Lipid Constructs in which there is only one Nucleic Acid Ligand or Complex.

In certain embodiments of the invention, the Complex of the present invention is comprised of a VEGF Nucleic Acid Ligand attached to one (dimeric) or more (multimeric) other Nucleic Acid Ligands. The Nucleic Acid Ligand can be to VEGF or a different Target. In embodiments where there are multiple VEGF Nucleic Acid Ligands, there is an increase in avidity due to multiple binding interactions with VEGF. Furthermore, in embodiments of the invention where the Complex is comprised of a VEGF Nucleic Acid Ligand attached to one or more other VEGF Nucleic Acid Ligands, the pharmacokinetic properties of the Complex will be improved relative to one VEGF Nucleic Acid Ligand alone.

The Non-Immunogenic, High Molecular Weight compound or Lipophilic Compound may be covalently bound to a variety of positions on the VEGF Nucleic Acid Ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the VEGF Nucleic Acid Ligand. In embodiments where the Lipophilic Compound is a phospholipid, glycerolipid, or glycerol amide lipid, or the Non-Immunogenic, High Molecular Weight Compound is polyalkylene glycol or polyethylene glycol, preferably it is bonded to the 5' or 3' hydroxyl of the phosphate group thereof. In the most preferred embodiment, the Lipophilic Compound or Non-Immunogenic, High Molecular Weight Compound is bonded to the 5' hydroxyl of the phosphate group of the Nucleic Acid Ligand. Attachment of the Non-Immunogenic, High Molecular Weight Compound or Lipophilic Compound to the VEGF Nucleic Acid Ligand can be done directly or with the utilization of Linkers or Spacers. In embodiments where the Lipid Construct comprises a Complex, or where the VEGF Nucleic Acid Ligands are encapsulated within the Liposome, a Non-Covalent Interaction between the VEGF Nucleic Acid Ligand or the Complex and the Lipid Construct is preferred.

One problem encountered in the therapeutic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the VEGF Nucleic Acid Ligand can be made to increase the in vivo stability of the VEGF Nucleic Acid Ligand or to enhance or to mediate the delivery of the VEGF Nucleic Acid Ligand. Modifications of the VEGF Nucleic Acid Ligands contemplated in this invention include, but are not limited to, those which provide other chemical groups that incorporate additional charge, polarizability, hydrophobicity, hydrogen bonding, electrostatic interaction, and fluxionality to the VEGF Nucleic Acid Ligand bases or to the VEGF Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the Nucleic Acid Ligands are derived by the SELEX method, the modifications can be pre- or post-SELEX modifications. Pre-SELEX modifications yield VEGF Nucleic Acid Ligands with both specificity for VEGF and improved in vivo stability. Post-SELEX modifications made to 2'-OH Nucleic Acid Ligands can result in improved in vivo stability without adversely affecting the binding capacity of the Nucleic Acid Ligands. The preferred modifications of the VEGF Nucleic Acid Ligands of the subject invention are 5' and 3' phosphorothioate capping and/or 3'3' inverted phosphodiester linkage at the 3' end. In the most preferred embodiment, the preferred modification of the VEGF Nucleic Acid Ligand is 3'3' inverted phosphodiester linkage at the 3' end. Additional 2' fluoro (2'-F), 2' amino (2'-NH$_2$) and 2' O methyl (2'-OMe) modification of some or all of the nucleotides is preferred.

In another aspect of the present invention, the covalent linking of the VEGF Nucleic Acid Ligand with a Non-Immunogenic, High Molecular Weight Compound or Lipophilic Compound results in Improved Pharmacokinetic Properties (i.e., slower clearance rate) relative to the VEGF Nucleic Acid Ligand not in association with a Non-Immunogenic, High Molecular Weight Compound or Lipophilic Compound.

In another aspect of the present invention, the Complex comprising a VEGF Nucleic Acid Ligand and Non-Immunogenic, High Molecular Weight Compound or Lipophilic Compound can be further associated with a Lipid Construct. This association may result in Improved Pharmacokinetic Properties relative to the VEGF Nucleic Acid Ligand or Complex not in association with a Lipid Construct. The VEGF Nucleic Acid Ligand or Complex can be associated with the Lipid Construct through covalent or Non-Covalent Interactions. In another aspect, the VEGF Nucleic Acid Ligand can be associated with the Lipid Construct through Covalent or Non-Covalent Interactions. In a preferred embodiment, the association is through Non-Covalent Interactions. In a preferred embodiment, the Lipid Construct is a Lipid Bilayer Vesicle. In the most preferred embodiment, the Lipid Construct is a Liposome.

Liposomes for use in the present invention can be prepared by any of the various techniques presently known in the art or subsequently developed. Typically, they are prepared from a phospholipid, for example, distearoyl phosphatidylcholine, and may include other materials such as neutral lipids, for example, cholesterol, and also surface modifiers such as positively charged (e.g., sterylamine or aminomannose or aminomannitol derivatives of cholesterol) or negatively charged (e.g., diacetyl phosphate, phosphatidyl glycerol) compounds. MultilamellarLiposomes can be formed by conventional techniques, that is, by depositing a selected lipid on the inside wall of a suitable container or vessel by dissolving the lipid in an appropriate solvent, and then evaporating the solvent to leave a thin film on the inside of the vessel or by spray drying. An aqueous phase is then added to the vessel with a swirling or vortexing motion which results in the formation of MLVs. UVs can then be formed by homogenization, sonication or extrusion (through filters) of MLV's. In addition, UVs can be formed by detergent removal techniques.

In certain embodiments of this invention, the Lipid Construct comprises a targeting VEGF Nucleic Acid Ligand(s) associated with the surface of the Lipid Construct and an encapsulated therapeutic or diagnostic agent. Preferably the Lipid Construct is a Liposome. Preformed Liposomes can be modified to associate with the VEGF Nucleic Acid Ligands. For example, a Cationic Liposome associates through electrostatic interactions with the VEGF Nucleic Acid Ligand. A VEGF Nucleic Acid Ligand covalently linked to a Lipophilic Compound, such as a glycerolipid, phospholipid, or glycerol amide lipid can be added to preformed Liposomes whereby the glycerolipid, phospholipid, or glycerol amide lipid becomes associated with the liposomal membrane. Alternatively, the VEGF Nucleic Acid Ligand can be associated with the Liposome during the formulation of the Liposome. Preferably, the VEGF Nucleic Acid Ligand is associated with the Liposome by loading into preformed Liposomes.

It is well known in the art that Liposomes are advantageous for encapsulating or incorporating a wide variety of therapeutic and diagnostic agents. Any variety of compounds can be enclosed in the internal aqueous compartment of the Liposomes. Illustrative therapeutic agents include antibiotics, antiviral nucleosides, antifungal nucleosides, metabolic regulators, immune modulators, chemotherapeutic drugs, toxin antidotes, DNA, RNA, antisense oligonucleotides, etc. By the same token, the Lipid Bilayer Vesicles may be loaded with a diagnostic radionuclide (e.g., Indium 111, Iodine 131, Yttrium 90, Phosphorous 32, or gadolinium) and fluorescent materials or other materials that are detectable in in vitro and in vivo applications. It is to be understood that the therapeutic or diagnostic agent can be encapsulated by the Liposome walls in the aqueous interior. Alternatively, the carried agent can be a part of, that is, dispersed or dissolved in the vesicle wall-forming materials.

During Liposome formation, water soluble carrier agents may be encapsulated in the aqueous interior by including them in the hydrating solution, and lipophilic molecules incorporated into the lipid bilayer by inclusion in the lipid formulation. In the case of certain molecules (e.g., cationic or anionic lipophilic drugs), loading of the drug into preformed Liposomes may be accomplished, for example, by the methods described in U.S. Pat. No. 4,946,683, the disclosure of which is incorporated herein by reference. Following drug encapsulation, the Liposomes are processed to remove unencapsulated drug through processes such as gel chromatography or ultrafiltration. The Liposomes are then typically sterile filtered to remove any microorganisms which may be present in the suspension. Microorganisms may also be removed through aseptic processing.

If one wishes to encapsulate large hydrophilic molecules with Liposomes, larger unilamellar vesicles can be formed by methods such as the reverse-phase evaporation (REV) or solvent infusion methods. Other standard methods for the formation of liposomes are known in the art, for example, methods for the commercial production of Liposomes include the homogenization procedure described in U.S. Pat. No. 4,753,788 and the thin-film evaporation method described in U.S. Pat. No. 4,935,171, which are incorporated herein by reference.

It is to be understood that the therapeutic or diagnostic agent can also be associated with the surface of the Lipid Bilayer Vesicle. For example, a drug can be attached to a phospholipid or glyceride (a prodrug). The phospholipid or glyceride portion of the prodrug can be incorporated into the lipid bilayer of the Liposome by inclusion in the lipid formulation or loading into preformed Liposomes (see U.S. Pat. Nos. 5,194,654 and 5,223,263, which are incorporated by reference herein).

It is readily apparent to one skilled in the art that the particular Liposome preparation method will depend on the intended use and the type of lipids used to form the bilayer membrane.

The efficiency of delivery of a VEGF Nucleic Acid Ligand to cells may be optimized by using lipid formulations and conditions known to enhance fusion of Liposomes with cellular membranes. For example, certain negatively charged lipids such as phosphatidylglycerol and phosphatidylserine promote fusion, especially in the presence of other fusogens (e.g., multivalent cations like Ca2+, free fatty acids, viral fusion proteins, short chain PEG, lysolecithin, detergents and surfactants). Phosphatidylethanolamine may also be included in the Liposome formulation to increase membrane fusion and, concomitantly, enhance cellular delivery. In addition, free fatty acids and derivatives thereof, containing, for example, carboxylate moieties, may be used to prepare pH-sensitive Liposomes which are negatively charged at higher pH and neutral or protonated at lower pH. Such pH-sensitive Liposomes are known to possess a greater tendency to fuse.

In the preferred embodiment, the VEGF Nucleic Acid Ligands of the present invention are derived from the SELEX methodology. SELEX is described in U.S. patent application Ser. No. 07/536,428, entitled Systematic Evolution of Ligands by Exponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931, 473, filed Aug. 17, 1992, entitled Methods for Identifying Nucleic Acid Ligands, now U.S. Pat. No. 5,270,163 (see also WO 91/19813). These applications, each specifically incorporated herein by reference, are collectively called the SELEX Patent Applications.

The SELEX process provides a class of products which are Nucleic Acid molecules, each having a unique sequence, and each of which has the property of binding specifically to a desired Target compound or molecule. Target molecules are preferably proteins, but can also include among others carbohydrates, peptidoglycans and a variety of small molecules. SELEX methodology can also be used to Target biological structures, such as cell surfaces or viruses, through specific interaction with a molecule that is an integral part of that biological structure.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-target pairs between the Target and those Nucleic Acids having the strongest affinity for the Target.

3) The Nucleic Acids with the highest affinity for the target are partitioned from those Nucleic Acids with lesser affinity to the target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5–50%) are retained during partitioning.

4) Those Nucleic Acids selected during partitioning as having the relatively higher affinity for the target are then amplified to create a new Candidate Mixture that is enriched in Nucleic Acids having a relatively higher affinity for the target.

5) By repeating the partitioning and amplifying steps above, the newly formed Candidate Mixture contains fewer and fewer unique sequences, and the average degree of affinity of the Nucleic Acids to the target will generally increase. Taken to its extreme, the SELEX process will yield a Candidate Mixture containing one or a small number of unique Nucleic Acids representing those Nucleic Acids from the original Candidate Mixture having the highest affinity to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S. Pat. No. 5,580,737, describes a method for identifying highly specific Nucleic Acid Ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now U.S. Pat. No. 5,567,588, describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to IIIV-RT and HIV-1 Rev," now U.S. Pat. No. 5,496,938, describes methods for obtaining improved Nucleic Acid Ligands after SELEX has been performed. U.S. patent application Ser. No. 08/400,440, filed Mar. 8, 1995, entitled "Systematic Evolution of Ligands by EXponential Enrichment: Chemi-SELEX," now U.S. Pat. No. 5,705,337, describes methods for covalently linking a ligand to its target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2-positions of pyrimidines. U.S. patent application Ser. No. 08/134,028, supra, describes highly specific Nucleic Acid Ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of known and novel 2' Modified nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected Nucleic Acid Ligands with Lipophilic Compounds or Non-Immunogenic, High Molecular Weight Compounds in a diagnostic or therapeutic Complex as described in U.S. patent application Ser. No. 08/434,465, filed May 4, 1995, entitled "Nucleic Acid Complexes." The SELEX method further encompasses combining selected VEGF Nucleic Acid Ligands with lipophilic compounds, such as diacyl glycerol or dialkyl glycerol, as described in U.S. patent application Ser. No. 08/739,109, filed Oct. 25, 1996, entitled "Vascular Endothelial Growth Factor (VEGF) Nucleic Acid Ligand Complexes", now U.S. Pat. No. 5,859,228. Each of the above described patent applications which describe modifications of the basic SELEX procedure are specifically incorporated by reference herein in their entirety.

SELEX identifies Nucleic Acid Ligands that are able to bind targets with high affinity and with outstanding specificity, which represents a singular achievement that is unprecedented in the field of Nucleic Acids research. These characteristics are, of course, the desired properties one skilled in the art would seek in a therapeutic or diagnostic ligand.

In order to produce Nucleic Acid Ligands desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand has the highest possible affinity to the target. Additionally, Nucleic Acid Ligands can have facilitating properties.

In commonly assigned U.S. patent application Ser. No. 07/964,624, filed Oct. 21, 1992 ('624), now U.S. Pat. No. 5,496,938, methods are described for obtaining improved Nucleic Acid Ligands after SELEX has been performed. The '624 application, entitled Nucleic Acid Ligands to HIV-RT and HIV-1 Rev, is specifically incorporated herein by reference.

The SELEX process has been used to identify a group of high affinity RNA Ligands to VEGF from random 2'-aminopyrimidine RNA libraries and ssDNA ligands from random ssDNA libraries (U.S. patent application Ser. No. 08/447,169, filed May 19, 1995, entitled High-Affinity Oligonucleotide Ligands to Vascular Endothelial Growth Factor (VEGF), now U.S. Pat. No. 5,811,533, which is a Continuation-in-Part Application of U.S. patent application Ser. No. 08/233,012, filed Apr. 25, 1994, entitled High-Affinity Oligonucleotide Ligands to Vascular Endothelial Growth Factor (VEGF), now U.S. Pat. No. 5,849,079, both of which are incorporated herein by reference; see also Green et al. (1995) Chemistry and Biology 2:683–695).

In embodiments where the VEGF Nucleic Acid Ligand(s) can serve in a targeting capacity, the VEGF Nucleic Acid Ligands adopt a three dimensional structure that must be retained in order for the VEGF Nucleic Acid Ligand to be able to bind its target. In embodiments where the Lipid Construct comprises a Complex and the VEGF Nucleic Acid Ligand of the Complex is projecting from the surface of the Lipid Construct, the VEGF Nucleic Acid Ligand must be properly oriented with respect to the surface of the Lipid Construct so that its target binding capacity is not compromised. This can be accomplished by attaching the VEGF Nucleic Acid Ligand at a position that is distant from the binding portion of the VEGF Nucleic Acid Ligand. The three dimensional structure and proper orientation can also be preserved by use of a Linker or Spacer as described supra.

Any variety of therapeutic or diagnostic agents can be attached to the Complex for targeted delivery by the Complex. In addition, any variety of therapeutic or diagnostic agents can be attached encapsulated, or incorporated into the Lipid Construct as discussed supra for targeted delivery by the Lipid Construct.

In embodiments where the Complex is comprised of a Lipophilic Compound and a VEGF Nucleic Acid Ligand in association with a Liposome, for example, the VEGF Nucleic Acid Ligand could target tumor cells expressing VEGF (e.g., in Kaposi's sarcoma) for delivery of an anti-tumor drug (e.g., daunorubicin)or imaging agent (e.g., radiolabels). It should be noted that cells and tissues surrounding the tumor may also express VEGF, and targeted deliver of an antitumor drug to these cells would also be effective.

In an alternative embodiment, the therapeutic or diagnostic agent to be delivered to the Target cell could be another Nucleic Acid Ligand.

It is further contemplated by this invention that the agent to be delivered can be incorporated into the Complex in such a way as to be associated with the outside surface of the Liposome. (e.g., a prodrug, receptor antagonist, or radioactive substance for treatment or imaging). As with the VEGF Nucleic Acid Ligand, the agent can be associated through covalent or Non-Covalent Interactions. The Liposome would provide targeted delivery of the agent extracellularly, with the Liposome serving as a Linker.

In another embodiment, a Non-Immunogenic, High Molecular Weight Compound (e.g., PEG) can be attached to the Liposome to provide Improved Pharmacokinetic Properties for the Complex. VEGF Nucleic Acid Ligands may be attached to the Liposome membrane or may be attached to a Non-Immunogenic, High Molecular Weight Compound which in turn is attached to the membrane. In this way, the Complex may be shielded from blood proteins and thus be made to circulate for extended periods of time while the VEGF Nucleic Acid Ligand is still sufficiently exposed to make contact with and bind to its Target.

In another embodiment of the present invention, more than one VEGF Nucleic Acid Ligand is attached to the surface of the same Liposome. This provides the possibility of bringing the same VEGF molecules in close proximity to each other and can be used to generate specific interactions between the VEGF molecules.

In an alternative embodiment of the present invention, VEGF Nucleic Acid Ligands and a Nucleic Acid Ligand to a different Target can be attached to the surface of the same Liposome. This provides the possibility of bringing VEGF in close proximity to a different Target and can be used to generate specific interactions between VEGF and the other Target. In addition to using the Liposome as a way of bringing Targets in close proximity, agents could be encapsulated in the Liposome to increase the intensity of the interaction.

The Lipid Construct comprising a Complex allows for the possibility of multiple binding interactions to VEGF. This, of course, depends on the number of VEGF Nucleic Acid Ligands per Complex, and the number of Complexes per Lipid Construct, and mobility of the VEGF Nucleic Acid Ligands and receptors in their respective membranes. Since the effective binding constant may increase as the product of the binding constant for each site, there is a substantial advantage to having multiple binding interactions. In other words, by having many VEGF Nucleic Acid Ligands attached to the Lipid Construct, and therefore creating multivalency, the effective affinity (i.e., the avidity) of the multimeric Complex for its Target may become as good as the product of the binding constant for each site.

In certain embodiments of the invention, the Complex of the present invention is comprised of a VEGF Nucleic Acid Ligand attached to a Lipophilic Compound such as a glycerolipid, phospholipid or glycerol amide lipid. In this case, the pharmacokinetic properties of the Complex will be improved relative to the VEGF Nucleic Acid Ligand alone. As discussed supra, the glycerolipid, phospholipid or glycerol amide lipid may be covalently bound to the VEGF Nucleic Acid Ligand at numerous positions on the VEGF Nucleic Acid Ligand. In embodiments where a glycerolipid, phospholipid, or glycerol amide lipid is used, it is preferred that the VEGF Nucleic Acid Ligand is bonded to the lipid through phosphodiester linkages.

In another embodiment of the invention, the Lipid Construct comprises a VEGF Nucleic Acid Ligand or Complex. In this embodiment, the phospholipid, glycerolipid, or glycerol amide lipid can assist in the incorporation of the VEGF Nucleic Acid Ligand into the Liposome due to the propensity for a phospholipid, glycerolipid, or glycerol amide lipid to associate with other Lipophilic Compounds. The phospholipid, glycerolipid, or glycerol amide lipid in association with a VEGF Nucleic Acid Ligand can be incorporated into the lipid bilayer of the Liposome by inclusion in the formulation or by loading into preformed Liposomes. In the preferred embodiment, the phospholipid, glycerolipid, or glycerol amide lipid/VEGF Nucleic Acid Ligand Complex is included in the formulation. The phospholipid or glycerol lipid can associate with the membrane of the Liposome in such a way so as the VEGF Nucleic Acid Ligand is projecting into or out of the Liposome. In embodiments where the VEGF Nucleic Acid Ligand is projecting out of the Complex, the VEGF Nucleic Acid Ligand can serve in a targeting capacity. It is to be understood that additional compounds can be associated with the Lipid Construct to further improve the Pharmacokinetic Properties of the Lipid Construct. For example, a PEG may be attached to the exterior-facing part of the membrane of the Lipid Construct.

In other embodiments, the Complex of the present invention is comprised of a VEGF Nucleic Acid Ligand covalently linked to a Non-Immunogenic, High Molecular Weight Compound such as Polyalkylene Glycol or PEG. In this embodiment, the pharmacokinetic properties of the Complex are improved relative to the VEGF Nucleic Acid Ligand alone. The Polyalkylene Glycol or PEG may be covalently bound to a variety of positions on the VEGF Nucleic Acid Ligand. In embodiments where Polyalkylene Glycol or PEG are used, it is preferred that the VEGF Nucleic Acid Ligand is bonded through the 5' hydroxyl group via a phosphodiester linkage.

In certain embodiments, a plurality of Nucleic Acid Ligands can be associated with a single Non-Immunogenic, High Molecular Weight Compound, such as Polyalkylene Glycol or PEG, or a Lipophilic Compound, such as a phospholipid, glycerolipid, or glycerol amide lipid. The Nucleic Acid Ligands can all be to VEGF or VEGF and a different Target. In embodiments where there are multiple VEGF Nucleic Acid Ligands, there is an increase in avidity due to multiple binding interactions with VEGF. In yet further embodiments, a plurality of Polyalkylene Glycol, PEG, phospholipid, glycerol lipid or glycerol amide lipid molecules can be attached to each other. In these embodiments, one or more VEGF Nucleic Acid Ligands or Nucleic Acid Ligands to VEGF and other Targets can be associated with each Polyalkylene Glycol, PEG, phospholipid, glycerol lipid or glycerol amide lipid molecule. This also results in an increase in avidity of each Nucleic Acid Ligand to its Target. In embodiments where multiple VEGF Nucleic Acid Ligands are attached to Polyalkylene Glycol, PEG, phospholipid, glycerol lipid, or glycerol amide lipid, there is the possibility of bringing VEGF molecules in close proximity to each other in order to generate specific interactions between VEGF. Where multiple Nucleic Acid Ligands specific for VEGF and different Targets are attached to Polyalkylene Glycol, PEG, phospholipid or glycerol lipid, there is the possibility of bringing VEGF and another Target in close proximity to each other in order to generate specific interactions between the VEGF and the other Target. In addition, in embodiments where there are Nucleic Acid Ligands to VEGF or Nucleic Acid Ligands to VEGF and different Targets associated with Polyalkylene Glycol, PEG, phospholipid, glycerol lipid, or glycerol amide lipid a drug can also be associated with Polyalkylene Glycol, PEG, phospholipid, glycerol lipid, or glycerol amide lipid. Thus the Complex would provide targeted delivery of the drug, with Polyalkylene Glycol, PEG, phospholipid, glycerol lipid, or glycerol amide lipid serving as a Linker.

VEGF Nucleic Acid Ligands selectively bind VEGF. Thus, a Complex comprising a VEGF Nucleic Acid Ligand and a Non-Immunogenic, High Molecular Weight Compound or Lipophilic Compound or a Lipid Construct comprising a VEGF Nucleic Acid Ligand or a Complex are useful as pharmaceuticals or diagnostic agents. The present invention, therefore, includes methods of inhibiting angiogenesis by administration of a Complex comprising VEGF Nucleic Acid Ligand and a Non-Immunogenic, High Molecular Weight Compound or Lipophilic Compound, a Lipid Construct comprising VEGF Nucleic Acid Ligand or a Complex comprising a VEGF Nucleic Acid Ligand and a Non-Immunogenic, High Molecular Weight Compound or Lipophilic Compound. The VEGF Nucleic Acid Ligand-containing Complexes and Lipid Constructs can be used to treat, inhibit, prevent or diagnose any disease state that involves inappropriate VEGF production, particularly angiogenesis. Angiogenesis rarely occurs in healthy adults, except during the menstrual cycle and wound healing. Angiogenesis is a central feature, however, of various disease states, including, but not limited to cancer, diabetic retinopathy, macular degeneration, psoriasis and rheumatoid arthritis. The present invention, thus, also includes, but is not limited to, methods of treating, inhibiting, preventing or diagnosing diabetic retinopathy, macular degeneration, psoriasis and rheumatoid arthritis. Additionally, VEGF is produced and secreted in varying amounts by virtually all tumor cells. Thus, the present invention, includes methods of treating, inhibiting, preventing, or diagnosing cancer by administration of a Complex comprising a VEGF Nucleic Acid Ligand and a Non-Immunogenic, High Molecular Weight Compound or Lipophilic Compound, a Lipid Construct comprising a Complex, or a VEGF Nucleic Acid Ligand in association with a Lipid Construct without being part of the Complex. It has been shown that in a type of cancer, Kaposi's sarcoma (KS), cells not only produce abundant amounts of VEGF but also express functional VEGF receptors and therefore use VEGF for autocrine growth. Thus, the present invention includes a method of inhibiting Kaposi's Sarcoma by administration of a Complex comprising VEGF Nucleic Acid Ligand and a Non-Immunogenic, High Molecular Weight Compound or a Lipophilic Compound, a Lipid Construct comprising a Complex, or a VEGF Nucleic Acid Ligand in association with a Lipid Construct without being part of a Complex.

In one embodiment of the present invention, the Lipid Construct comprises a Complex comprised of a VEGF Nucleic Acid Ligand and a Lipophilic Compound with an additional diagnostic or therapeutic agent encapsulated in the Lipid Construct or associated with the interior of the Lipid Construct. In the preferred embodiment, the Lipid Construct is a Lipid Bilayer Vesicle, and more preferably a Liposome. The therapeutic use of Liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies or specific receptor ligands to the surface of the liposomes. In one embodiment of the present invention, the VEGF Nucleic Acid Ligand is associated with the outside surface of the liposome, and serves in a targeting capacity. Additional targeting components, such as antibodies or specific receptor ligands can be included on the liposome surface, as would be known to one of skill in the art. In addition, some efforts have been successful in targeting liposomes to tumors without the use of antibodies, see, for example, U.S. Pat. No. 5,019,369, U.S. Pat. No. 5,435,989, and U.S. Pat. No. 4,441,775, and it would be known to one of skill in the art to incorporate these alternative targeting methods.

Therapeutic or diagnostic compositions of a Complex comprising a VEGF Nucleic Acid Ligand and a Non-Immunogenic, High Molecular Weight Compound or Lipophilic Compound, a Lipid Construct comprising a Complex comprised of a VEGF Nucleic Acid Ligand and a Non-Immunogenic, High Molecular Weight Compound or Lipophilic Compound, and a VEGF Nucleic Acid Ligand in association with a Lipid Construct without being part of a Complex may be administered parenterally by injection, although other effective administration forms, such as intraarticular injection, inhalant mists, orally active formulations, transdermal iotophoresis or suppositories, are also envisioned. One preferred carrier is physiological saline solution, but it is contemplated that other pharmaceutically acceptable carriers may also be used. In one embodiment, it is envisioned that the carrier and the VEGF Nucleic Acid Ligand Complex constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the VEGF Nucleic Acid ligand. Such excipients are those substances usually and customarily employed to formulate dosages for parental administration in either unit dose or multi-dose form.

Once the therapeutic or diagnostic composition has been formulated, it may be stored in sterile vials as a solution, suspension, gel, emulsion, solid, or dehydrated or lyophilized powder. Such formulations may be stored either in ready to use form or requiring reconstitution immediately prior to administration. The manner of administering formulations containing VEGF Nucleic Acid Ligand for systemic delivery may be via subcutaneous, intramuscular, intravenous, intranasal or vaginal or rectal suppository.

The following examples are provided to explain and illustrate the present invention and are not to be taken as limiting of the invention. The structures of the Nucleic Acid Ligands described in the examples below are shown in FIG. 1. Example I describes the experimental procedures for generating 2'-F pyrimidine modified RNA ligands to VEGF. Example 2 describes the 2'-F pyrimidine -modified RNA ligands to VEGF. Example 3 describes the synthesis of glycerolipid, phospholipid, and glycerol amide lipid, and PEG-modified VEGF Nucleic Acid Ligands. Example 4 describes the pharmacokinetic properties of phospholipid (PL) and PEG modified VEGF Nucleic Acid Ligands. Example 5 describes the preparation of NX31838 PL -Liposome Complex, and Example 6 describes the in vivo efficacy of VEGF Nucleic Acid Ligand Complexes.

EXAMPLE 1

Experimental Procedures for 2'-Fluoro Pyrimidine—Modified RNA Ligands to VEGF

This example provides general procedures followed and incorporated in Example 2 for the evolution of 2'-Fluoro-modified Nucleic Acid Ligands to VEGF.

Materials

Recombinant human $VEGF_{165}$ purified from the insect cell-line Sf 21 was purchased from R & D Systems as a carrier-free lyophilized powder. The protein was resuspended in phosphate-buffered saline to a concentration of 10 $\mu$M and stored at $-20°$ C. in small aliquots until use. Aliquots were stored at $4°$ C. for up to 4 weeks after thawing. Sf21-expressed mouse $VEGF_{164}$, and *E. coli*-expressed human $VEGF_{121}$, VEGF/P1GF heterodimer, and P1GF were also purchased from R & D Systems as carrier-free, lyophilized preparations.

Oligonucleotides were purchased from Operon Technologies, Inc. or were synthesized using an Applied Biosystems Model 394 oligonucleotide synthesizer according to optimized protocols. 2'-F-and 2'-OMe-ribonucleotide phosphoramidites were prepared by JBL Scientific, Inc. (San Luis Obispo, Calif.). 2'-F-pyrimidine NTPs were also purchased from JBL. 2'-OH-purine NTPs and dNTPs were from Pharmacia Biotech, Piscataway, N.J.

*T. aquaticus* thermostable DNA polymerase (Taq polymerase) was purchased from Perkin Elmer-Cetus, (Foster City, Calif.); AMV reverse transcriptase (AMV RT) was from Life Sciences, Inc.; Klenow DNA polymerase was from New England Biolabs, Beverly, Mass. T7 RNA polymerase was from Enzyco, Inc. (Denver, Colo.). Sequenase DNA polymerase is produced by United States Biochemical Corp. (Cleveland, Ohio).

α-[$^{32}$P]-ATP and γ-[$^{32}$P]-ATP were obtained from New England Nuclear (Boston, Mass.).

The SELEX protocol

The SELEX procedure has been described in detail in the SELEX Patent Applications. Chemically synthesized DNA oligonucleotide libraries ("30N7" and "40N7") were prepared with randomized regions of 30 or 40 nucleotides flanked by common 5' and 3' fixed sequences (5'-TAATACGACTCACTATAGGGAGGACGATGCGG(30 or 40 N)CAGACGACTCGCCCGA-3'; SEQ ID NOS: 1 and 2). Italicized nucleotides at the 5' end of each template correspond to the T7 RNA polymerase promoter sequence. Oligonucleotide primers were also synthesized for use in template preparation and amplification, and reverse transcription: 5'-TCGGGCGAGTCGTCTG-3' ("3N7"; SEQ ID NO:3) and 5'-TAATACGACTCACTATAGGGAGGACGATGCGG-3' ("5N7" SEQ ID NO:4). DoLIble-stranded DNA templates were prepared by annealing primer 3N7 to the 30N7 or 40N7 libraries and extending the primer using Klenow DNA polymerase or AMV RT. The higher temperature of incubation used for AMV RT (45° C. rather than 37° C.) may better promote complete extension through highly structured template oligonucleotides. The libraries were transcribed using T7 RNA polymerase in the presence of 1 mM each 2'-OH-ATP and GTP, 3 mM each 2'-F-CTP and UTP, and 50 μCi α-$^{32}$P-ATP. RNAs were purified from denaturing polyacrylamide gels by excising the gel slice containing the RNA, crushing it, and soaking for an extended time in 2mM EDTA.

The SELEX process of affinity selection followed by selected pool amplification has been described in detail (See the SELEX Patent Applications). In brief, one round of selection and amplification was performed as follows: VEGF was mixed with a 5- or 10-fold excess of RNA in phosphate-buffered saline with 1 mM MgCl$_2$ (PBSM) (30N7 and 40N7 libraries) or in Tris-buffered saline, 1 mM MgCl$_2$, 1 mM CaCl$_2$ (TBSMC) (30N7 library only), and the mixture was serially diluted by three. After incubation at 37° C. for 15 minutes, the mixtures were passed through 0.45μ Type HA filters (Millipore) to collect complexes of VEGF with RNA. RNAs were eluted from selected filters by incubation in 2:1 phenol, pH 7:7 M urea. After precipitation from the aqueous phase, RNAs were annealed to primer 3N7 and reverse transcribed using AMV RT. The resultant cDNAs were amplified with 15 cycles of the polymerase chain reaction (PCR) using the 3N7 and 5N7 primers and Taq DNA polymerase. Transcription of the PCR product yielded a new library enriched for sequences with affinity for VEGF. At round 4, a substantial background filter-binding signal in the absence of VEGF had arisen in all three selected RNA pools. To deplete the pools of filter-binding RNAs, rounds 5 and 6 were performed with an alternative scheme for partitioning VEGF-bound RNAs from unbound molecules: after incubation of the RNA pool with the growth factor, each mixture was applied to an 8% polyacrylamide, nondenaturing gel and electrophoresed at 10 W for 45–60 minutes at 4° C. VEGF/RNA complexes migrated above the unbound RNA in this system and were visualized by exposure of X-ray film to the gel. For these rounds, selected RNAs were purified by the crush and soak method, as described above. After twelve rounds of selection and amplification, individual molecules in the selected pools were cloned using the pCR-Script Direct Cloning kit from Stratagene (La Jolla, Calif.). Plasmids were purified using the alkaline lysis method (PERFECTprep Plasmid DNA kit, 5 Prime→3 Prime, Boulder, Colo.) and sequences of the cloned regions were obtained using the Dye Terminator Cycle Sequencing kit available from Perkin Elmer (Foster City, Calif.). Fluorescent sequencing ladders were read at the National Jewish Center, laboratory of Brian Kotzin, Denver, Colo. Sequences were grouped into families and aligned by eye.

Measurement of binding affinities

Nucleic Acid Ligands radiolabeled during transcription by incorporation of α-[$^{32}$P]-labeled NTPs, or after synthesis using γ-[$^{32}$P]-ATP and T4 polynucleotide kinase, were incubated in low concentration (between 20 and 70 pM) with varying concentrations of VEGF or other growth factors at 37° C. for 15 minutes. Incubations were in TBS, PBS, or HEPES-buffered saline (HBS), pH 7.4, with or without the addition of supplemental divalent cations. Samples were passed through prewashed 0.45μ Type HA filters (Millipore) followed by a 5–10 ml wash with binding buffer. Filters were immersed in scintillant and counted to quantitate the amount of protein-bound RNA retained by each filter. The equilibrium dissociation constant ($K_D$) of Nucleic Acid Ligand binding to a specific protein was calculated from thc data points as described in Green et al. (1996) Biochem. 35: 14413–14424.

Affinity selection of Nucleic Acid Ligand fragments

Ten pmol internally-radiolabeled transcripts of high affinity VEGF Nucleic Acid Ligands were partially digested with S7 nuclease to generate a mixture of radiolabeled fragments. One-tenth of the fragmented RNA was incubated with 10 pM VEGF in 45 ml binding buffer, prior to filtration through nitrocellulose. Selected fragments recovered from the filter were run out on a high resolution denaturing polyacrylamide gel next to a lane loaded with the unselected fragment pool. The smallest selected bands were individually purified from the gel and further labeled at their 5' ends with polynucleotide kinase to increase their specific activity. One-half of the sample was annealed to a cDNA of the original transcript and extended to the end of the template using Sequenase DNA polymerase. Comparison of the migration of the purified fragment and its extension product to a standard sequencing ladder was used to determine the probable size and position of the selected fragment within the original transcript. Synthetic oligonucleotides corresponding in sequence to the affinity selected fragments were prepared to verify that the truncated Nucleic Acid Ligand retained affinity for VEGF.

2'-OMe-substitution

The 2'-OMe substitution experiments were performed essentially as described in Green et al. (1995) Chem. Biol. 2:683–695. Three or four libraries were prepared for each of three truncated ligands (t22, t2, t44) in which five or six 2'-OH-purine positions were partially 2'-OMe-substituted. Each purine position was partially 2'-OMe-modified in only one of the libraries. Each 5'-radiolabeled library was incubated with VEGF, and substituted oligonucleotides bound by the protein were collected on nitrocellulose filters. The selected pool and the starting unselected library were partially hydrolyzed by alkali and the products were displayed on a high resolution polyacrylamide gel. A "band intensity ratio" was determined for each purine position by dividing the phosphorimage signal obtained from hydrolysis at that position in the selected pool by the signal obtained for the same position in the unselected library. Band intensity ratios that fall well above the range for a particular position are indicative of a bias for 2'-OH (against 2'-OMe) in the affinity selected pool.

Binding rate constants

A small amount (typically less than 1 pmol) of 5'-radiolabeled Nucleic Acid Ligands were incubated with 1 nM VEGF at 37° C. in 1 ml buffered saline supplemented with divalent cations. At time "zero," 50 µl were filtered through nitrocellulose to determine the fraction of RNA bound to protein, then an excess (100 or 500 nM in different experiments) of unlabeled Nucleic Acid Ligand was added and 50 PI aliquots were filtered at time points thereafter. Filters were counted in scintillant to determine the amount of radiolabeled RNA still bound to VEGF at each time point. The data, plotted as fraction of RNA bound (f) vs time, was fitted to an equation for exponential decay:

$$f(t) = f_0 e^{-kt} + b,$$

where $f_0$ is the fraction of RNA bound at time zero, k is the dissociation rate constant ($k_d$) and b is the residual binding of radiolabeled RNA to the filter at the end of the experiment (effectively, in the absence of protein). Association rate constants ($k_a$s) were calculated from the measured $k_d$ and $K_D$ values according to the equation:

$$k_a = k_d / K_D$$

EXAMPLE 2

2'-Fluoro-Modified RNA Ligands to VEGF

Selection of Ligands

Ligands to VEGF were isolated in three separate SELEX experiments from libraries of 2'-F-pyrimidine-modified RNAs containing 30 or 40 random nucleotides. Selections were performed in PBS supplemented with 1 mM $MgCl_2$ (30N and 40N libraries) or in Tris-buffered saline with 1 mM $MgCl_2$ and 1 mM $CaCl_2$ (30N library only). Approximately $10^{14}$ unique sequences were included in the first selection cycle of each experiment. After ten cycles, the affinity between VEGF and each RNA pool had improved approximately 1000-fold relative to the starting pools. As no further improvement in binding affinity was observed after two additional cycles, individual members of the twelfth round pools were cloned and sequences were determined for about 50 isolates from each selection.

Oligonucleotide ligands to VEGF 165 were isolated in three separate SELEX experiments. Individual clones were isolated and sequenced and the sequences grouped into families based on shared primary structural motifs (Table 1). The name of each ligand indicates the target (V=VEGF), the selection buffer (P=PBS; T=TBS), the length of the randomized region in the library (30 or 40 nucleotides) and the clone number (following the decimal). The frequency with which a sequence appeared among the clones analyzed is indicated in parentheses; sequences that differed by only one nucleotide were attributed to PCR mutagenesis of a common precursor and were grouped together with the variable base indicated in the sequence by the appropriate symbol (Y=U or C). The fixed sequences common to all ligands are shown in lower case letters at the top. For individual clones the sequence of the variable region is shown in upper case. For some ligands, fixed region sequences in lower case are appended to the variable region sequence where they contribute to possible secondary structures. The high affinity Kd for binding to VEGF is shown for each ligand. One ligand in each family was selected for further analysis (gray box).

Of a total of 143 clones analyzed, 76 sequences differing by more than one nucleotide were obtained. 50 of these sequences could be grouped into three major families based on conserved primary structural motifs (Table 1). Minor families with five or fewer members and "orphaned" sequences that were unique among the isolates are not shown. Ligands containing the primary structural motif defined by Families 1 and 2 arose in all three affinity selections. Similarities between the conserved primary structures of both families suggest that they may also share similar secondary structures and/or that they may interface with VEGF using similar contact regions. Members of Family 2 share the possibility of forming a short basepaired stem enclosing the conserved sequence motif in a large "loop" (underlined in Table 1). With the exception of the closing A/U basepair, the sequence identity of bases in the putative stem regions is not conserved. Such "co-variation" of bases that conserves secondary rather than primary structure supports the existence of the putative stem and suggests that this structure may be important for the high affinity conformation of this family of VEGF ligands. No similarly conserved basepairing interactions were detected among Family 1 sequences. A third family of ligands arose only in the selections performed in TBSMC (Family 3, Table 1). In addition to a highly conserved primary structure motif, in all members of this family, sequences 3' of the conserved region share basepairing complementarity to nucleotides in the 5' fixed region (underlined in Table 1). Since, for most of the ligands, the bases on the 5' side of the putative stem cannot be said to covary with their basepairing partners, this observation is less predictive of a common secondary structure; nevertheless, our initial guess for a minimal high affinity sequence derived from this family (described below) was guided by the strong conservation of this motif. The affinities of the individual RNA ligands for VEGF were estimated based on a single determination of the $K_D$ for their interaction. With few exceptions, the ligands showed very high affinity for the growth factor, with $K_D$s generally falling between 5 and 50 pM.

Minimal Ligands

The shared primary and secondary structural motifs that define each sequence family hint at the minimal sequence elements required for high affinity binding to VEGF. Nested truncations of a representative ligand from each family (indicated by gray boxes in Table 1) were produced by chemical synthesis and their relative affinities for VEGF were determined (Table 2). Truncated versions of ligands VP30.22, VP30.2 and VT30.44 were prepared by chemical synthesis and their affinities for VEGF were determined as described in Materials and Methods. Initial truncations (t22, t2, t44) were further refined by synthesis of oligonucleotides with additional bases lacking from the 5' and/or 3' ends. In order to initiate the chemical synthesis, the 3'-most nucleotide of several of the ligands was modified either by substitution of 2'-OH-cytidine for 2'-F-cytidine (underlined) or by addition of a 3'-3'-linked deoxythymidine "cap" (asterisks). The length of each oligonucleotide (minus the cap) and its high affinity KD for binding to VEGF are shown.

An initial prediction for the minimal sequence from clone VP30.22 (Family 1) was made by mapping the ends of a purified, affinity-selected fragment of the full-length ligand (see Example 1). This 29 nucleotide molecule ("t22") showed an approximately three-fold loss in binding affinity for VEGF relative to the full length ligand. Further truncation at the 3' end of this molecule caused a precipitous loss in affinity but up to 6 additional nucleotides could be removed from the 5' end with little or no consequence (Table 2). For clone VP30.2 from Family 2 and clone VT30.44 from Family 3, truncated ligands "t2" and "t44" were synthesized that encompassed the putative five basepair stem and all of the conserved sequence motif. Both truncated ligands retained nearly all of the binding activity of the full length molecule. Further truncation by deleting one putative basepair at a time (one nucleotide from each end of the ligand) caused a gradual loss in affinity. Thus, for these sequences, truncations based on possible secondary structures predicted very well the minimal high affinity ligand, and further supports the hypothesis that the putative stems contribute to the high affinity conformation of these ligands.

2'-OMe modification

Substitution at the 2'-OH positions of RNA oligonucleotides by 2'OMe has been observed to improve their stability against nucleases present in rat urine as well as in other biological fluids. Stabilization of oligonucleotides to nucleases is likely to be critical to their success as therapeutic or diagnostic agents. Unfortunately, 2'-OMe-modified nucleoside triphosphates are not generally accepted as substrates by RNA polymerases under standard reaction conditions. However, 2'-OMe purines may be introduced into a specific oligonucleotide by chemical synthesis. It has been observed that some high affinity 2'-OH purine RNA ligands will accept a surprisingly high percentage of 2'-OMe purine substitutions with little loss of affinity for the target protein. To identify those purine positions for which 2'-OMe substitution is compatible with high affinity binding to VEGF, several syntheses of ligands t2, t22 and t44 were prepared in which five or six purines at a time were partially substituted with the modified nucleotide (described in Example 1). Affinity selection of each partially substituted library was used to isolate those molecules that retained substantial affinity for VEGF. In such an affinity selected pool, positions that do not tolerate substitution are biased for 2'-OH and thus show higher sensitivity to hydrolysis by alkali relative to the same position in the unselected library. 5'-radiolabeled unselected and affinity selected pools were partially hydolysed by alkali and the products were displayed on a high resolution polyacrylamide gel. In ligand t22, G10 and A12 showed substantial bias for 2'OH in the affinity selected pool, as did A6 and G21 in ligand t2, and A5 and A6 in ligand t44. While the foregoing analysis identifies those positions that are likely to disallow substitution with 2'OMe nucleotides, one cannot predict from these data how simultaneous modification of all other purines will affect binding affinity. In fact, ligand t22, synthesized with all 2'-OMe-purines except G10, A12 and G22 (which showed a marginal preference for 2'-OH), bound to VEGF with an affinity equal to if not better than the all 2'-OH-purine sequence (Table 3).

Truncated oligonucleotides (t22, t2, and t44) were chemically synthesized with all but one, two or three purine positions substituted with 2'-OMe-purines. The remaining 2'-OH-purines are indicated in each ligand name and are underlined in the ligand sequence. $K_D$s for the binding of each substituted ligand to VEGF are shown.

Further substitution at G22 had little effect on binding to VEGF, but incorporation of 2'-OMe at G10 or A12, as predicted, was detrimental to binding affinity. Similarly, ligands t2 and t44 tolerated 2'-OMe-substitution at all but two purines with a three- to four-fold impact on the affinity of the Nucleic Acid Ligand for VEGF (Table 3).

Binding affinities and rate constants for substituted truncates

In the hope of identifying highly 2'-substituted VEGF Nucleic Acid Ligands of minimal length, all 2'-OMe-substitutions that did not dramatically decrease binding were incorporated into truncated ligands t22c, t2a, and t44a (see Table 2). The resultant Nucleic Acid Ligands, t22OMe and t44OMe, bound to VEGF with KDs of 70 pM and 50 pM, respectively, while ligand t2OMe bound with a $K_D$ of approximately 140 pM (Table 3). These $K_D$s compare favorably with that of NX-213 ($K_D$=140 pM), a 2'-$NH_2$-pyrimidine-, 2'-OMe-purine-substituted oligonucleotide inhibitor of VEGF described previously (see U.S. patent application Ser. No. 08/447,169, now U.S. Pat. No. 5,811,533, which is incorporated herein by reference. Each of the truncated 2'-OMe-substituted oligonucleotides was found to compete with NX-213 and with one another for binding to VEGF.

Dissociation rate constants (kd) were determined for each of the three 2'-OMe-substituted ligands by following the loss of a preformed complex between radiolabeled ligand and VEGF upon the addition of a large excess of unlabeled ligand. Ligand t22-OMe showed the fastest rate of dissociation with a half life of approximately 60 seconds. Ligands t2-OMe and t44-OMe showed slightly slower rates of dissociation with half lives on the order of 170 and 90 seconds, respectively. Association rate constants ($k_a$), calculated from the equilibrium dissociation constant and the dissociation rate constant ($K_D=k_d/k_a$), ranged from $3\times10^7$ to $2\times10^8$ $M^{-1}sec^{-1}$ (Table 4). Such rapid rates of association suggest a near diffusion limited binding interaction between these ligands and VEGF, and are in line with the association rate constants observed for SELEX-derived Nucleic Acid Ligands to other targets.

In Table 4, truncated ligands t22c, t2a, and t44a are shown which were chemically synthesized with all but two 2'-OH-purine positions (underlined in sequence) substituted by 2'-OMe-purines (boldface). $K_D$, measured dissociation rate constant ($k_d$), calculated association rate constant ($k_a$) are shown for the resultant ligands, t22OMe, t2OMe and t44OMe, respectively. Values for $K_D$ and $k_d$ represent average +/− standard deviation (in parentheses) for six determinations or three to five determinations, respectively.

Divalent cation dependence

Ligands in Families 1 and 2 were selected in the presence of magnesium cations while Family 3 ligands were selected in a buffer containing both magnesium and calcium. Since divalent cations may contribute to RNA/protein interactions through nonspecific or specific stabilization of high affinity RNA structures, we asked whether magnesium and/or calcium were required for the high affinity binding of representative ligands to VEGF. The affinities of Nucleic Acid Ligands t22-OMe and t2-OMe (from Families 1 and 2, respectively) were unchanged in the presence or absence of supplemental divalent cations or the chelating agent EDTA (data not shown). However, Family 3 ligands, as represented by ligand t44-OMe, showed an absolute dependence on the presence of calcium for high affinity binding to VEGF. Binding was dramatically reduced ($K_D>10^{-7}$) when divalent cations in the binding buffer were replaced with EDTA. The addition of excess $MgCl_2$ to divalent-cation-depleted binding buffer gave no improvement in binding affinity, but $CaCl_2$, in two-fold molar excess over EDTA, fully restored binding activity. Identical binding behavior was observed for the unmodified ligand t44 (data not shown).

Protein specificity

The oligonucleotides described here were selected based on their affinities for $VEGF_{165}$, the larger of two diffusible isoforms of the growth factor. $VEGF_{121}$, the smaller isoform, lacks one of the exons in $VEGF_{165}$ and, unlike the latter, does not bind to heparin. None of the three truncated, 2'-OMe-substituted oligonucleotides bound with any measurable affinity to $VEGF_{121}$. Furthermore, the native structure of $VEGF_{165}$ is essential for the binding of all three Nucleic Acid Ligands, as no binding is observed when the protein is reduced with DTT prior to incubation with the oligonucleotides.

VEGF is a highly conserved protein across species, the human $VEGF_{165}$ and mouse $VEGF_{164}$ isoforms showing 88% sequence identity. The truncated, 2'-OMe-substituted ligands bound equally well to human and murine VEGF. However, no binding was observed for any of the ligands to homodimers of P1GF, a placenta-derived protein that shares 53% sequence identity with VEGF across the conserved platelet derived growth factor-like domain. Heterodimers between VEGF and P1GF have recently been isolated from the supernatants of both normal and tumor-derived cell lines, and such heterodimers show activity in binding to one of two high affinity VEGF receptors and in inducing responses in cultured endothelial cells. The biological relevance of VEGF/PlGF heterodimers is unknown. Substantial binding, though with greatly reduced affinities, was observed with VEGF/P1GF heterodimers. These data may indicate that the Nucleic Acid Ligands bind at or near the interface between the two subunits in a dimer and that PlGF does not present all of the contact sites necessary for high affinity binding. Alternatively, the structure of the VEGF subunit may be altered by participation in a heterodimer with P1GF with consequent distortion of the Nucleic Acid Ligand binding surface.

EXAMPLE 3

Synthesis of phospholipid, glycerol amide lipid, and PEG—modified VEGF Nucleic Acid Ligands Three different formulations were used for the synthesis of various Lipophilic Compound/Nucleic Acid Ligand Complexes as follows:

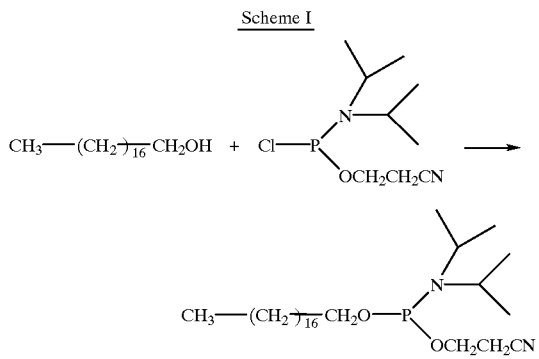

Scheme I

II. Synthesis of Lipid Amide 1

This phosphoramidite, unlike the above C-18 phosphoramidite, has amide linkages. The structure of the oligo resulting from conjugation of this lipid is shown below.

Several experiments demonstrated that high insolubility of compound 2 in organic solvents made NMR and MS characterization and further phosphitylation of compound 2

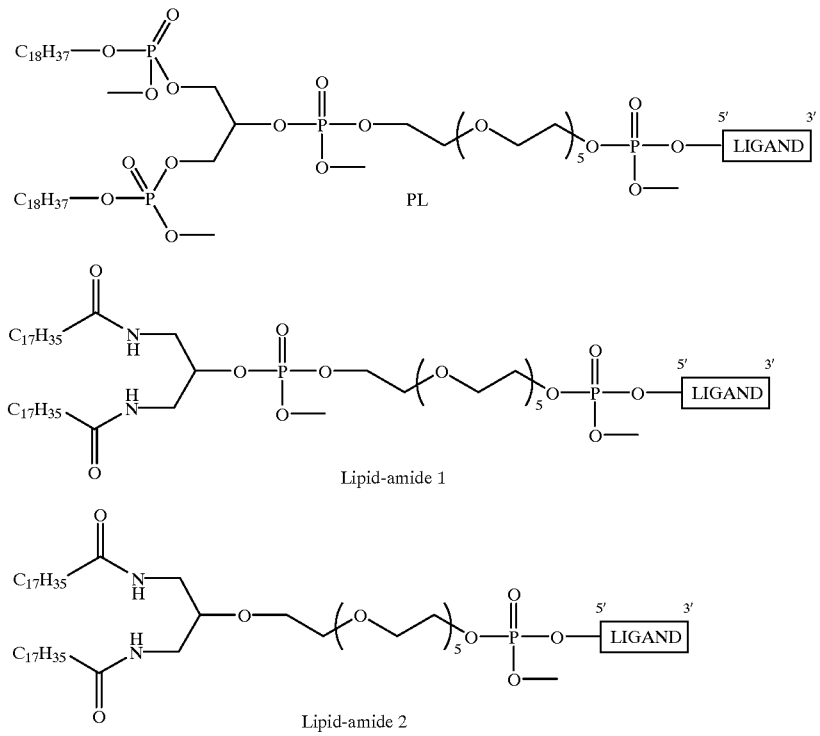

1. C-18 Phosphoramidite for the synthesis of PL formulation

An outline for the preparation of C-18 phosphoramidite is shown in Scheme I. 1-Octadecanol was phosphorylated under standard condition. After work up the reaction mixture, the residue was purified on silica gel column with hexane:ethyl acetate:triethylamine (90:10:5) to offer 21.5 g of pure product (57% yield).

to DAG amidite 1 impossible, however, from the results for preparation of Lipid-spacer amidite (Scheme I), we expected the phosphylation of compound 2 with chloro-(2-cyanoethoxy)-N,N-diisopropylamino-phosphine might go if refluxed the mixture. The approach to prepare the DAG amidite is shown in Scheme II.

Scheme II

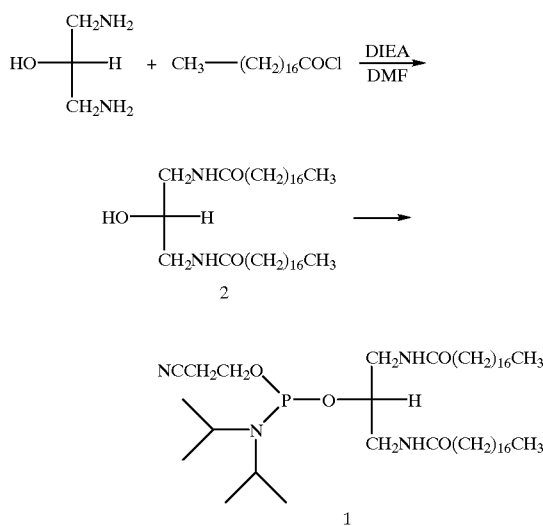

N,N'-Bis(stearoyl)-1,3-diaminopropanol-2 (2). A solution of stearoyl chloride (6.789 g, 22.41 mmol) in ClCH$_2$CH$_2$Cl (50 mL) was added dropwise to a solution of 1,3-diamino-2-hydroxypropane (1.0 g, 11.10 mmol) in ClCH$_2$CH$_2$Cl (100.0 mL) and TEA (2.896 g, 22.41 mmol) with stirring at R.T. After finishing addition, the mixture was heated to 70° C. overnight, and a clear solution was formed, and the solution was cooled to R.T., filtered, and the solids were washed with CH$_2$Cl$_2$ CH$_3$OH, 5% NaHCO$_3$ and ethyl ether, and dried in vacuo to give 2 (6.40 g, 93% yield) as white solids. $^1$H NMR (pyridine-d$_5$; 60° C., δ, ppm): 3.82–3.78 (m, 1H), 2.37 (t, J=7.5 Hz, 4H), 1.81–1.76 (m, 4H), 1.30–1.27 (m, 60H), 0.87(t,J=5.7 Hz, 6H).

N,N'-Bis(stearoyl)-O-(diisopropylamino-2-cyanoethoxyphosphinyl)-1,3-diaminopropanol-2 (1). Compound 2 (5.80 g, 9.31 mmol), dried overnight in vacuo, was in anhydrous CH$_2$Cl$_2$ (150.0 mL) and N,N-diisopropylethylamine (4.2 mL, 18.62 mmol) was injected. The mixture was cooled in an ice-water bath and chloro-(2-cyanoethoxy)-N,N-diisopropylamino-phosphine (8.6 mL, 0.47 mmol) was injected. After stirring for 30 min, the mixture was heated at 60° C. for 90 min. After cooling to R.T., insoluble materials were filtered and solution was washed with 5% NaHCO$_3$ and brine, dried over Na$_2$SO$_4$, and concentrated in vacuum. The crude product was purified by precipitation from CH$_3$CN to afford pure product (4.65g, 61% yield) as white solids. $^{31}$P NMR (CDCl$_3$, ppm): 154.04.

I. Synthesis of DAG-Spacer Amidite, Lipid Amide 2

Hexa(ethylene glycol) was incorporated into the lipid amidite in order to alleviate the insolubility of diamide compound 2, which is an intermediate to lipid amidite 1. An outline of the preparation of lipid-spacer amidite 3 is shown in Scheme I. The coupling step of compound 5 with 1,3-diamino-2-hydroxypropane and potassium t-butoxide in THF did not go well, and the yield was only about 20%. One attempt to improve yield was made by reacting 5 and diamide 2, however, no desired product was detected.

Scheme III

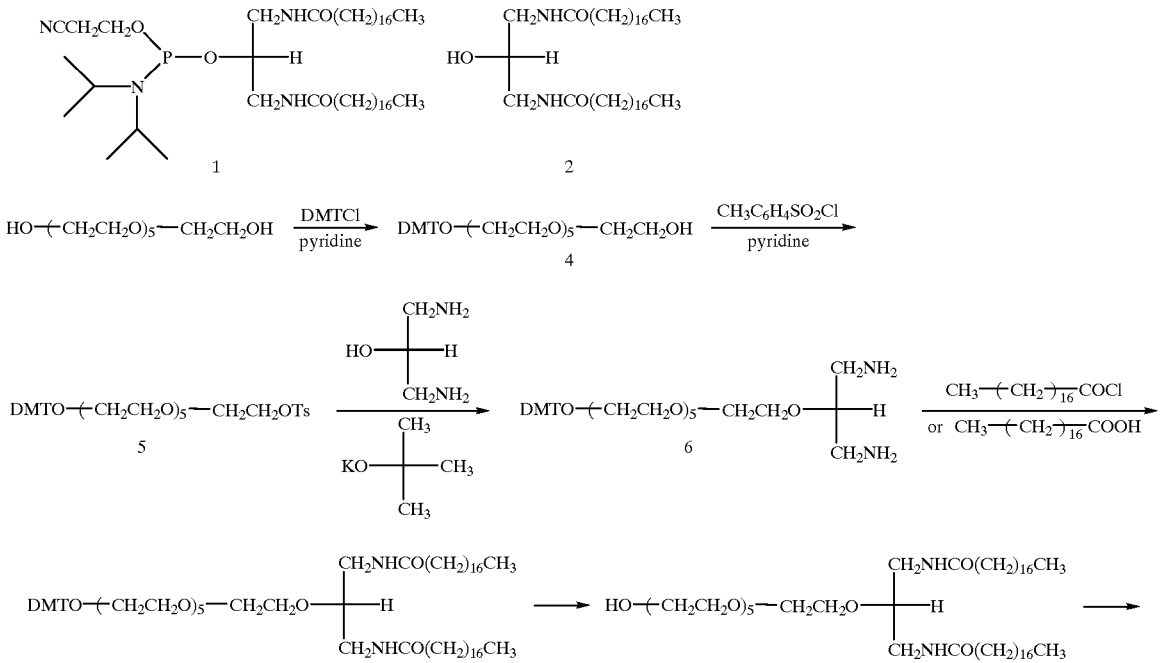

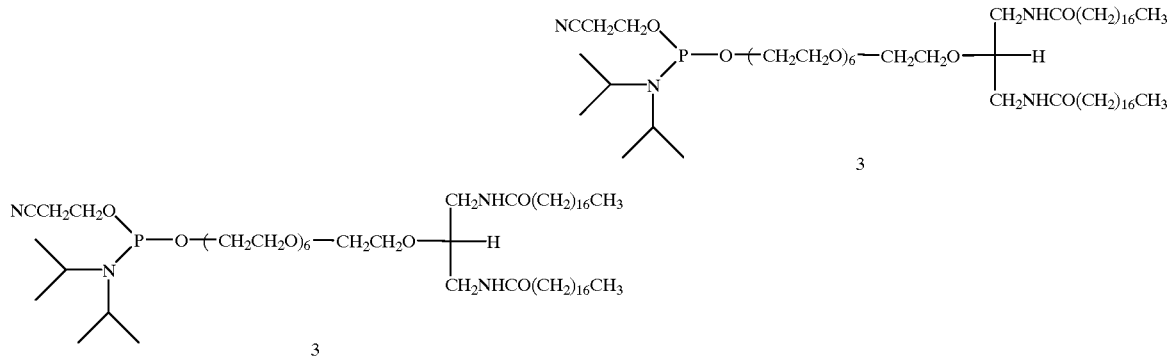

Lipid Amide 2

(4,4'-Dimethoxytrityloxy)-hexaethylene glycol (4). Hexa (ethylene glycol)(18.93 g, 67.05 mmol) was coevaporated with anhydrous pyridine (3×50 mL), dissolved in anhydrous pyridine (400 mL), and, after cooling to 0° C., DMTCl (23.85 g, 70.40 mmol) in pyridine (50 mL) was added dropwise during 30 min with stirring under Ar. The reaction mixture was kept at R. T. overnight. The pyridine was removed under high vacuum and residue was dissolved in $CH_2Cl_2$, which was washed with 5% $NaHCO_3$ and brine, dried over $Na_2SO_4$, and concentrated in vacuum. The crude product was purified by wet-flash silica gel column chromatography in a gradient of ethyl acetate, then $CH_2Cl_2$ and methanol (95/5) containing 0.5% TEA. The appropriate fractions were combined, evaporated, and dried in vacuum to give 4 (26.1 g, 66.6% yield) as a light yellow oil. $^1H$ NMR (DMSO-$d_6$; δ, ppm): 7.40 (d, J=7.2 Hz, 2H), 7.33–7.24 (m, 7H), 6.89 (d, J=8.9 Hz, 4H), 4.61 (t, J=5.1 Hz, 1H), 3.73 (s, 6H), 3.05 (m, 24H); $^{13}C$ NMR (DMSO-$d_6$; δ, ppm): 158.02, 145.02, 135.78, 129.67, 128.13, 127.71, 126,61, 113.14, 85.29, 72.33, 72.27, 70.06, 69.87, 69.80, 69.75, 69.70, 62.84, 60.25, 60.19, 55.01.

(4,4'-Dimethoxytrityloxy)-hexaethylene glycol tosylate (5). To an ice cooled solution (0° C.) of 4 in anhydrous pyridine (50 mL), was added a solution of toluene sulfonyl chloride in pyridine (30 mL). After 2 h at R. T., the solution was evaporated to a light yellow oil. The residue was taken-up in $CH_2Cl_2$ and washed with 5% $NaHCO_3$ and brine, dried over $Na_2SO_4$, filtered and evaporated in vacuo. The product was purified by wet-flash silica gel chromatography, eluting with ethyl acetate to give the product (4.08 g, 93% yield) as light yellow oil. $^1H$ NMR (DMSO-$d_6$; δ, ppm): 7.78 (d, J=8.3 Hz, 2H), 7.46 (d, J=8.1 Hz, 2H), 7.40 (d, J=7.4 Hz, 2H), 7.32–7.23 (m, 7H), 6.88 (d, J=8.8 Hz, 4H), 4.09 (t, J=4.3 Hz, 2H), 3.72 (s, 6H), 3.06 (m, 22H), 2.40 (s, 3H); $^{13}C$ NMR (DMSO-$d_6$,; δ, ppm): 158.01, 145.01, 135.78, 132.38, 130.12, 129.67, 128.12, 128.02, 127.80, 127.70, 127.62, 113.13.

2-(4,4'-Dimethoxytrityloxy)-hexaethylene glycol-1,3-diaminopropane (6). A mixture of 1,3-diamino-2-hydroxypropane (747 mg, 8.28 mmol) and potassium t-butoxide (2.78 g, 24.84 mmol) in anhydrous THF was heated to 70° C. for 2 h and then cooled to R.T. Compound 5 (4.08 g, 5.25 mmol) in THF was injected, and the mixture was stirred at 70° C. overnight until TLC showed no more 5 was left. After the solution was cooled to R.T., THF was removed in vacuo, and 25 mL of $CH_2Cl_2$ and 25 mL water were added. The $CH_2Cl_2$ layer was separated, and the water later was extracted with $CH_2Cl_2$. The $CH_2Cl_2$ solutions were combined, dried over $Na_2SO_4$ and evaporated under reduced pressure. The crude product (2.43 g) was directly used for reaction without further purification. $^1H$ NMR (DMSO-$d_6$; δ, ppm): 7.41 (d, J=7.7 Hz, 2H), 7.32–7.21 (m, 7H), 6.87 (d, J=8.8 Hz, 4H), 3.73 (s, 6H), 3.52–3.40 (m, 24H), 3.17 (s, 1H), 3.07–3.02 (m, 4H).

N,N'-Bis(stearoyl)-2-(4,4'-dimethoxytrityloxy)-hexaethyleneglycol-1,3-diaminopropane (7). A solution of stearoyl chloride (3.363 g, 11.1 mmol) in $ClCH_2CH_2Cl$ was injected into a solution of 6 in $ClCH_2CH_2Cl$ and TEA (1.9 mL, 11.1 mmol) with stirring in R.T. The mixture was kept at R.T. for 2 h, then heated to 70° C. overnight. After the solution was cooled to R.T., the solution was washed with 5% $NaHCO_3$ and brine, dried over $Na_2SO_4$, and concentrated in vacuum. The crude product was purified by wet-flash silica gel column chromatography in a gradient of ethyl acetate and $CH_2Cl_2$ (50/50) and then ethyl acetate and methanol (50/50). The second fraction was collected, evaporated, and dried in vacuum to give 7 (640 mg) as a light yellow solid. $^1H$ NMR (DMSO-$d_6$; δ, ppm): 7.40 (d, J=7.2 Hz, 2H), 7.37–7.20 (m, 7H), 6.74 (d, J=8.9 Hz, 4H), 3.71 (s, 6H), 3.63–3.51 (m, 24H), 3.17 (s, 1H), 3.16–3.13 (m, 4H), 2.12 (t, J=7.3 Hz, 4H), 1.18 (m, 60H), 0.80 (t, J=6.2 Hz, 6H).

N,N'-Bis(stearoyl)-2-hexaethylene glycol-1,3-diaminopropane (8). A mixture of compound 7 (640 mg), 2.5% DCA solution in $CH_2Cl_2$ (5 mL) and trihexylsilane (2 mL) was stirred at R.T. until orange color turned to pale color. After removal of $CH_2Cl_2$ the residue was repeatedly precipitated from hexane to give a light yellow solid (210 mg, 63% yield). $^1H$ NMR (CDCl$_3$, δ, ppm): 3.3.69–3.59 (m, 24H), 3.17 (s, 1H), 3.06–3.01 (m, 4H), 2.21 (t, J=7.9 Hz, 4H), 1.18 (m, 60H), 0.81 (t, J=6.3 Hz, 6H).

N,N'-Bis(stearoyl)-2-(diisopropylamino-2-cyanoethoxyphosphinyl-hexaethylene glycol)-1,3-diaminopropane (3). Compound 8 (210mg, 0.237 mmol), dried overnight in vacuo, was dissolved in anhydrous $CH_2Cl_2$ (5.0 mL) and N,N-diisopropylethylamine (218 μL, 1.25 mmol) was added. The solution was cooled in an ice-water bath and chloro-(2-cyanoethoxy)-N,N-diisopropylamino-phosphine (106 μL, 0.47 mmol) was injected. After stirring for 30 min, the reaction mixture was diluted with $CH_2Cl_2$ and washed with 5% $NaHCO_3$ and brine, dried over $Na_2SO_4$, and concentrated in vacuum to afford compound 3 $^{31}P$ NMR (CDCl$_3$, ppm): 154.04.

Conjugation of 20K or 40K Peg NHS ester to VEGF Nucleic Acid Ligands

General procedure: VEGF oligonucleotide was exchanged for Triethylammonium salt and lyophilysed. The crude oligonucleotide was dissolved in 100 mM sodium borate buffer (pH 9) to 60 mg/ml concentration. 2 Eq of Peg NHS ester (Shearwater Polymers, Inc.) was dissolved in dry DMF (Ratio of borate: DMF 1:1). And the mixture was warmed to dissolve the Peg NHS ester. Oligo solution was quickly added to PEG solution and the mixture was vigorously stirred at room temperature for 10 min. About 90% of the oligo gets conjugated to PEG NHS ester. See FIGS. 1D and 1E.

EXAMPLE 4

Pharmacokinetic Properties of phospholipid (PL) and PEG modified VEGF Nucleic Acid Ligands The pharmacokinetic properties of VEGF Nucleic Acid Ligand NX31838 conjugated to 20 and 40K PEG, were determined in Sprague Dawley rats (see FIG. 1 for molecular descriptions) (SEQ ID NOS: 8 and 9). Similar studies were also carried out on NX31838 conjugated to PL lipid as a liposomal formulation and as free drug (see FIG. 1 for molecular descriptions) (SEQ ID NOS: 5–7). In each study the oligonucleotide was diluted in PBS to a solution concentration of 1.0 mg/ml based on UV absorption at 260 nm and an extinction coefficient of 0.037 $\mu$g oligo/ml. In all studies, 9 rats received 1.0 mg oligonucleotide/kg animal weight by bolus tail vein injection and plasma samples were taken at various times from 2 minutes to 24 hours. The plasma samples and quality control samples were analyzed using a hybridization assay. The hybridization assay utilized a capture oligonucleotide that contains a complementary sequence to the 5'-end of the VEGF Nucleic Acid Ligand conjugated to an iron oxide (FeO) bead (FeO-spacer-3'-d (GCC TTA GTC ACT T-5') (SEQ ID NO: 87) where spacer=$(dT)_8$), and a detection oligonucleotide containing two biotin molecules at the 5'-end (biotin-biotin-5'-d(spacer-CGG ATG TAT AAG CA-3'), where spacer=$(dT)_8$) (SEQ ID NO: 88). After incubation of the capture and detect probes with a plasma sample containing VEGF Nucleic Acid Ligand NX31838 the amount of the biotin oligonucleotide hybridized to the bead was quantitated with the streptavidin-linked alkaline phosphatase, using CSPD-Sapphire as the luminescent substrate.

Figure 2:
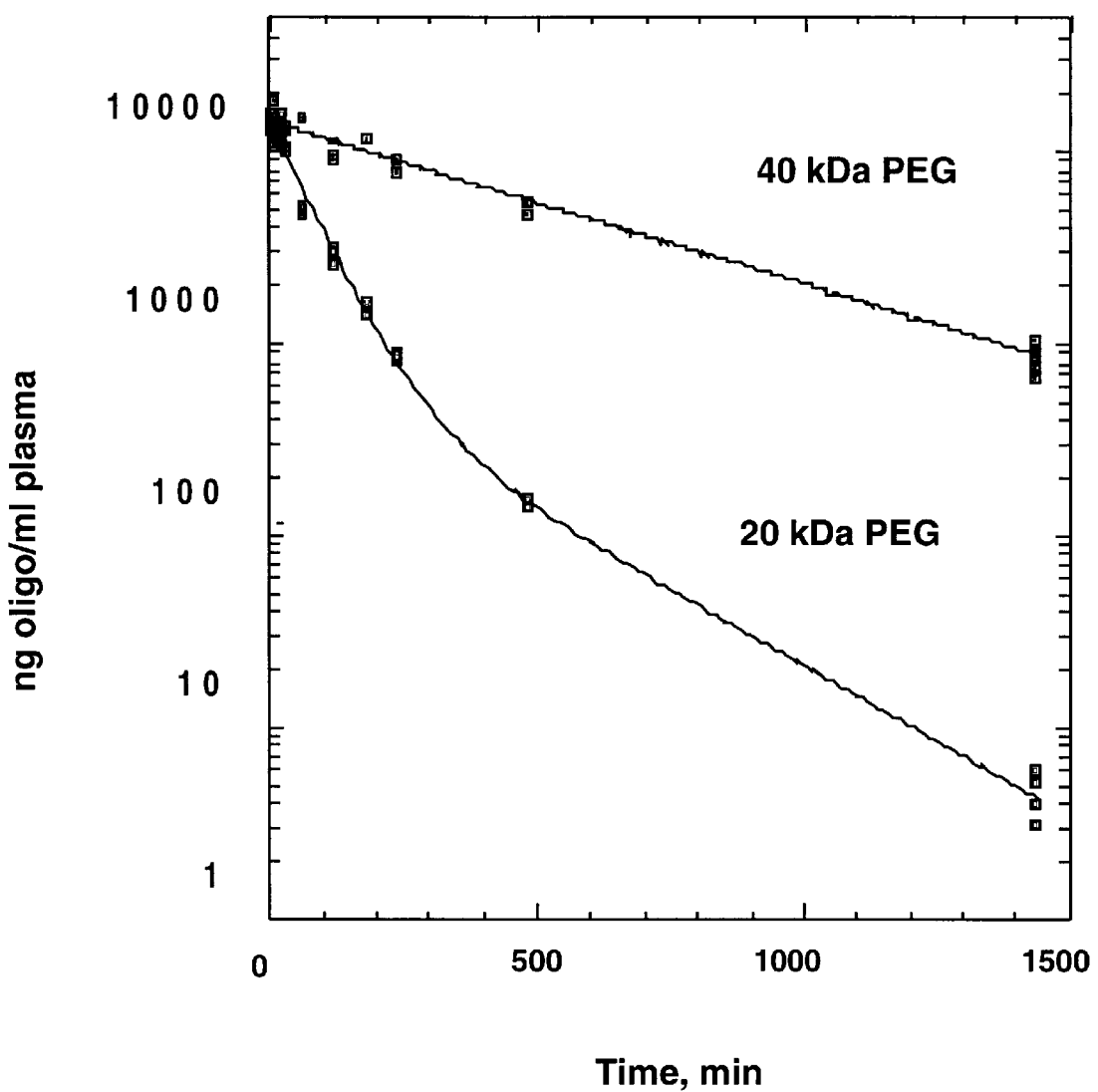
FIG. 2 summarizes the data for the plasma concentration of NX31838 20K PEG □ and 40K PEG■ as a function of time following the bolus injection.
Figure 3:
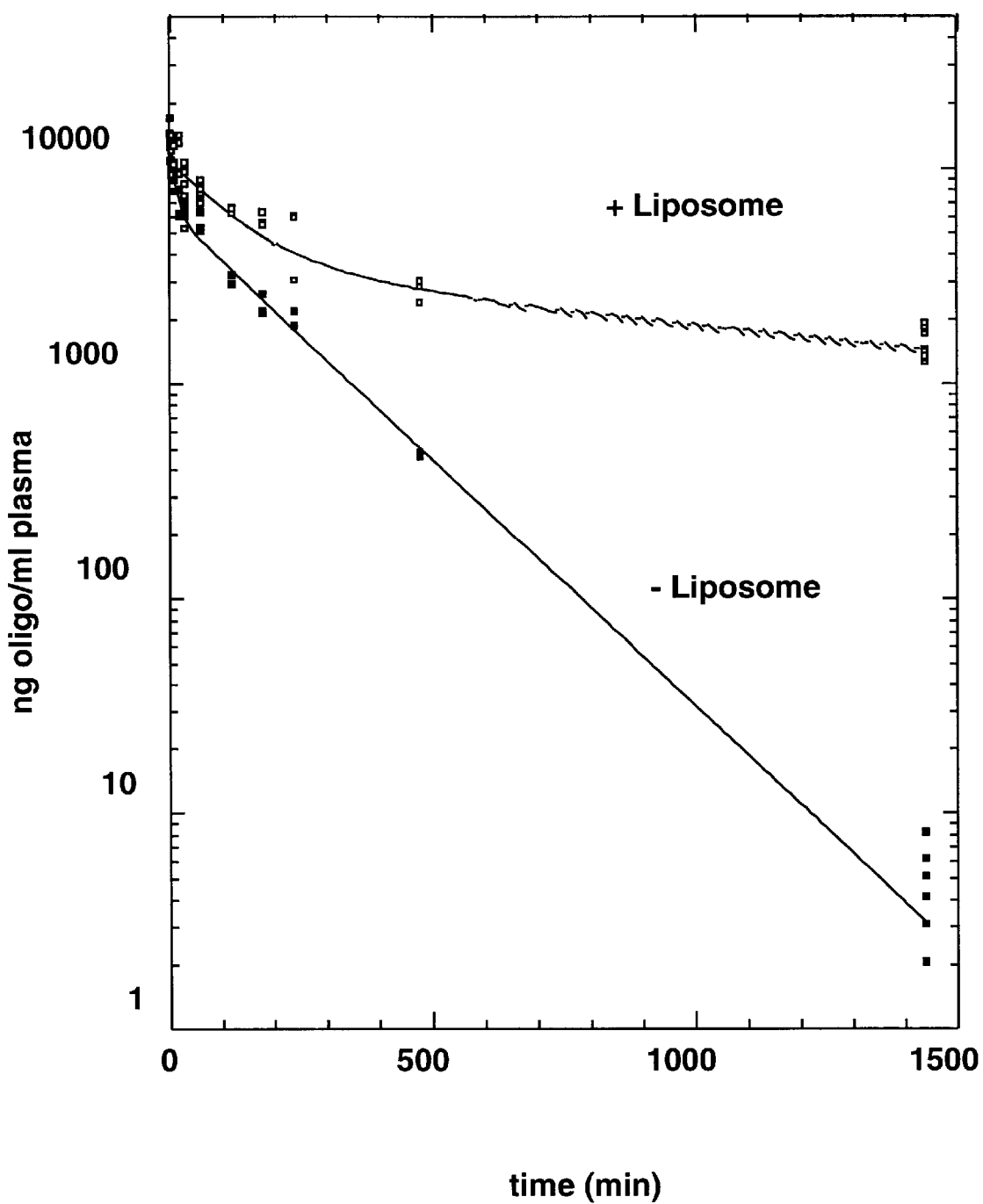
FIG. 3 summarizes the data for the plasma concentration of NX31838 PL as a function of time following the bolus injection.

Data for the plasma concentration of PEG20K and PEG40K VEGF Nucleic Acid Ligands (SEQ ID NOS: 8 and 9) as a function of time following bolus injection are summarized in FIG. 2. The 40K PEG conjugate was cleared with a monoexponential t1/2 of 360 minutes, while the 20K PEG version was cleared much more rapidly with 95% of the Nucleic Acid Ligand being cleared with an alpha $t_{1/2}$ of 49 minutes and 5% being cleared with a beta $t_{1/2}$ of 192 minutes, indicating the apparent importance of size on clearance. The plasma concentration of an oligonucleotide as a function of time can be significantly increased by introducing appropriate functional groups into the oligonucleotide.

Data for the plasma concentration of PL lipid conjugated VEGF Nucleic Acid Ligand formulated with and without liposomes as a function of time following bolus injection are summarized in FIG. 2. The liposomes were created by sonication in the presence of Nucleic Acid Ligand and contain oligo on the inside as well as the outside. The liposomal formulation was cleared much more slowly than the free drug, beta $t_{1/2}$ of 1161 minutes and 131 minutes, respectively. The plasma concentration of an oligonucleotide as a function of time can be significantly increased by liposomal formulation.

EXAMPLE 5

Preparation of NX31838 PL-Liposome Complex Liposome preparation by filming.

The lipids are combined at a ratio of 2 moles DSPC to 1 mole cholesterol. NX 31838 PL, in water, is added to the lipids at a ratio of 1:50 (w/w). The material is combined by solvating with a solution of chloroform: methanol : water (1:3:1). The solvent is removed by rotary evaporation leaving a heterogeneous film of NX 31838 PL co-mixed with the lipids. The film is rehydrated to 50 mg/mL, based on the lipids, in a solution of 9% sucrose, buffered with 25 mM sodium phosphate at pH 7.4. The solution is mixed vigorously, heated to 65° C. and the resultant white milk-like solution sonicated in 75 mL aliquots to assemble the lipids into unilamellar liposomes. The progress of liposome formation is followed visually until the solution becomes opalescent and then by particle sizing via dynamic light scattering using a particle analyzer (Leeds & Northrup Model Microtrack UPA 150, Horsham, Pa.). Liposome size is in the range of 50 to 70 nm (by volume weight distribution method).

EXAMPLE 6

In Vivo Efficacy of VEGF Nucleic Acid Ligand Complexes

Dermal Vascular Permeability Assay: The ability of several different formulations of the NX31838 Nucleic Acid Ligand to attenuate VEGF-induced changes in the permeability of the dermal vasculature (Miles Assay) was performed as previously described (Senger et al. (1986) Cancer Research 46:5629–5632) with minor modifications. Briefly, adult female guinea pigs (3/study) were anesthetized with isoflurane and the hair on the dorsal and lateral back areas was removed with clippers. Evans Blue dye (2.5 mg/guinea pig) was administered intravenously. Injection solutions (PBS, VEGF, NX31838 formulations, and anti-VEGF monoclonal antibody) were prepared 30 min in advance, co-mixed where indicated, with final concentrations as shown. Each solution shown was then injected intradermally (duplicate injections/guinea pig; 40 $\mu$l/site) in a randomized manner in a grid pattern drawn on the clippered area. Guinea pigs were allowed to recover from anesthesia and were sacrificed by $CO_2$ exposure 30 min after completion of the intradermal injections. The skin was then harvested, trimmed free of subcutis, and transilluminated. Images were then captured using a color CCD camera (Hitachi Denshi KP-50U, Japan) and Image-Pro Plus software (Version 3.1, Media Cybernetics, Silver Springs, Md.). Each skin sample was normalized for intensity with each injection site analyzed for optical density and the area involved.

Figure 4A:
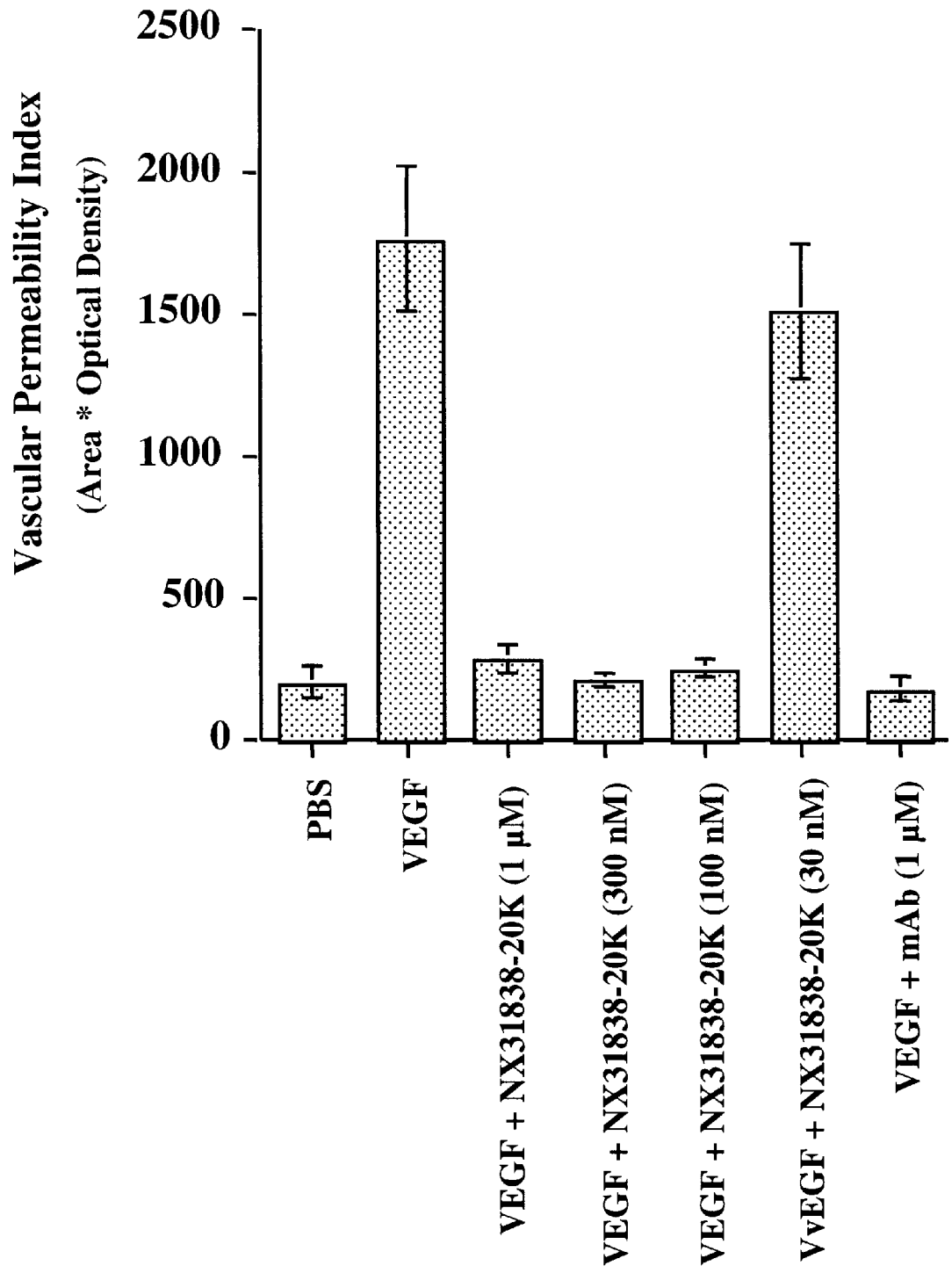
FIGS. 4A–4C shows changes in vascular permeability elicited by intradermal injection of VEGF protein (0.8 pmol) ±Nucleic Acid Ligand/monoclonal antibody as indicated. Local extravasation of Evans blue dye was determined 30 min after injection by transillumination of harvested skin. Figures A, B, and C show the effect of co-mixing NX31838-20K PEG, NX31838-40K PEG, or NX3l1838-PI, with protein 30 min prior to injection. Values are mean ±SEM. * $P<0.05$ compared with VEGF alone. See FIG. 1 for molecular descriptions.
Figure 4B:
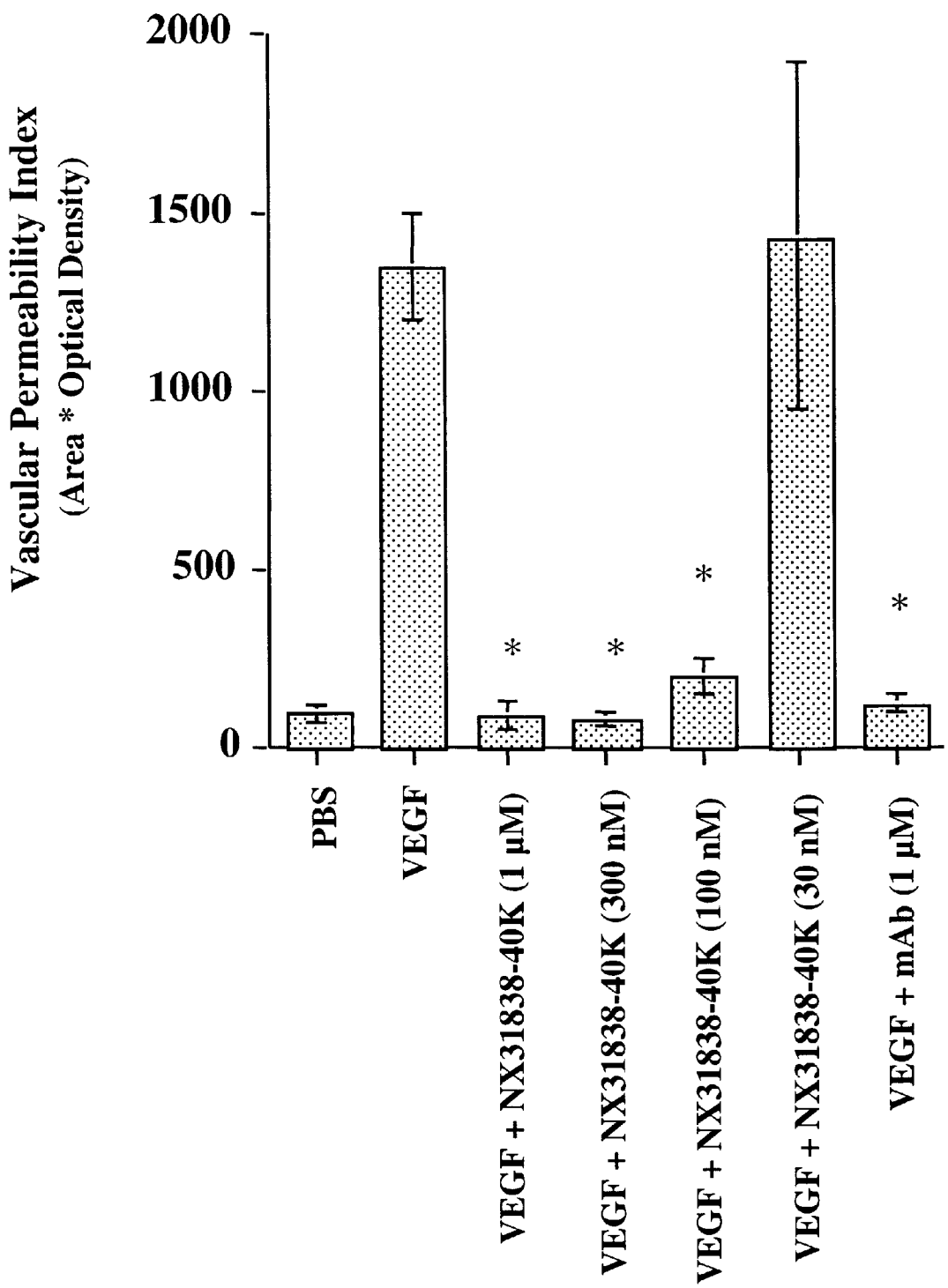
Figure 4C:
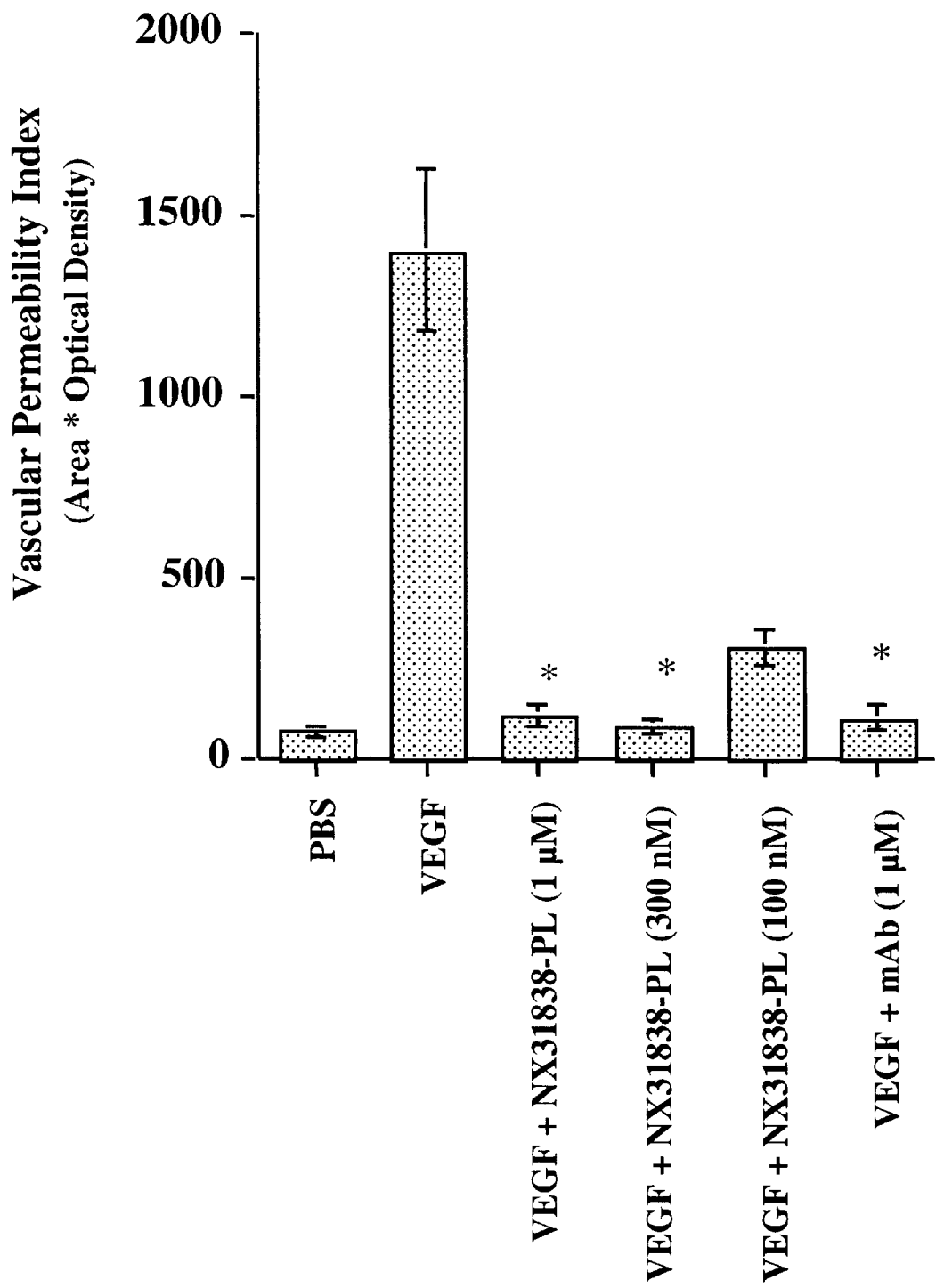

FIGS. 4A–C show the results of Nucleic Acid Ligand attenuation of VEGF-induced vascular leakage for NX31838-20K PEG, NX31838-40K PEG, NX31838-PL in liposomal preparation as described in Example 5. All formulations were able to significantly reduce vascular leakage down to or near PBS control levels with concentrations as low as 100 nM. At 30 nM the blocking effect of the Nucleic Acid Ligand was lost. The NX31838-PL liposomal formulation was not evaluated at this concentration but appeared to have reduced blocking activity at 100 nM. The anti-VEGF monoclonal antibody was also evaluated in this model system (data not shown) and was likewise effective down through 100 nM with loss of activity at 30 nM. Thus, suggesting that in this model system that NX31838 in the various formulations examined is equally effective as antibody in blocking one of the functional effects of VEGF protein.

Corneal Pocket Model: VEGF Nucleic Acid Ligand (NX31838) formulations were tested in their ability to reduce VEGF-induced corneal angiogenesis in the normally avascular rat cornea. Briefly, biopolymer (Hydron) pellets±VEGF protein (3 pmol) were prepared approximately 30 hr before by adding the protein or carrier solution to 12% biopolymer in 95% ethanol. Adult, Sprague-Dawley rats (200–240 g) were anesthetized by intraperitoneal injection of ketamine HCl (50 mg/kg) and xylazine (10 mg/kg). The left eye was then prepared by topical administration of tetracaine HCl for local anesthesia followed by application of dilute povidone-iodine solution and subsequent rinsing with isotonic saline solution. A vertical partial thickness incision was made in the mid-cornea. A mid-stromal pocket was dissected caudally toward the lateral canthus extending to within 1.5 mm of the limbus. A pellet was then inserted into and pushed to the caudal limit of the pocket. Residual air was gently massaged out of the pocket. A drop of chloramphenicol ophthalmic solution was then applied to the eye. The animal was rolled over and the procedure repeated on the right eye with insertion of the same type of pellet. Upon completion of pellet insertion in each eye, each animal was then administered either PBS (volume matched to Nucleic Acid Ligand formulation group) or Nucleic Acid Ligand (10 mg/kg) intravenously twice daily as indicated. At 5 days, each animal was anesthetized and photographs were taken using a 35 mm camera (Minolta X9) mounted on a dissecting microscope (KAPS, Germany). Each eye was evaluated for the angiogenic response by measuring the maximum length of vessel growth (0–5), the density of vessel growth (1–4) adjacent to the implanted pellet, and the circumference of the eye with angiogenesis occurring (0–1). An angiogenic index was then determined as the product of length * density * circumference.

Figure 5A:
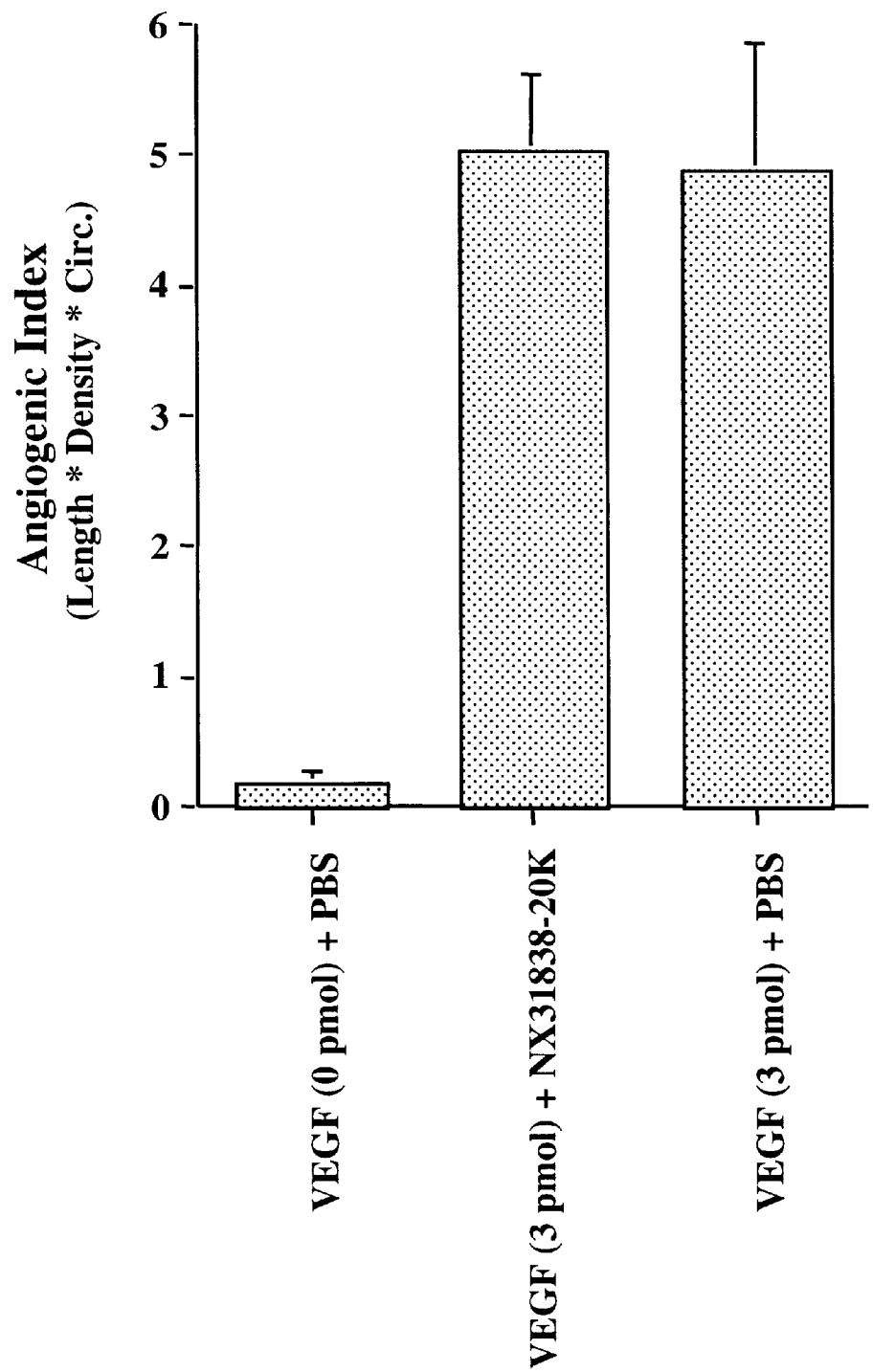
FIGS. 5A–5C shows the evaluation of Nucleic Acid Ligand attenuation of VEGF-induced corneal angiogenesis. Zero or three pmol of VEGF protein were incorporated in a biopolymer (Hydron) and implanted in the corneal stroma. Animals were treated intravenously twice daily with either PBS or Nucleic Acid Ligand as indicated for 5 days. Figures A, B, and C illustrate the effect of systemic treatment with NX31838-20K PEG, NX31838-40K PEG, or NX31838-PL Nucleic Acid Ligand on neovascularization. Values are mean ±SEM. * $P<0.05$ compared with 3 pmol VEGF+PBS group. See FIG. 1 for molecular descriptions.
Figure 5B:
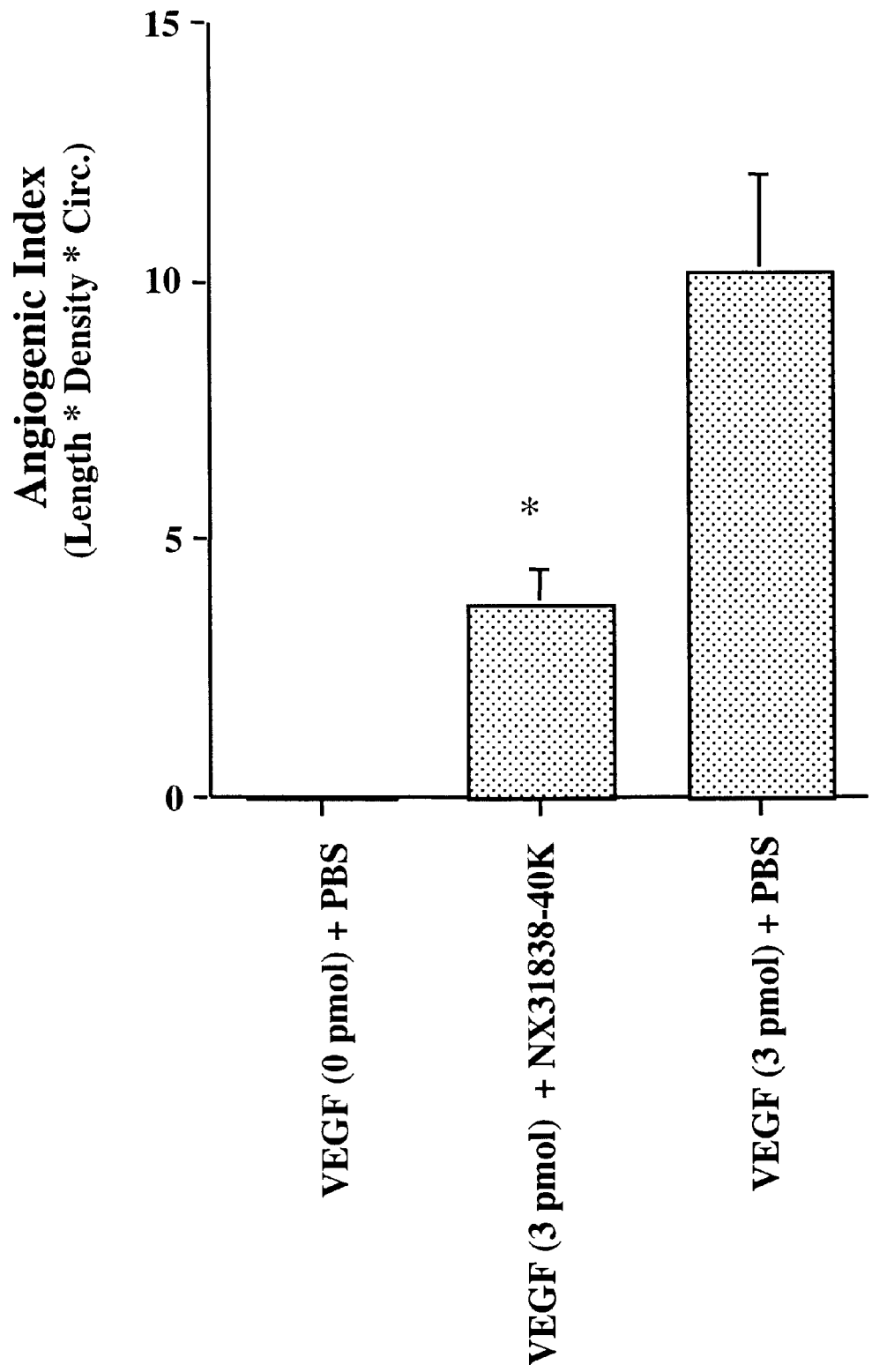
Figure 5C:
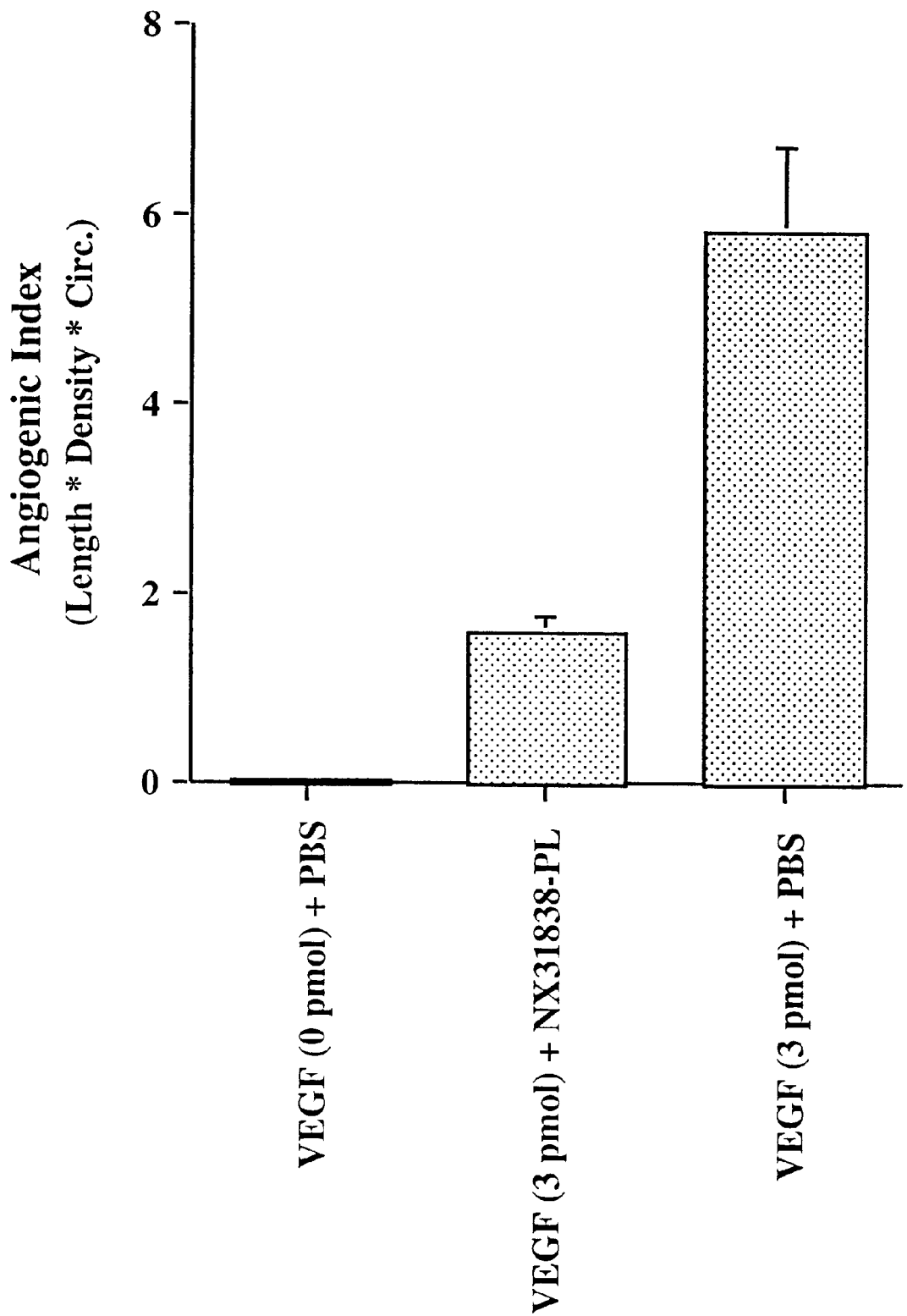

The ability of Nucleic Acid Ligand formulations to block VEGF-induced angiogenesis is seen in FIGS. 5A–C. Despite being equally effective as the other formulations in blocking vascular permeability changes, NX31838-20K PEG was ineffective at attenuating the angiogenic response in the normally avascular cornea. However, both NX31838-40K PEG and liposomal NX31838-PL significantly reduced the level of angiogenesis by 65–70%. It is presumed that these differences are attributable to the respective pharmacokinetic profiles of the Nucleic Acid Ligands.

Statistical Analysis: Groups in the Miles assay and corneal angiogenesis models were compared using Rank ANOVA with Dunnett's comparisons.

Figure 1F:
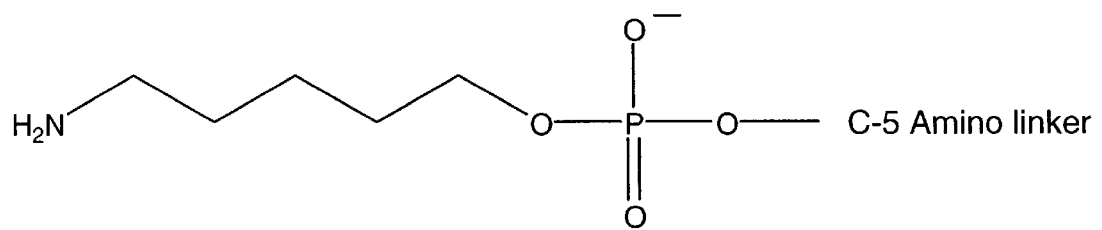
Figure 1G:
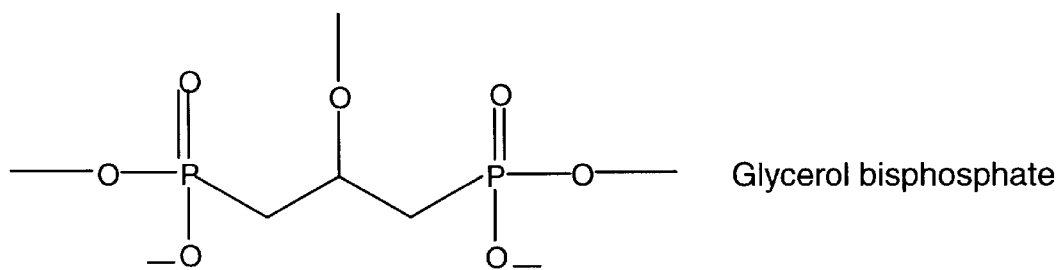
Figure 1H:
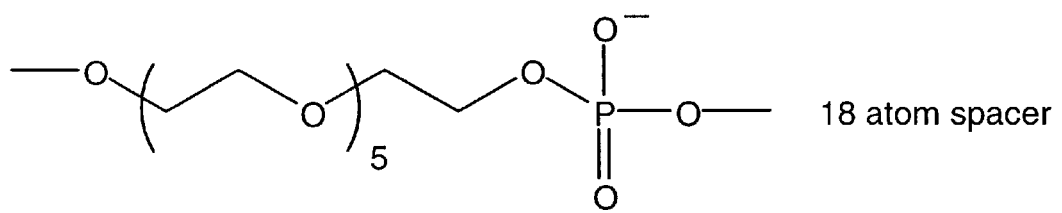
Figure 1I:
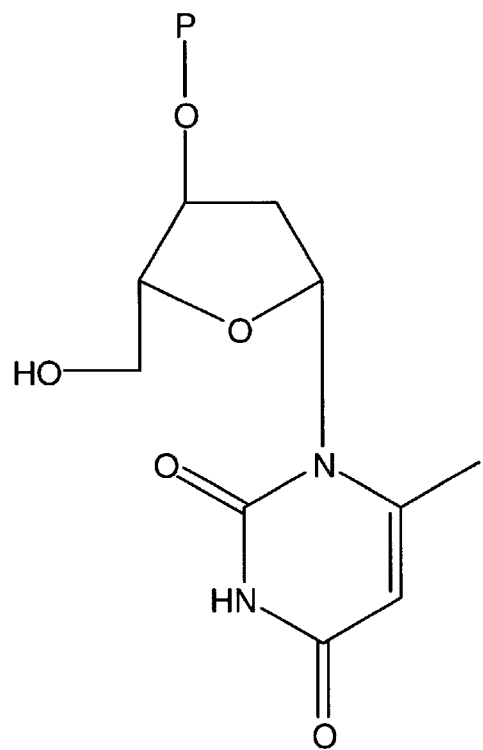

Intravitreal Pharmacokinetics of VEGF Nucleic Acid Ligand NX31838+40KPEG in Rabbits: New Zealand White rabbits were treated with VEGF Nucleic Acid Ligand NX31838 conjugated to 4OmPEG by intravitreal administration at a dose of 0.5 mg/eye. 40 mPEG was conjugated to the VEGF Nucleic Acid Ligand as described in Example 3, and the resulting complex is as shown in FIG. 1D (SEQ ID NO: 8). Rabbits received intravitreal injection of NX31838-40 mPEG in each eye. The time between doses for a given animal did not exceed 15 minutes. Blood and vitreous samples were collected as specified in Table 5.

Analysis of plasma and vitreous samples were carried out by the use of a double hybridization assay. In this assay, two hybridization probes are used, a capture probe attached to wells of 96 well plates, and a biotinylated detect probe. The capture probe forms a hybrid with the 5' end of the Nucleic Acid Ligand. This assay is high specific and sensitive to full length Nucleic Acid Ligand to yield a positive signal. The current limit of quantitation is approximately 2 fmoles in 5 ul of plasma.

Figure 6:
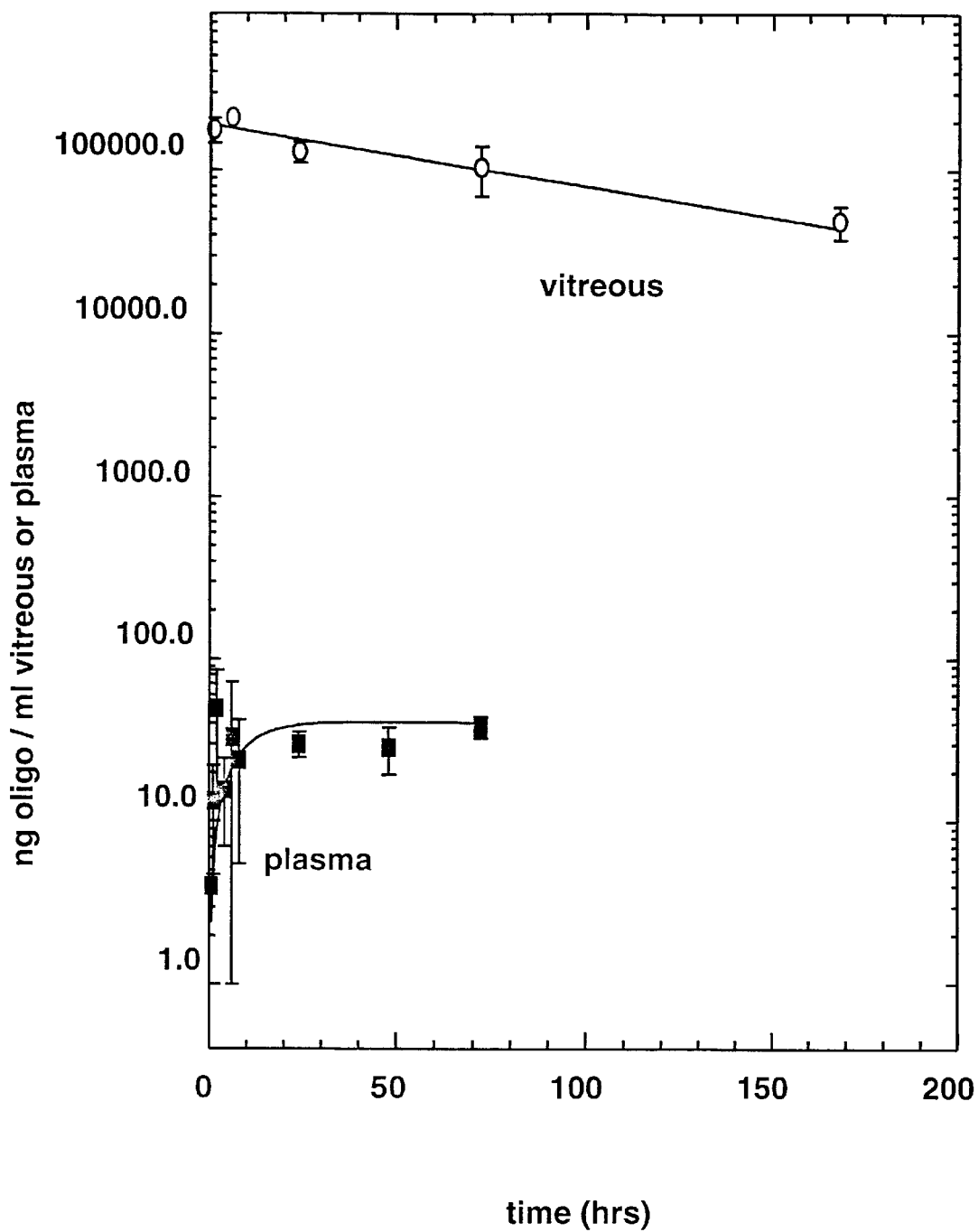
FIG. 6 summarizes the data for the plasma (■) or vitreous (○) concentration of NX3183 8-40KmPEG as a function of time following administration.

The preliminary results for both vitreous and plasma levels as a function of time following injection are shown in FIG. 6. High levels of Nucleic Acid Ligand are observed in the vitreous with corresponding low levels in plasma over the time course. Initially the concentration of Nucleic Acid Ligand in vitreous is 140,000–220,000 ng /ml vitreous and decreases with a $t_{1/2}$ of approximately 80 hours. The plasma levels appear to reach steady state by 2–4 hours at levels of 30–50 ng/ml plasma. These data are consistent with a highly stable (nuclease resistant) Nucleic Acid Ligand, as well as a slow rate of release from the eye.

TABLE 1

2'-F-pyrimidine ligands to VEGF$_{165}$

| Ligand (frequency) | Sequence of variable region 5'-gggaggacgaugcgg [variable region] cagacgacucgcccga-3' | | $K_d$ (pM) | SEQ. ID NO: 10 & 11 |
|---|---|---|---|---|
| Family 1 | | | | |
| VP30.7 | g | gAAGAAUUGG UCAUCGUCGUCUCCGCCUCCC | 3000 | 12 |
| VP30.12 | AAUACG | GAAGAAUUGG AUACAUAUGCUCGU | 7 | 13 |
| VP30.13 (7) | GAUAACA | GAAGAAUUGG UGAACAACGUGGU | 10 | 14 |
| VP30.16 | AUGAUCGCGUAG | GAAGUAUUGG AAGGCCCU | 6 | 15 |
| VP30.19 | CACUUUA | GAAGAAUUGA AUUUCCCGCUGGU | 9 | 16 |
| VP30.22 (6) | UAG | GAAGAAUUGG AAGCGCAUUUUCCUCGU | 20 | 17 |
| VP30.25 | CGGGAUUUUG | GAAGAAUUGG AUAUUGGCCU | 20 | 18 |
| VP30.26 (2) | CGGYACUUUG | GAAGAAUUGA AUUUCCCGCU | 10 | 19 |
| VP30.27 | g | gAAGAAUUGG AUAUAUCGUUCACCCCCACCU | 400 | 20 |
| VP30.40 | AAACG | GAAGAAUUGG AUACGCAAGCACGUU | 6 | 21 |

TABLE 1-continued

2'-F-pyrimidine ligands to VEGF_165

| Ligand (frequency) | Sequence of variable region 5'-gggaggacgaugcgg [variable region] cagacgacucgcccga-3' | | | | | $K_d$ (pM) | SEQ. ID NO: 10 & 11 |
|---|---|---|---|---|---|---|---|
| VP30.41 | UAG | GAAGUAUUGU | AAGCGCCUCGUUUUCGC | | | 7 | 22 |
| VP30.51 (2) | AGUUUUG | GAAGAAUUGG | AUGUUCCGAUCGU | | | 90 | 23 |
| VP30.54 | AAGAAACG | GAAGAAUUGG | AGACACGCUCGU | | | 10 | 24 |
| VP40.4 (5) | g | GAAGAAUUGA | UGUUGUAUUGUCCUUCCGAUUUCCUGCCGU | | | 200 | 25 |
| VP40.43 | ACA | GAAGAAUUGG | GCUUCGCAUUAUCCUCUGUCAGCCGC | | | 30 | 26 |
| VP40.53 | UGAGAGAAACG | GAAGAAUUGG | AUACGAUACUCAUCGCGCU | | | 8 | 27 |
| VT30.4 | CUUAAGUUUUG | GAAGAAUUGA | UACUGGGU | | | 20 | 28 |
| VT30.7 | UAACCAGUG | GAAGAAUUGG | CUGCUAUCCU | | | 10 | 29 |
| VT30.10 | AACG | GAAGAAUUGG | AUACGUAGCAUGCGU | | | 2 | 30 |
| VT30.13 | CAGGAUUUUG | GAAGAAUUGG | AUAUUGGCCGca | | | 10 | 31 |
| VT30.20 | AAACG | GAAGAAUUGG | AUACCGCUACGUGUU | | | 4 | 32 |
| VT30.52 | g | gAAGAAUUGA | GCAUUCCUUCUCCUUGUGCCU | | | 9000 | 33 |
| VT30.53 | AGCUAACG | GAAGAAUUGG | AAACAACCGCGUc | | | 10 | 34 |
| Family 2 | | | | | | | |
| VP30.2 (5) | ggUCA | ACCGA | UUGAA | UUU | UUGGACGC UCGCCU | 10 | 35 |
| VP30.5 (4) | gAYCA | ACCGA | UUGAC | GUUA | UUGGACGC UGGUc | 8 | 36 |
| VP30.31 (5) | gcggUA | ACCGA | UUGAA | CUUC | UUGGACGC UACCGU | 6 | 37 |
| VP30.43 | ggUA | ACCGAA | UUGAA | GUUA | UUGGACGC UACCU | 5 | 38 |
| VP40.9 | gGAGCAGA | ACCGA | UAGAA | GAA | UUGGACGC UCAGCUCCGGGU | 30 | 39 |
| VP40.14 | GUACCAGAAUGAGCA | ACCGA | AUGAA | GAA | CUGGACGC UGCUca | 8 | 40 |
| VP40.17 | ugcggUGA | ACCGA | UGGAA | UCGC | UUGGACGC UCAUCGCACGUUGCU | 10 | 41 |
| VT30.9 (6) | ggUCA | ACCGG | UUGAA | UAU | UUGGUCGC UGACCU | 30 | 42 |
| Family 3 | | | | | | | |
| VT30.1 (2) | gacgaugcgg | A | ACUA | GUGAAUGCUU AUA | CGA | CCGUGUUGUc | 10 | 43 |
| VT30.2 | gcgg | | AUCA | GUGAAUGCUU AUA | GA | CCGCCUCCGU | 2 | 44 |
| VT30.3 (8) | gaugcgg | AGA | AUCA | GUGAAUGCUU AUA | AAUC | UCGYGUc | 5 | 45 |
| VT30.11 | gaugcgg | A | AUCA | GUGAAUGCUU AUA | GCUC | CCGCGUCCU | 4 | 46 |
| VT30.15 | gcgg | A | ACCA | GUGAAUGCUU AUA | AGA | CUGCUCGU | 3 | 47 |
| VT30.21 | cgaugcgg | | AUCA | GUGAAUGCUU AUA | GA | CCGUAUUGCGU | 6 | 48 |
| VT30.28 | gaugcgg | AGA | AUCA | GUGAAUGCUU AUA | AACC | UCGUGUc | 60 | 49 |
| VT30.29 | augcggA | | AUCA | GUGAAUGCUU AUA | GC | UCCGCGUGGU | 10 | 50 |
| VT30.35 | cgg | | ACCA | GUGAAUGCUU AUA | AGCCCA | UCGACCU | N.D. | 51 |
| VT30.41 | gaugcgg | | CAGG | GUGAAUGCCA AUG | UACUUU | UCGCGUc | 40 | 52 |
| VT30.44 | gcggA | | AUCA | GUGAAUGCAA AUA | CA | UCCGCUCGGU | 10 | 53 |
| VT30.54 | gcggG | | ACUAG | GUGAAUGCCA AUA | UUCUUC | UCCGU | 10 | 54 |

TABLE 2

Effect of truncation on high affinity binding of VEGF ligands.

| Ligand | Sequence | Length (nts) | KD (pM) | SEQ ID NO: |
|---|---|---|---|---|
| t22 | GACGAUGCGGUAGGAAGAAUUGGAAGCGC* | 29 | 70 | 55 |
| t22a | GACGAUGCGGUAGGAAGAAUUGGAAGCG | 28 | 3000 | 56 |
| t22b | ACGAUGCGGUAGGAAGAAUUGGAAGCGC | 28 | 80 | 57 |
| t22c | GCGGUAGGAAGAAUUGGAAGCGC | 23 | 90 | 58 |
| t22d | CGGUAGGAAGAAUUGGAAGCGC | 22 | 100 | 59 |
| t22e | GGUAGGAAGAAUUGGAAGCGC* | 21 | 200 | 60 |
| t22f | GUAGGAAGAAUUGGAAGCGC* | 20 | >100,000 | 61 |
| t2 | GGCGAACCGAUGGAAUUUUUGGACGCUCGCC* | 31 | 20 | 62 |
| t2a | *GCGAACCGAUGGAAUUUUUGGACGCUCGC | 29 | 40 | 63 |
| t2b | CGAACCGAUGGAAUUUUUGGACGCUCG | 27 | 100 | 64 |
| t2c | GAACCGAUGGAAUUUUUGGACGCUC* | 25 | 200 | 65 |
| t2d | AACCGAUGGAAUUUUUGGACGCU* | 23 | 20,000 | 66 |
| t2e | ACCGAUGGAAUUUUUGGACGC* | 21 | >100,00 | 67 |
| t44 | GCGGAAUCAGUGAAUGCUUAUACAUCCGC* | 29 | 10 | 68 |
| t44a | CGGAAUCAGUGAAUGCUUAUACAUCCG | 27 | 10 | 69 |
| t44b | GGAAUCAGUGAAUGCUUAUACAUCC | 25 | 60 | 70 |
| t44c | GAAUCAGUGAAUGCUUAUACAUC* | 23 | 2000 | 71 |
| t44d | AAUCAGUGAAUGCUUAUACAU* | 21 | >100,000 | 72 |
| t44e | AUCAGUGAAUGCUUAUACA* | 19 | >100,000 | 73 |

TABLE 3

Effect of 2'-OMe-purine substitutions on affinity for VEGF.

| Ligand | Sequence | $K_D$ (pM) | SEQ NO: |
|---|---|---|---|
| t22OMe (OH-10,12,22) | GACGAUGCGGUAGGAAGAAUUGGAAGCGC | 10 | 74 |
| t22OMe (OH-10,12) | GACGAUGCGGUAGGAAGAAUUGGAAGCGC | 20 | 75 |
| t22OMe (OH-10,22) | GACGAUGCGGUAGGAAGAAUUGGAAGCGC | 4,000 | 76 |
| t22OMe (OH-12,22) | GACGAUGCGGUAGGAAGAAUUGGAAGCGC | 90 | 77 |
| t2OMe (OH-6,21) | GGCGAACCGAUGGAAUUUUUGGACGCUCGCC | 60 | 78 |
| t2OMe (OH-6) | GGCGAACCGAUGGAAUUUUUGGACGCUCGCC | 500 | 79 |
| t2OMe (OH-21) | GGCGAACCGAUGGAAUUUUUGGACGCUCGCC | 20,000 | 80 |
| t44OMe (OH-5,6) | GCGGAAUCAGUGAAUGCUUAUACAUCCGC | 40 | 81 |
| t44OMe (QH-5) | GCGGAAUCAGUGAAUGCUUAUACAUCCGC | >100,000 | 82 |
| t44OMe (OH-6) | GCGGAAUCAGUGAAUGCUUAUACAUCCGC | >100,000 | 83 |

TABLE 4

Binding Parameters of 2'-Ome-substituted minimal ligands.

| Ligand Sequence | $K_D$ (s.d.) (pM) | $k_d$ (s.d.) (sec$^{-1}$) | $k_a$ (M$^{-1}$ sec$^{-1}$) | SEQ ID NO: |
|---|---|---|---|---|
| t22OMe GCGGUAGGAAGAAUUGGAAGCGC | 67 (36) | 0.012 (0.004) | $1.8 \times 10^8$ | 84 |
| t2OMe GCGAACCGAUGGAAUUUUUGGACGCUCGC | 140 (50) | 0.0042 (0.002) | $3.0 \times 10^7$ | 85 |
| t44OMe CGGAAUCAGUGAAUGCUUAUACAUCCG | 51 (11) | 0.0074 (0.002) | $1.5 \times 10^8$ | 86 |

TABLE 5

Group Assignments and Sample Times

| Group # | # of Rabbits | Blood Sample Time | Termination |
|---|---|---|---|
| 1 | 2 | predose, 15 min, 30 min, 1 hrs, | 1 hours |
| 2 | 2 | predose, 30 min, 1 hr, 2 hrs, 6 hrs, | 6 hours |
| 3 | 2 | predose, 1 hr, 4 hrs, 8 hrs, 24 hrs | 24 hours |
| 4 | 2 | predose, 15 min, 6 hrs, 8 hrs, 24 hrs, 48 hrs 72 hrs | 72 hours |
| 5 | 2 | predose, 2 hr, 4 hrs, 4 days, 5 days, | 7 days |

We claim:

1. A purified and isolated non-naturally occurring RNA ligand to Vascular Endothelial Growth Factor wherein said ligand is comprised of 2'fluoro (2'F)-modified nucleotides.

2. A method for improving the pharmacokinetic properties of VEGF Nucleic Acid Ligand in an occular application comprising covalently linking a Non-Immunogenic, High Molecular Weight compound to a VEGF Nucleic Acid Ligand to form a complex comprised of a VEGF Nucleic Acid Ligand and a Non-Immunogenic, High Molecular Weight Compound.

3. The RNA ligand to VEGF of claim 1 wherein said ligand is selected from the group consisting of the sequences set forth in Tables 1–4 (SEQ ID NOS: 10–86).

4. The RNA ligand of claim 3 wherein said ligand is substantially homologous to and has substantially the same ability to bind VEGF as a ligand selected from the group consisting of the sequences set forth in Tables 1–4 (SEQ ID NOS: 10–86).

5. The RNA ligand of claim 3 wherein said ligand is substantially the same structure and substantially the same ability to bind VEGF as a ligand selected from the group consisting of the sequences set forth in Tables 1–4 (SEQ ID NOS: 10–86).

6. The RNA ligand to VEGF of claim 1 identified according to the method comprising:

a) contacting a Candidate Mixture of RNA with VEGF, wherein the RNA having an increased affinity to VEGF relative to the Candidate Mixture may be partitioned from the remainder of the Candidate Mixture;

b) partitioning the increased affinity RNA from the remainder of the Candidate Mixture; and c) amplifying the increased affinity RNA to yield a mixture of RNA enriched for RNA having an increased affinity for VEGF, whereby RNA Ligands of VEGF are identified.

7. The RNA ligand to VEGF of claim 3 identified according to the method comprising:

a) contacting a Candidate Mixture of RNA with VEGF, wherein the RNA having an increased affinity to VEGF relative to the Candidate Mixture may be partitioned from the remainder of the Candidate Mixture;

b) partitioning the increased affinity RNA from the remainder of the Candidate Mixture; and c) amplifying the increased affinity RNA to yield a mixture of RNA enriched for RNA having an increased affinity for VEGF; whereby RNA Ligands of VEGF are identified.

8. A Complex comprised of the RNA ligand to VEGF of claim 1 and a Non-Immunogenic, High Molecular Weight Compound.

9. The Complex of claim 8 further comprising a Linker between said ligand and said Non-Immunogenic, High Molecular Weight Compound.

10. The Complex of claim 8 wherein said Non-Immunogenic, High Molecular Weight Compound is a Polyalkylene Glycol.

11. The Complex of claim 10 wherein said Polyalkylene Glycol is polyethylene glycol.

12. The Complex of claim 11 wherein said polyethylene glycol has a molecular weight of about 10–80 Kd.

13. The Complex of claim 11 wherein said polyethylene glycol has a molecular weight of about 20–45 Kd.

14. The Complex of claim 11 wherein said Complex is

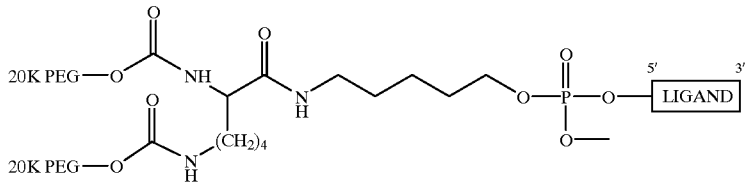

Ligand Component =
fCmGmGrArAfUfCmAmGfUmGmAmAfUmGfCfUfUmAfUmAfCmAfUfCfCmG-3'3'-dT (Seq. ID. NO:8).

15. The Complex of claim 11 wherein said Complex is

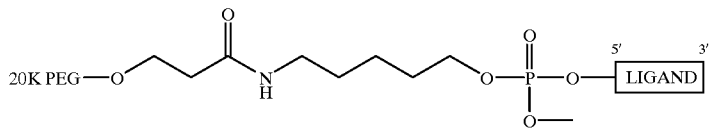

Ligand Component =
fCmGmGrArAfUfCmAmGfUmGmAmAfUmGfCfUfUmAfUmAfCmAfUfCfCmG-3'3'-dT (SEQ ID NO:9).

16. The method of claim 2 wherein said Non-Immunogenic, High Molecular Weight Compound is a Polyalkylene Glycol.

17. The method of claim 16 wherein said Polyalkylene Glycol is polyethylene glycol.

18. The method of claim 17 wherein said polyethylene glycol has a molecular weight of about 10–80 Kd.

19. The method of claim 17 wherein said polyethylene glycol has a molecular weight of about 20–45 Kd.

20. The method of claim 19 wherein said complex has the structure

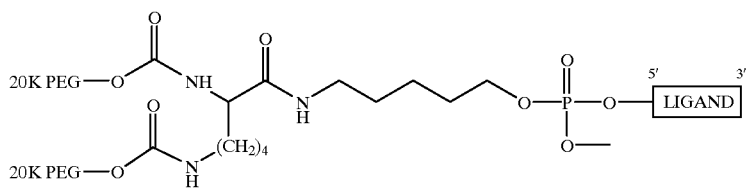
Ligand Component =
fCmGmGrArAfUfCmAmGfUmGmAmAfUmGfCfUfUmAfUmAfCmAfUfCfCmG-3'3'-dT (Seq. ID. NO:8).
21. The complex of claim 19 wherein said complex is
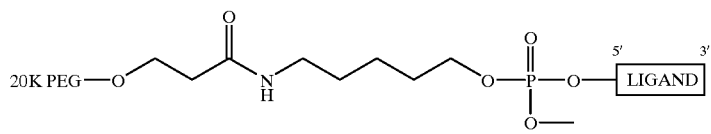
Ligand Component =
fCmGmGrArAfUfCmAmGfUmGmAmAfUmGfCfUfUmAfUmAfCmAfUfCfCmG-3'3'-dT (SEQ ID NO:9).
\* \* \* \* \*